(12) United States Patent
Howard et al.

(10) Patent No.: US 11,446,292 B2
(45) Date of Patent: *Sep. 20, 2022

(54) COMPOUNDS AND CONJUGATES THEREOF

(71) Applicant: MedImmune Limited, Cambridge (GB)

(72) Inventors: Philip Wilson Howard, Cambridge (GB); Niall Dickinson, Cambridge (GB); Thais Cailleau, Cambridge (GB); Luke Masterson, Cambridge (GB); William Goundry, Cambridge (GB)

(73) Assignee: MedImmune Limited, Cambridge (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/348,236

(22) Filed: Jun. 15, 2021

(65) Prior Publication Data
US 2021/0322401 A1 Oct. 21, 2021

Related U.S. Application Data

(63) Continuation of application No. 16/826,405, filed on Mar. 23, 2020.

(60) Provisional application No. 62/964,177, filed on Jan. 22, 2020, provisional application No. 62/826,393, filed on Mar. 29, 2019.

(51) Int. Cl.
| | | |
|---|---|---|
| *A61K 31/4745* | (2006.01) | |
| *A61K 47/68* | (2017.01) | |
| *A61P 35/00* | (2006.01) | |
| *C07D 491/22* | (2006.01) | |
| *A61K 47/65* | (2017.01) | |
| *A61K 47/54* | (2017.01) | |

(52) U.S. Cl.
CPC ........ *A61K 31/4745* (2013.01); *A61K 47/545* (2017.08); *A61K 47/65* (2017.08); *A61K 47/6803* (2017.08); *A61P 35/00* (2018.01); *C07D 491/22* (2013.01)

(58) Field of Classification Search
CPC ............ A61K 31/4745; A61K 47/6803; C07D 491/22; A61P 35/00
See application file for complete search history.

(56) References Cited

U.S. PATENT DOCUMENTS

| | | |
|---|---|---|
| 4,816,567 A | 3/1989 | Cabilly |
| 5,658,920 A | 8/1997 | Ejima |
| 5,663,177 A | 9/1997 | Berges |
| 5,849,945 A | 12/1998 | Kamihara |
| 6,310,207 B1 | 10/2001 | Ahn |
| 6,407,115 B1 | 6/2002 | Ejima |
| 7,521,541 B2 | 4/2009 | Eigenbrot |
| 7,723,485 B2 | 5/2010 | Junutula |
| 8,236,319 B2 | 8/2012 | Chari |
| 9,061,995 B2 | 6/2015 | Chari |
| 2001/0034446 A1 | 10/2001 | Kaminhara |
| 2003/0109460 A1 | 6/2003 | Ando |
| 2003/0144304 A1 | 7/2003 | Murata |
| 2003/0176722 A1 | 9/2003 | Inoki |
| 2005/0059679 A1 | 3/2005 | Murata |
| 2006/0178376 A1 | 8/2006 | Fukuda |
| 2008/0015157 A1 | 1/2008 | Ohwada |
| 2009/0149478 A1 | 6/2009 | Endo |
| 2015/0297748 A1 | 10/2015 | Abe |
| 2015/0352224 A1 | 12/2015 | Abe |
| 2016/0279259 A1 | 9/2016 | Abe |
| 2016/0297890 A1 | 10/2016 | Agatsuma |
| 2016/0333112 A1 | 11/2016 | Abe |
| 2017/0035906 A1 | 2/2017 | Abe |
| 2018/0094073 A1 | 4/2018 | Agatsuma |

(Continued)

FOREIGN PATENT DOCUMENTS

| | | |
|---|---|---|
| EP | 0296597 A2 | 12/1988 |
| EP | 0495432 A1 | 7/1992 |

(Continued)

OTHER PUBLICATIONS

Sugimori et al., J. Med. Chem. 1998 vol. 41 2308-2318 (Year: 1998).*
Kim, et al., Biomol. Ther. 2015 23(6), 493-509 (Year: 2015).*
ADC Review editorial team; Published Mar. 22, 2019; available online at: https://www.adcreview.com/the-review/linkers/what-are-stable-linkers/; accessed Oct. 15, 2021 (Year: 2019).*
Smith, et al., ACS Med. Chem. Lett. 2018, vol. 9, pp. 56-60; published Dec. 6, 2017 (Year: 2018).*
Koniev, et al., Chem. Soc. Rev. 2015 vol. 44 5495-5551 (Year: 2015).*

(Continued)

*Primary Examiner* — Julie Wu
*Assistant Examiner* — John L Van Druff

(57) ABSTRACT

A conjugate comprising the following topoisomerase inhibitor derivative (A*):

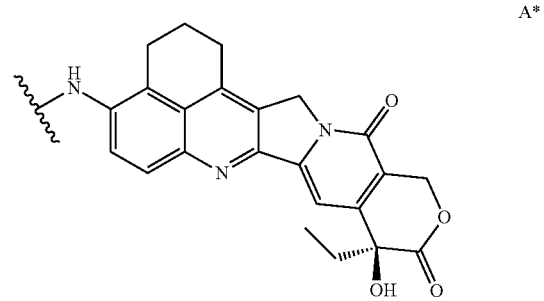

with a linker for connecting to a Ligand Unit, wherein the linker is attached in a cleavable manner to the amino residue. The Ligand Unit is preferably an antibody. Also provided is A* with the linking unit attached, and intermediates for their synthesis, as well as the released warhead.

15 Claims, 1 Drawing Sheet

Specification includes a Sequence Listing.

(56) References Cited

U.S. PATENT DOCUMENTS

| | | | |
|---|---|---|---|
| 2018/0147292 A1 | 5/2018 | Noguchi | |
| 2019/0225686 A1 | 7/2019 | Hirai | |
| 2019/0314362 A1 | 10/2019 | Ishida | |
| 2019/0330368 A1 | 10/2019 | Endo | |
| 2020/0061031 A1 | 2/2020 | Hirotani | |
| 2020/0306243 A1* | 10/2020 | Howard | A61K 47/6889 |

FOREIGN PATENT DOCUMENTS

| | | | | |
|---|---|---|---|---|
| EP | 0737686 A1 | 10/1996 | | |
| EP | 0811603 A1 | 12/1997 | | |
| EP | 3626825 A1 | 3/2020 | | |
| WO | 199902530 A1 | 1/1999 | | |
| WO | 2003045952 A2 | 6/2003 | | |
| WO | 2004073601 A2 | 9/2004 | | |
| WO | 2007044515 A1 | 4/2007 | | |
| WO | 2007085930 A1 | 8/2008 | | |
| WO | 2009052249 A1 | 4/2009 | | |
| WO | 2009134977 A1 | 11/2009 | | |
| WO | 2015081282 A1 | 6/2015 | | |
| WO | WO-2015081282 A1 * | 6/2015 | | A61K 47/6803 |
| WO | 2015146132 A1 | 10/2015 | | |
| WO | 2015155998 A1 | 10/2015 | | |
| WO | 2016053107 A1 | 4/2016 | | |
| WO | 2016123582 A1 | 8/2016 | | |
| WO | 2017186894 A1 | 11/2017 | | |
| WO | 2018089393 A1 | 5/2018 | | |
| WO | 2019034176 A1 | 2/2019 | | |
| WO | 2019034177 A1 | 2/2019 | | |

OTHER PUBLICATIONS

Burke et al., "Design, Synthesis, and Biological Evaluation of Antibody-Drug Conjugates Comprised of Potent Camptothecin Analogues", Bioconjugate Chemistry, 2009, vol. 20, No. 6, pp. 1242-1250.
Cardillo et al., "Sacituzumab Govitecan (IMMU-132), an Anti-Trop 2/SN-38 Antibody-Drug Conjugate: Characterization and Efficacy in Pancreatic, Gastric, and Other Cancers", Bioconjugate Chemistry, 2015, vol. 26(5), pp. 919-931.
Clackson et al., "Making antibody fragments using phage display libraries", Nature, 1991, vol. 352, pp. 624-628.
Dimasi et al., "Efficient Preparation of Site-Specific Antibody-Drug Conjugates Using Cysteine Insertion", Molecular Pharmaceutics, 2017, vol. 14, pp. 1501-1516.
Dornan et al., "Therapeutic potential of an anti-CD79B antibody-drug conjugate, anti-CD79b-vc-MMAE, for the treatment of non-Hodgkin lymphoma", Blood, 2009, vol. 114(13), pp. 2721-2729.
Dubowchik et al., "Cathepsin B-Labile Dipeptide Linkers for Lysosomal Release of Doxombicin from Internalizing Immunoconjugates: Model Studies of Enzymatic Drug Release and Antigen-Specific In Vitro Anticancer Activity", Bioconjugate Chemistry, 2002, vol. 13, pp. 855-869.
Hamblett et al., "Effects of Drug Loading on the Antitumor Activity of a Monoclonal Antibody Drug Conjugate", Clinical Cancer Research, 2004, vol. 10, pp. 7063-7070.
Junutula et al., "Site-specific conjugation of a cytotoxic drug to an antibody improves the therapeutic index", Nature Biotechnology, 2008, vol. 26(8), pp. 925-932.
Kohler et al., "Continuous cultures of fused cells secreting antibody of predefined specificity", Nature, 1975, vol. 256, pp. 495-497.
Lonberg, "Fully human antibodies from transgenic mouse and phage display platforms", Current Opinion in Immunology, 2008, vol. 20(4), pp. 450-459.
Marks et al., "By-passing Immunization Human Antibodies from V-gene Libraries Displayed on Phage", 1991, J. Mol. Biol., vol. 222, pp. 581-597.
Miller et al., "Design, Construction, and In Vitro Analyses of Multivalent Antibodies", Journal of Immunology, 2003, vol. 170, pp. 4854-4861.
Moon et al., "Antibody Conjugates of 7-Ethyl-10-hydroxycamptothecin (SN-38) for Targeted Cancer Chemotherapy", J. Med. Chem., 2008, vol. 51(21), pp. 6916-6926.
Nakada et al., "Novel antibody drug conjugates containing exatecan derivative-based cytotoxic payloads", Bioorganic & Medicinal Chemistry Letters, 2016, vol. 26, pp. 1542-1545.
Nicolaou et al., "Calicheamicin θ 1I: A Rationally Designed Molecule with Extremely Potent and Selective DNA Cleaving Properties and Apoptosis Inducing Activity", Angew Chem. Intl. Ed. Engl., 1994, vol. 33, pp. 183-186.
Ogitani et al., "DS-8201a, A Novel HER2-Targeting ADC with a Novel DNA Topoisomerase I Inhibitor, Demonstrates a Promising Antitumor Efficacy with Differentiation from T-DM1", Clinical Cancer Research, 2016, vol. 22, pp. 5097-5108.
Sanderson et al., "In vivo Drug-Linker Stability of an Anti-CD30 Dipeptide-Linked Auristatin Immunoconjugate", 2005, Clinical Cancer Research, vol. 11, pp. 843-852.
Sugimori et al., "Synthesis and Antitumor Activity of Ring A- and F-Modified Hexacyclic Camptothecin Analogues", J Med Chem, 1998, vol. 41, pp. 2308-2318.
Takegawa et al., "DS-8201a, a new HER2-targeting antibody-drug conjugate incorporating a novel DNA topoisomerase I inhibitor, overcomes HER2-positive gastric cancer T-DM1 resistance", International Journal of Cancer, 2017, vol. 141, pp. 1682-1689.
Kim et al., "Strategies and Advancement in Antibody-Drug Conjugate Optimization for Targeted Cancer Therapeutics" Biomol Ther (Seoul). Nov. 2015;23(6):493-509.
Smith, et al., "Design and Synthesis of Isoquinolidinobenzodiazepine Dimers, a Novel Class of Antibody-Drug Conjugate Payload", ACS Med. Chem. Lett. 2018, vol. 9, pp. 56-60; published Dec. 6, 2017.
Koniev, et al., "Developments and recent advancements in the field of endogenous amino acid selective bond forming reactions for bioconjugation",Chem. Soc. Rev. 2015 vol. 44 5495-5551.
Francisco et al. "cAC10-vcMMAE, an anti-CD30-monomethyl auristatin E conjugate with potent and selective antitumor activity" Blood, Aug. 15, 2003, vol. 102, 1458-1465.
Carl et al. "A novel connector linkage applicable in prodrug design", J. Med. Chem. 1981, 24, 5, 479-480.
Dubowchik et al "Cathepsin B-sensitive dipeptide prodrugs. 1. A model study of structural requirements for efficient release of doxorubicin", Bioorg Med Chem Lett. Dec. 1, 1998;8(23):3341-6.
Dubowchik et al "Cathepsin B-Labile Dipeptide Linkers for Lysosomal Release of Doxorubicin from Internalizing Immunoconjugates: Model Studies of Enzymatic Drug Release and Antigen-Specific In Vitro Anticancer Activity" Bioconjugate Chem. 2002, 13, 4, 855-869.
Toki et al. "Protease-mediated fragmentation of p-amidobenzyl ethers: a new strategy for the activation of anticancer prodrugs" J Org Chem. Mar. 22, 2002;67(6):1866-72.
U.S. Appl. No. 16/826,405, filed Mar. 23, 2020.
U.S. Appl. No. 17/599,374, filed Mar. 23, 2020.

* cited by examiner

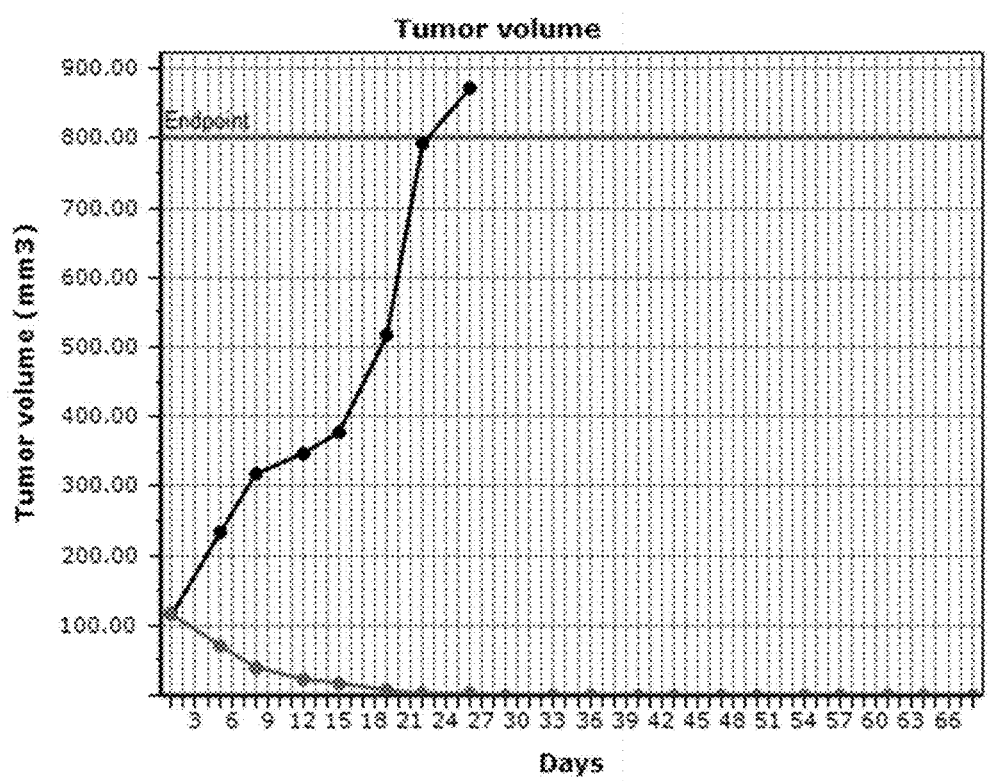

SEQUENCE LISTING

<160> NUMBER OF SEQ ID NOS: 4

<210> SEQ ID NO 1
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 1

Asn Ala Val Pro Asn Leu Arg Gly Asp Leu Gln Val Leu Ala Gln Lys
1               5                   10                  15

Val Ala Arg Thr Cys
            20

```
<210> SEQ ID NO 2
<211> LENGTH: 21
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"
<220> FEATURE:
<221> NAME/KEY: MOD_RES
<222> LOCATION: (4)..(18)
<223> OTHER INFORMATION: Any amino acid

<400> SEQUENCE: 2

Asn Ala Val Xaa Xaa Xaa Xaa Xaa Xaa Xaa Xaa Xaa Xaa Xaa Xaa Xaa
1               5                   10                  15

Xaa Xaa Arg Thr Cys
            20

<210> SEQ ID NO 3
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 3

Gly Gly Phe Gly
1

<210> SEQ ID NO 4
<211> LENGTH: 4
<212> TYPE: PRT
<213> ORGANISM: Artificial Sequence
<220> FEATURE:
<221> NAME/KEY: source
<223> OTHER INFORMATION: /note="Description of Artificial Sequence:
      Synthetic peptide"

<400> SEQUENCE: 4

Gly Phe Gly Gly
1
```

COMPOUNDS AND CONJUGATES THEREOF

The present invention relates to targeted conjugates comprising a specific topoisomerase inhibitor and compounds useful in their synthesis, as well as the released warhead.

BACKGROUND TO THE INVENTION

Topoisomerase Inhibitors

Topoisomerase inhibitors are chemical compounds that block the action of topoisomerase (topoisomerase I and II), which is a type of enzyme that controls the changes in DNA structure by catalyzing the breaking and rejoining of the phosphodiester backbone of DNA strands during the normal cell cycle.

The following compound:

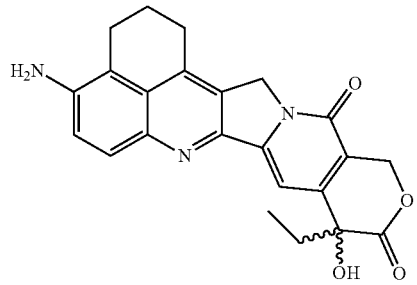

$A^R$ in racemic form was disclosed in EP 0296597 (Example 63). It is also disclosed (as compound 34 in racemic form) in Sugimori, M., et al., *J Med Chem*, 1998, 41, 2308-2318 (DOI: 10.1021/jm970765q), where its biological activity is discussed, alongside that of a number of related compounds.

Various topoisomerase inhibitors, such as irinotecan and exatecan derivatives and doxorubicin, have been included in antibody drug conjugates. For example, Daiichi Sankyo have DS-8201a in clinical trials:

where the antibody is Her2 (Takegawa, N., et al., *Int J Cancer*, 2017, 141, 1682-1689 (DOI: 10.1002/ijc.30870). This ADC releases the exatecan derivative:

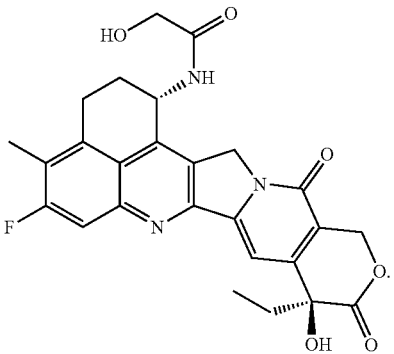 [SMILES: CC[C@@]1(O)C(=O)OCc2c1cc1n(c2=O)Cc2c-1nc1cc(F)c(C)c3c1c2[C@@H](NC(=O)CO)CC3]

Burke, P. J., et al., Bioconjugate Chem., 2009, 20, 1242-1250, discloses conjugates of:

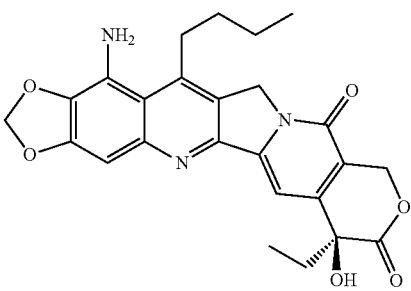 [SMILES: CCCCc1c2c(nc3cc4c(c(N)c13)OCO4)-c1cc3c(c(=O)n1C2)COC(=O)[C@]3(O)CC]

which are linked via the amino group with the following structures:

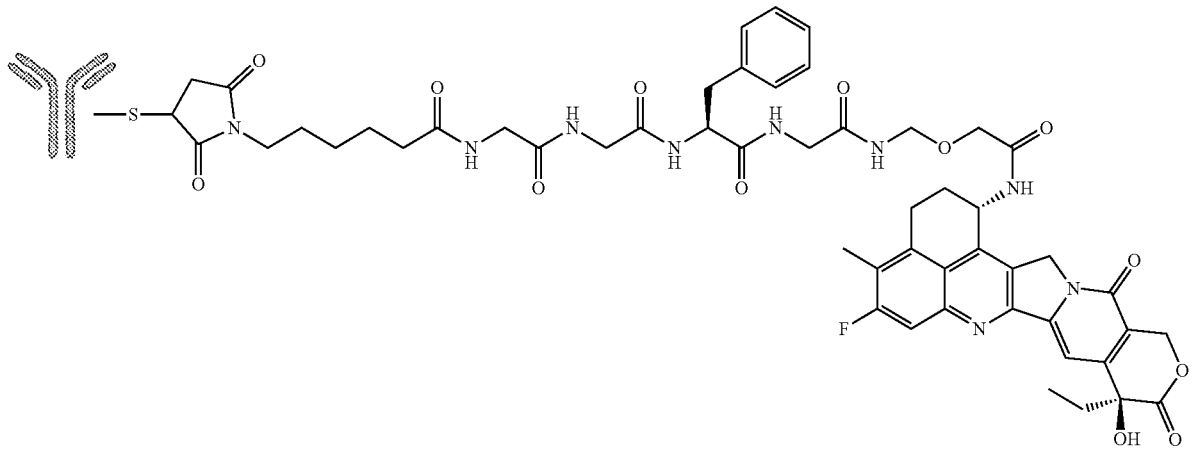

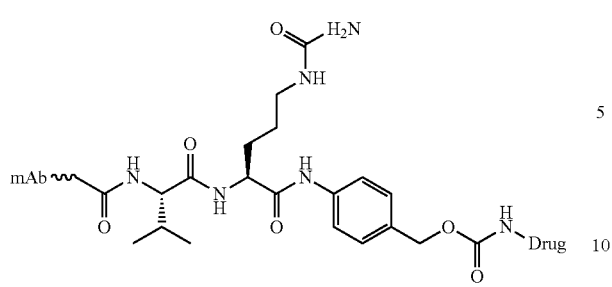

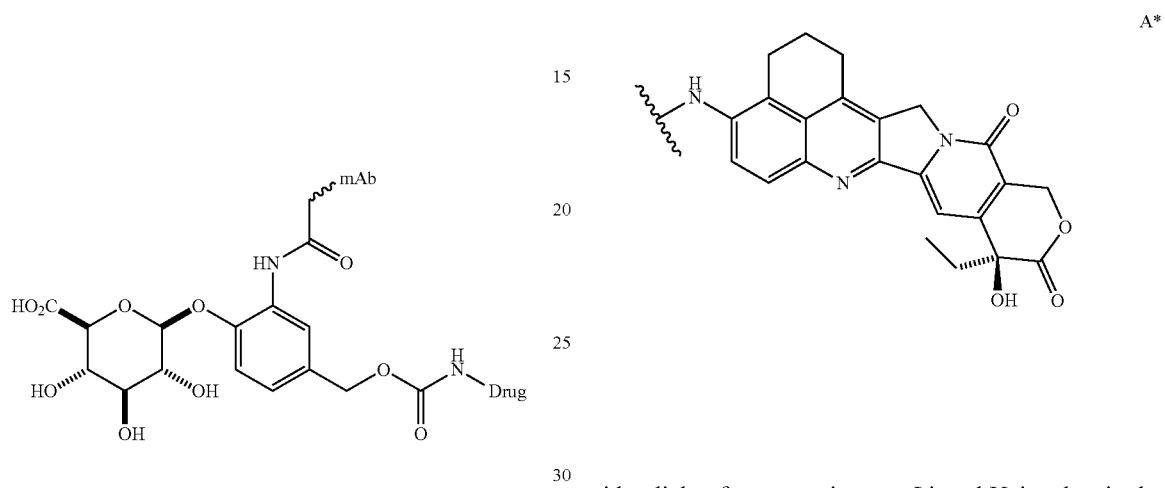

which include a PABC (para-aminobenzyloxycarbonyl) group.

Immunomedics have Sacituzumab Govitecan (IMMU-132) in clinical trials (Cardillo, T. M., et al., *Bioconjugate Chem*, 2015, 26(5), 919-931, DOI: 10.1021/acs.bioconjchem.5b00223)

SUMMARY OF THE INVENTION

In a general aspect the present invention provides a conjugate comprising the following topoisomerase inhibitor derivative (A*, the Drug Unit):

A* with a linker for connecting to a Ligand Unit, wherein the linker is attached in a cleavable manner to the amino residue. The Ligand Unit is preferably an antibody. The invention also provides A* with the linking unit attached, and intermediates for their synthesis, as well as the released warhead.

A first aspect of the present invention comprises a compound with the formula I:

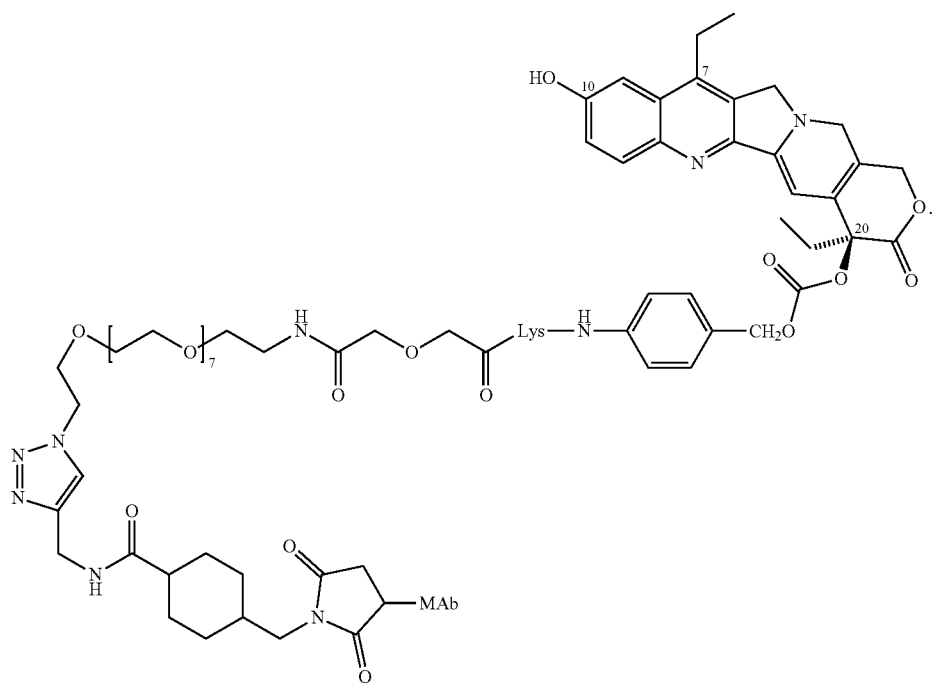

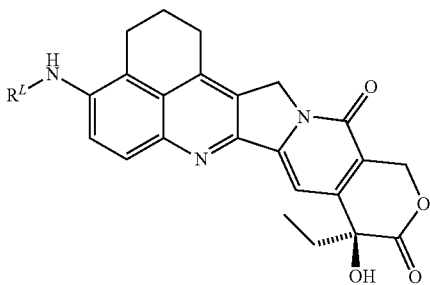

and salts and solvates thereof, wherein $R^L$ is a linker for connection to a Ligand Unit, which is selected from:
(ia):

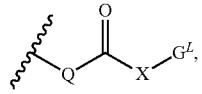

wherein
Q is:

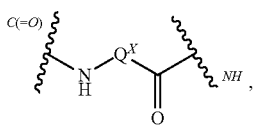

where $Q_X$ is such that Q is an amino-acid residue, a dipeptide residue, a tripeptide residue or a tetrapeptide residue;
X is:

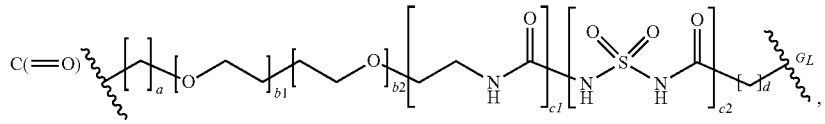

where a=0 to 5, b1=0 to 16, b2=0 to 16, c1=0 or 1, c2=0 or 1, d=0 to 5, wherein at least b1 or b2=0 (i.e. only one of b1 and b2 may not be 0) and at least c1 or c2=0 (i.e. only one of c1 and c2 may not be 0);
$G^L$ is a linker for connecting to a Ligand Unit;
(ib):

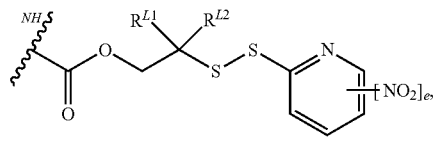

where $R^{L1}$ and $R^{L2}$ are independently selected from H and methyl, or together with the carbon atom to which they are bound form a cyclopropylene or cyclobutylene group; and
e is 0 or 1.

A second aspect of the present invention provides a method of making a compound of the first aspect of the invention, comprising at least one of the method steps set out below.

In a third aspect, the present invention provides a conjugates of formula IV:

$$L\text{-}(D^L)_p \quad (IV)$$

or a pharmaceutically acceptable salt or solvate thereof, wherein L is a Ligand unit (i.e., a targeting agent), $D^L$ is a Drug Linker unit that is of formula III:

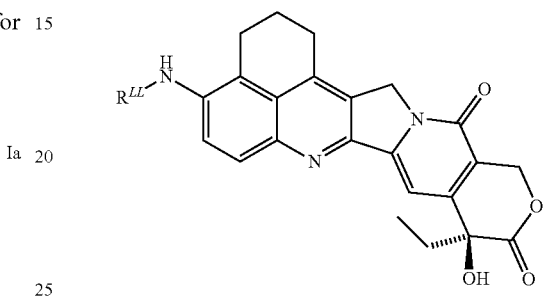

$R^{LL}$ is a linker connected to the Ligand unit selected from (ia'):

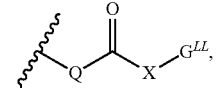

where Q and X are as defined in the first aspect and $G^{LL}$ is a linker connected to a Ligand Unit; and (ib'):

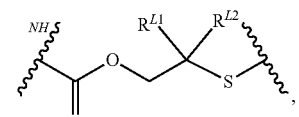

where $R^{L1}$ and $R^{L2}$ are as defined in the first aspect; and p is an integer of from 1 to 20.

Accordingly, the Conjugates comprise a Ligand unit covalently linked to at least one Drug unit (A*) by a Linker unit (i.e. a Ligand unit with one or more Drug-Linker units attached). The Ligand unit, described more fully below, is a targeting agent that binds to a target moiety. The Ligand unit can, for example, specifically bind to a cell component (a Cell Binding Agent) or to other target molecules of interest. Accordingly, the present invention also provides methods for the treatment of, for example, various cancers and autoimmune disease. These methods encompass the use of the Conjugates wherein the Ligand unit is a targeting agent that specifically binds to a target molecule. The Ligand unit can be, for example, a protein, polypeptide or peptide, such as an antibody, an antigen-binding fragment of an antibody, or other binding agent, such as an Fc fusion protein.

The drug loading is represented by p, the number of drug units per Ligand unit (e.g., an antibody). Drug loading may range from 1 to 20 Drug units (D) per Ligand unit (e.g., Ab or mAb). For compositions, p represents the average drug loading of the Conjugates in the composition, and p ranges from 1 to 20.

A fourth aspect of the present invention provides the use of a conjugate of the third aspect of the invention in the manufacture of a medicament for treating a proliferative disease. The fourth aspect also provides a conjugate of the third aspect of the invention for use in the treatment of a proliferative disease.

One of ordinary skill in the art is readily able to determine whether or not a candidate compound treats a proliferative condition for any particular cell type. For example, assays which may conveniently be used to assess the activity offered by a particular compound are described in the examples below.

In Nakada, et al., *Bioorg Med Chem Lett*, 26 (2016), 1542-1545 (DOI: 10.1016/j.bmcl.2016.02.020) discusses a series of ADCs:

and concludes that the decreased cytotoxicity of ADCs (1) and (2) may be due to the steric hinderance of the released drug moiety on the site acted on by the degrading enzymes in tumour cells. This document teaches the importance of spacing the peptidic group from the bulky released drug moiety. In contrast, in the present invention, the peptidic group is linked directly to the bulky released drug moiety.

A fifth aspect of the present invention is the compound A:

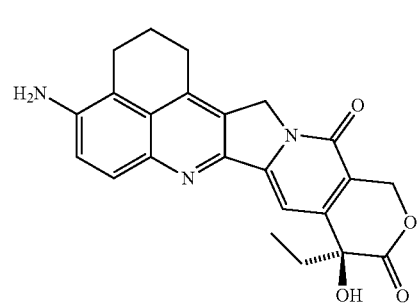

as a single enantiomer or in an enantiomerically enriched form.

A sixth aspect of the present invention is a compound with the formula VI:

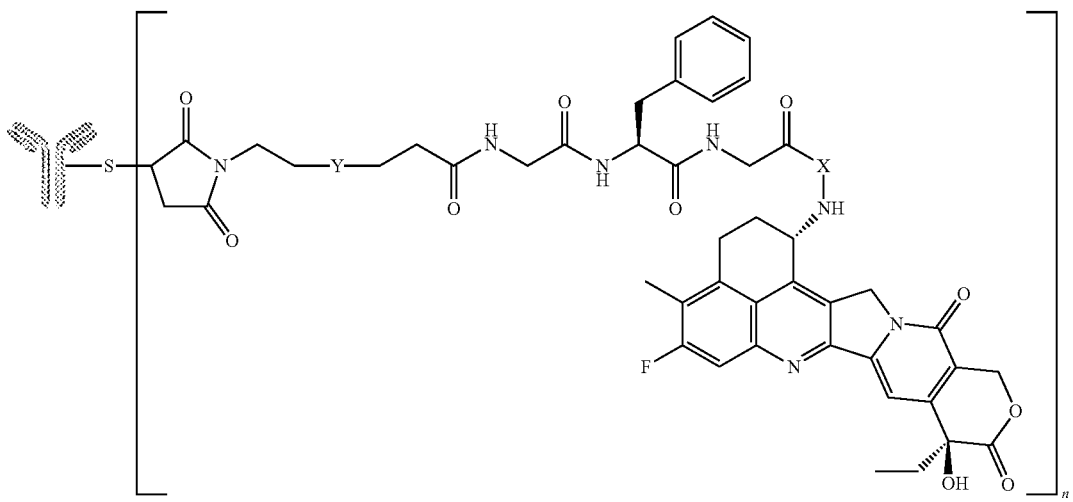

ADC (1): X = none,                      Y = $CH_2$
ADC (2): X = $NH_2$—$CH_2$—(C=O),     Y = $CH_2$
ADC (3): X = $NH_2$—$(CH_2)_2$—(C=O),    Y = $CH_2$
ADC (4): X = $NH_2$—$(CH_2)_3$—(C=O),    Y = $CH_2$
ADC (5): X = $NH_2$—$(CH_2)_4$—(C=O),    Y = $CH_2$
ADC (6): X = $NH_2$—$(CH_2)_5$—(C=O),    Y = $CH_2$
ADC (7): X = $NH_2$—$(CH_2)_3$—(C=O),    Y = (C=O)—NH—$(CH_2CH_3O)_7$
N: DAR

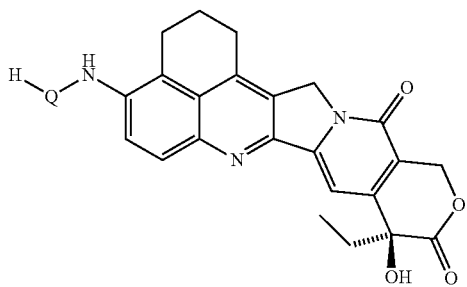

VI where Q is as defined in the first aspect.

Definitions $C_{5-6}$ arylene: The term "$C_{5-6}$ arylene", as used herein, pertains to a divalent moiety obtained by removing two hydrogen atoms from an aromatic ring atom of an aromatic compound.

In this context, the prefixes (e.g. $C_{5-6}$) denote the number of ring atoms, or range of number of ring atoms, whether carbon atoms or heteroatoms.

The ring atoms may be all carbon atoms, as in "carboarylene groups", in which case the group is phenylene ($C_6$).

Alternatively, the ring atoms may include one or more heteroatoms, as in "heteroarylene groups". Examples of heteroarylene groups include, but are not limited to, those derived from:

$N_1$: pyrrole (azole) ($C_5$), pyridine (azine) ($C_6$);
$O_1$: furan (oxole) ($C_5$);
$S_1$: thiophene (thiole) ($C_5$);
$N_1O_1$: oxazole ($C_5$), isoxazole ($C_5$), isoxazine ($C_6$);
$N_2O_1$: oxadiazole (furazan) ($C_5$);
$N_3O_1$: oxatriazole ($C_5$);
$N_1S_1$: thiazole ($C_5$), isothiazole ($C_5$);
$N_2$: imidazole (1,3-diazole) ($C_5$), pyrazole (1,2-diazole) ($C_5$), pyridazine (1,2-diazine) ($C_6$), pyrimidine (1,3-diazine) ($C_6$) (e.g., cytosine, thymine, uracil), pyrazine (1,4-diazine) ($C_6$); and
$N_3$: triazole ($C_5$), triazine ($C_6$).

$C_{1-4}$ alkyl: The term "$C_{1-4}$ alkyl" as used herein, pertains to a monovalent moiety obtained by removing a hydrogen atom from a carbon atom of a hydrocarbon compound having from 1 to 4 carbon atoms, which may be aliphatic or alicyclic, and which may be saturated or unsaturated (e.g. partially unsaturated, fully unsaturated). The term "$C_{1-n}$ alkyl" as used herein, pertains to a monovalent moiety obtained by removing a hydrogen atom from a carbon atom of a hydrocarbon compound having from 1 to n carbon atoms, which may be aliphatic or alicyclic, and which may be saturated or unsaturated (e.g. partially unsaturated, fully unsaturated). Thus, the term "alkyl" includes the sub-classes alkenyl, alkynyl, cycloalkyl, etc., discussed below.

Examples of saturated alkyl groups include, but are not limited to, methyl ($C_1$), ethyl ($C_2$), propyl ($C_3$) and butyl ($C_4$).

Examples of saturated linear alkyl groups include, but are not limited to, methyl ($C_1$), ethyl ($C_2$), n-propyl ($C_3$) and n-butyl ($C_4$).

Examples of saturated branched alkyl groups include iso-propyl ($C_3$), iso-butyl ($C_4$), sec-butyl ($C_4$) and tert-butyl ($C_4$).

$C_{2-4}$ Alkenyl: The term "$C_{2-4}$ alkenyl" as used herein, pertains to an alkyl group having one or more carbon-carbon double bonds.

Examples of unsaturated alkenyl groups include, but are not limited to, ethenyl (vinyl, —CH=CH$_2$), 1-propenyl (—CH=CH—CH$_3$), 2-propenyl (allyl, —CH—CH=CH$_2$), isopropenyl (1-methylvinyl, —C(CH$_3$)=CH$_2$) and butenyl ($C_4$).

$C_{2-4}$ alkynyl: The term "$C_{2-4}$ alkynyl" as used herein, pertains to an alkyl group having one or more carbon-carbon triple bonds.

Examples of unsaturated alkynyl groups include, but are not limited to, ethynyl (—C≡CH) and 2-propynyl (propargyl, —CH$_2$—C≡CH).

$C_{3-4}$ cycloalkyl: The term "$C_{3-4}$ cycloalkyl" as used herein, pertains to an alkyl group which is also a cyclyl group; that is, a monovalent moiety obtained by removing a hydrogen atom from an alicyclic ring atom of a cyclic hydrocarbon (carbocyclic) compound, which moiety has from 3 to 7 carbon atoms, including from 3 to 7 ring atoms.

Examples of cycloalkyl groups include, but are not limited to, those derived from:
saturated monocyclic hydrocarbon compounds:
cyclopropane (C3) and cyclobutane ($C_4$); and
unsaturated monocyclic hydrocarbon compounds:
cyclopropene ($C_3$) and cyclobutene ($C_4$).

Connection labels: In the formula

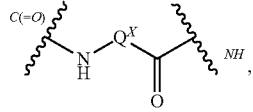

the superscripted labels $^{C(=O)}$ and $^{NH}$ indicate the group to which the atoms are bound. For example, the NH group is shown as being bound to a carbonyl (which is not part of the moiety illustrated), and the carbonyl is shown as being bound to a NH group (which is not part of the moiety illustrated).

Salts

It may be convenient or desirable to prepare, purify, and/or handle a corresponding salt of the active compound, for example, a pharmaceutically-acceptable salt. Examples of pharmaceutically acceptable salts are discussed in Berge, et al., *J. Pharm. Sci.*, 66, 1-19 (1977).

For example, if the compound is anionic, or has a functional group which may be anionic (e.g. —COOH may be —COO$^-$), then a salt may be formed with a suitable cation. Examples of suitable inorganic cations include, but are not limited to, alkali metal ions such as Na$^+$ and K$^+$, alkaline earth cations such as Ca$^{2+}$ and Mg$^{2+}$, and other cations such as Al$^{+3}$. Examples of suitable organic cations include, but are not limited to, ammonium ion (i.e. NH$_4^+$) and substituted ammonium ions (e.g. NH$_3$R$^+$, NH$_2$R$_2^+$, NHR$_3^+$, NR$_4^+$). Examples of some suitable substituted ammonium ions are those derived from: ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine. An example of a common quaternary ammonium ion is N(CH$_3$)$_4^+$.

If the compound is cationic, or has a functional group which may be cationic (e.g. —NH$_2$ may be —NH$_3^+$), then a salt may be formed with a suitable anion. Examples of suitable inorganic anions include, but are not limited to, those derived from the following inorganic acids: hydrochloric, hydrobromic, hydroiodic, sulfuric, sulfurous, nitric, nitrous, phosphoric, and phosphorous.

Examples of suitable organic anions include, but are not limited to, those derived from the following organic acids: 2-acetyoxybenzoic, acetic, ascorbic, aspartic, benzoic, camphorsulfonic, cinnamic, citric, edetic, ethanedisulfonic, ethanesulfonic, fumaric, glucheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, trifluoroacetic acid and valeric. Examples of suitable polymeric organic anions include, but are not limited to, those derived from the following polymeric acids: tannic acid, carboxymethyl cellulose.

Solvates

It may be convenient or desirable to prepare, purify, and/or handle a corresponding solvate of the active compound. The term "solvate" is used herein in the conventional sense to refer to a complex of solute (e.g. active compound, salt of active compound) and solvent. If the solvent is water, the solvate may be conveniently referred to as a hydrate, for example, a mono-hydrate, a di-hydrate, a tri-hydrate, etc.

Isomers

Certain compounds of the invention may exist in one or more particular geometric, optical, enantiomeric, diasteriomeric, epimeric, atropic, stereoisomeric, tautomeric, conformational, or anomeric forms, including but not limited to, cis- and trans-forms; E- and Z-forms; c-, t-, and r-forms; endo- and exo-forms; R-, S-, and meso-forms; D- and L-forms; d- and l-forms; (+) and (−) forms; keto-, enol-, and enolate-forms; syn- and anti-forms; synclinal- and anticlinal-forms; α- and β-forms; axial and equatorial forms; boat-, chair-, twist-, envelope-, and halfchair-forms; and combinations thereof, hereinafter collectively referred to as "isomers" (or "isomeric forms").

The term "chiral" refers to molecules which have the property of non-superimposability of the mirror image partner, while the term "achiral" refers to molecules which are superimposable on their mirror image partner.

The term "stereoisomers" refers to compounds which have identical chemical constitution, but differ with regard to the arrangement of the atoms or groups in space.

"Diastereomer" refers to a stereoisomer with two or more centers of chirality and whose molecules are not mirror images of one another. Diastereomers have different physical properties, e.g. melting points, boiling points, spectral properties, and reactivities. Mixtures of diastereomers may separate under high resolution analytical procedures such as electrophoresis and chromatography.

"Enantiomers" refer to two stereoisomers of a compound which are non-superimposable mirror images of one another.

Stereochemical definitions and conventions used herein generally follow S. P. Parker, Ed., *McGraw-Hill Dictionary of Chemical Terms* (1984) McGraw-Hill Book Company, New York; and Eliel, E. and Wilen, S., "Stereochemistry of Organic Compounds", John Wiley & Sons, Inc., New York, 1994. The compounds of the invention may contain asymmetric or chiral centers, and therefore exist in different stereoisomeric forms. It is intended that all stereoisomeric forms of the compounds of the invention, including but not limited to, diastereomers, enantiomers and atropisomers, as well as mixtures thereof such as racemic mixtures, form part of the present invention. Many organic compounds exist in optically active forms, i.e., they have the ability to rotate the plane of plane-polarized light. In describing an optically active compound, the prefixes D and L, or R and S, are used to denote the absolute configuration of the molecule about its chiral center(s). The prefixes d and l or (+) and (−) are employed to designate the sign of rotation of plane-polarized light by the compound, with (−) or l meaning that the compound is levorotatory. A compound prefixed with (+) or d is dextrorotatory. For a given chemical structure, these stereoisomers are identical except that they are mirror images of one another. A specific stereoisomer may also be referred to as an enantiomer, and a mixture of such isomers is often called an enantiomeric mixture. A 50:50 mixture of enantiomers is referred to as a racemic mixture or a racemate, which may occur where there has been no stereoselection or stereospecificity in a chemical reaction or process. The terms "racemic mixture" and "racemate" refer to an equimolar mixture of two enantiomeric species, devoid of optical activity.

"Enantiomerically enriched form" refers to a sample of a chiral substance whose enantiomeric ratio is greater than 50:50 but less than 100:0.

Note that, except as discussed below for tautomeric forms, specifically excluded from the term "isomers", as used herein, are structural (or constitutional) isomers (i.e. isomers which differ in the connections between atoms rather than merely by the position of atoms in space). For example, a reference to a methoxy group, —OCH$_3$, is not to be construed as a reference to its structural isomer, a hydroxymethyl group, —CH$_2$OH. Similarly, a reference to ortho-chlorophenyl is not to be construed as a reference to its structural isomer, meta-chlorophenyl. However, a reference to a class of structures may well include structurally isomeric forms falling within that class (e.g. C$_{1-7}$ alkyl includes n-propyl and iso-propyl; butyl includes n-, iso-, sec-, and tert-butyl; methoxyphenyl includes ortho-, meta-, and para-methoxyphenyl).

The above exclusion does not pertain to tautomeric forms, for example, keto-, enol-, and enolate-forms, as in, for example, the following tautomeric pairs: keto/enol (illustrated below), imine/enamine, amide/imino alcohol, amidine/enediamine, nitroso/oxime, thioketone/enethiol, N-nitroso/hyroxyazo, and nitro/aci-nitro.

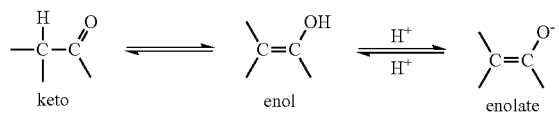

The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. Valence tautomers include interconversions by reorganization of some of the bonding electrons.

Note that specifically included in the term "isomer" are compounds with one or more isotopic substitutions. For example, H may be in any isotopic form, including $^1$H, $^2$H (D), and $^3$H (T); C may be in any isotopic form, including $^{12}$C, $^{13}$C, and $^{14}$C; O may be in any isotopic form, including $^{16}$O and $^{18}$O; and the like.

Examples of isotopes that can be incorporated into compounds of the invention include isotopes of hydrogen, carbon, nitrogen, oxygen, phosphorous, fluorine, chlorine and iodine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, $^{36}$Cl, and $^{125}$I. Various isotopically labeled compounds of the present invention, for example those into which radioactive isotopes such as 3H, 13C, and 14C are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays, or in radioactive treatment of patients. Deuterium labelled or substituted therapeutic compounds of the invention may have improved DMPK (drug metabolism and pharmacokinetics) properties, relating to distribution, metabolism, and excretion (ADME). Substitution with heavier isotopes such as deuterium may afford certain therapeutic advantages resulting from greater metabolic stability, for example increased in vivo half-life or reduced dosage requirements. An 18F labeled compound may be useful for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent. Further, substitution with heavier isotopes, particularly deuterium (i.e., 2H or D) may afford certain therapeutic advantages resulting from greater metabolic stability, for example increased in vivo half-life or reduced dosage requirements or an improvement in therapeutic index. It is understood that deuterium in this context is regarded as a substituent. The concentration of such a heavier isotope, specifically deuterium, may be defined by an isotopic enrichment factor. In the compounds of this invention any atom not specifically designated as a particular isotope is meant to represent any stable isotope of that atom.

Unless otherwise specified, a reference to a particular compound includes all such isomeric forms, including (wholly or partially) racemic and other mixtures thereof. Methods for the preparation (e.g. asymmetric synthesis) and separation (e.g. fractional crystallisation and chromatographic means) of such isomeric forms are either known in the art or are readily obtained by adapting the methods taught herein, or known methods, in a known manner.

Ligand Unit

The Ligand Unit may be of any kind, and include a protein, polypeptide, peptide and a non-peptidic agent that specifically binds to a target molecule. In some embodiments, the Ligand unit may be a protein, polypeptide or peptide. In some embodiments, the Ligand unit may be a cyclic polypeptide. These Ligand units can include antibodies or a fragment of an antibody that contains at least one target molecule-binding site, lymphokines, hormones, growth factors, or any other cell binding molecule or substance that can specifically bind to a target.

The terms "specifically binds" and "specific binding" refer to the binding of an antibody or other protein, polypeptide or peptide to a predetermined molecule (e.g., an antigen). Typically, the antibody or other molecule binds with an affinity of at least about 1×10$^7$ M$^{-1}$, and binds to the predetermined molecule with an affinity that is at least two-fold greater than its affinity for binding to a non-specific molecule (e.g., BSA, casein) other than the predetermined molecule or a closely-related molecule.

Examples of Ligand units include those agents described for use in WO 2007/085930, which is incorporated herein.

In some embodiments, the Ligand unit is a Cell Binding Agent that binds to an extracellular target on a cell. Such a Cell Binding Agent can be a protein, polypeptide, peptide or a non-peptidic agent. In some embodiments, the Cell Binding Agent may be a protein, polypeptide or peptide. In some embodiments, the Cell Binding Agent may be a cyclic polypeptide. The Cell Binding Agent also may be antibody or an antigen-binding fragment of an antibody. Thus, in one embodiment, the present invention provides an antibody-drug conjugate (ADC).

Cell Binding Agent

A cell binding agent may be of any kind, and include peptides and non-peptides. These can include antibodies or a fragment of an antibody that contains at least one binding site, lymphokines, hormones, hormone mimetics, vitamins, growth factors, nutrient-transport molecules, or any other cell binding molecule or substance.

Peptides

In one embodiment, the cell binding agent is a linear or cyclic peptide comprising 4-30, preferably 6-20, contiguous amino acid residues.

In one embodiment the cell binding agent comprises a peptide that binds integrin $\alpha_v\beta_6$. The peptide may be selective for $\alpha_v\beta_6$ over XYS.

In one embodiment the cell binding agent comprises the A20FMDV-Cys polypeptide. The A20FMDV-Cys has the sequence: NAVPNLRGDLQVLAQKVARTC. Alternatively, a variant of the A20FMDV-Cys sequence may be used wherein one, two, three, four, five, six, seven, eight, nine or ten amino acid residues are substituted with another amino acid residue. Furthermore, the polypeptide may have the sequence NAVXXXXXXXXXXXXXXXRTC.

Antibodies

The term "antibody" herein is used in the broadest sense and specifically covers monoclonal antibodies, polyclonal antibodies, dimers, multimers, multispecific antibodies (e.g., bispecific antibodies), multivalent antibodies and antibody fragments, so long as they exhibit the desired biological activity (Miller et al (2003) *Jour. of Immunology* 170:4854-4861). Antibodies may be murine, human, humanized, chimeric, or derived from other species. An antibody is a protein generated by the immune system that is capable of recognizing and binding to a specific antigen. (Janeway, C., Travers, P., Walport, M., Shlomchik (2001) *Immuno Biology*, 5th Ed., Garland Publishing, New York). A target antigen generally has numerous binding sites, also called epitopes, recognized by CDRs on multiple antibodies. Each antibody that specifically binds to a different epitope has a different structure. Thus, one antigen may have more than one corresponding antibody. An antibody includes a full-length immunoglobulin molecule or an immunologically active portion of a full-length immunoglobulin molecule, i.e., a molecule that contains an antigen binding site that immunospecifically binds an antigen of a target of interest or part thereof, such targets including but not limited to, cancer cell or cells that produce autoimmune antibodies associated with an autoimmune disease. The immunoglobulin can be of any type (e.g. IgG, IgE, IgM, IgD, and IgA), class (e.g. IgG1, IgG2, IgG3, IgG4, IgA1 and IgA2) or subclass of immunoglobulin molecule. The immunoglobulins can be derived from any species, including human, murine, or rabbit origin.

"Antibody fragments" comprise a portion of a full length antibody, generally the antigen binding or variable region thereof. Examples of antibody fragments include Fab, Fab', $F(ab')_2$, and scFv fragments; diabodies; linear antibodies; fragments produced by a Fab expression library, anti-idiotypic (anti-Id) antibodies, CDR (complementary determining region), and epitope-binding fragments of any of the above which immunospecifically bind to cancer cell antigens, viral antigens or microbial antigens, single-chain antibody molecules; and multispecific antibodies formed from antibody fragments.

The term "monoclonal antibody" as used herein refers to an antibody obtained from a population of substantially homogeneous antibodies, i.e. the individual antibodies comprising the population are identical except for possible naturally occurring mutations that may be present in minor amounts. Monoclonal antibodies are highly specific, being directed against a single antigenic site. Furthermore, in contrast to polyclonal antibody preparations which include different antibodies directed against different determinants (epitopes), each monoclonal antibody is directed against a single determinant on the antigen. In addition to their specificity, the monoclonal antibodies are advantageous in that they may be synthesized uncontaminated by other antibodies. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by the hybridoma method first described by Kohler et al (1975) Nature 256:495, or may be made by recombinant DNA methods (see, U.S. Pat. No. 4,816,567). The monoclonal antibodies may also be isolated from phage antibody libraries using the techniques described in Clackson et al (1991) Nature, 352:624-628; Marks et al (1991) J. Mol. Biol., 222:581-597 or from transgenic mice carrying a fully human immunoglobulin system (Lonberg (2008) Curr. Opinion 20(4):450-459).

The monoclonal antibodies herein specifically include chimeric antibodies, humanized antibodies and human antibodies.

Examples of cell binding agents include those agents described for use in WO 2007/085930, which is incorporated herein.

Tumour-associate antigens and cognate antibodies for use in embodiments of the present invention are listed below, and are described in more detail on pages 14 to 86 of WO 2017/186894, which is incorporated herein.

(1) BMPR1B (bone morphogenetic protein receptor-type IB)
(2) E16 (LAT1, SLC7A5)
(3) STEAP1 (six transmembrane epithelial antigen of prostate)
(4) 0772P (CA125, MUC16)
(5) MPF (MPF, MSLN, SMR, megakaryocyte potentiating factor, mesothelin)
(6) Napi3b (NAPI-3B, NPTIIb, SLC34A2, solute carrier family 34 (sodium phosphate), member 2, type II sodium-dependent phosphate transporter 3b)
(7) Sema 5b (FLJ10372, KIAA1445, Mm.42015, SEMA5B, SEMAG, Semaphorin 5b Hlog, sema domain, seven thrombospondin repeats (type 1 and type 1-like), transmembrane Domain™ and short cytoplasmic domain, (semaphorin) 5B)
(8) PSCA hlg (2700050C12Rik, C530008O 16Rik, RIKEN cDNA 2700050C12, RIKEN cDNA 2700050C12 gene)
(9) ETBR (Endothelin type B receptor)
(10) MSG783 (RNF124, hypothetical protein FLJ20315)
(11) STEAP2 (HGNC_8639, IPCA-1, PCANAP1, STAMP1, STEAP2, STMP, prostate cancer associated gene 1, prostate cancer associated protein 1, six transmembrane epithelial antigen of prostate 2, six transmembrane prostate protein)
(12) TrpM4 (BR22450, FLJ20041, TRPM4, TRPM4B, transient receptor potential cation 5 channel, subfamily M, member 4)
(13) CRIPTO (CR, CR1, CRGF, CRIPTO, TDGF1, teratocarcinoma-derived growth factor)
(14) CD21 (CR2 (Complement receptor 2) or C3DR (C3d/Epstein Barr virus receptor) or Hs.73792)
(15) CD79b (CD79B, CD79p, IGb (immunoglobulin-associated beta), B29)
(16) FcRH2 (IFGP4, IRTA4, SPAP1A (SH2 domain containing phosphatase anchor protein 1a), SPAP1B, SPAP1C)
(17) HER2 (ErbB2)
(18) NCA (CEACAM6)
(19) MDP (DPEP1)
(20) IL20R-alpha (IL20Ra, ZCYTOR7)
(21) Brevican (BCAN, BEHAB)
(22) EphB2R (DRT, ERK, Hek5, EPHT3, Tyro5)
(23) ASLG659 (B7h)
(24) PSCA (Prostate stem cell antigen precursor)
(25) GEDA
(26) BAFF-R (B cell-activating factor receptor, BLyS receptor 3, BR3)
(27) CD22 (B-cell receptor CD22-B isoform, BL-CAM, Lyb-8, Lyb8, SIGLEC-2, FLJ22814)
(27a) CD22 (CD22 molecule)
(28) CD79a (CD79A, CD79alpha), immunoglobulin-associated alpha, a B cell-specific protein that covalently interacts with Ig beta (CD79B) and forms a complex on the surface with Ig M molecules, transduces a signal involved in B-cell differentiation), pI: 4.84, MW: 25028 TM: 2 [P] Gene Chromosome: 19q13.2).
(29) CXCR5 (Burkitt's lymphoma receptor 1, a G protein-coupled receptor that is activated by the CXCL13 chemokine, functions in lymphocyte migration and humoral defense, plays a role in HIV-2 infection and perhaps development of AIDS, lymphoma, myeloma, and leukemia); 372 aa, pI: 8.54 MW: 41959 TM: 7 [P] Gene Chromosome: 11q23.3,
(30) HLA-DOB (Beta subunit of MHC class II molecule (Ia antigen) that binds peptides and presents them to CD4+T lymphocytes); 273 aa, pI: 6.56, MW: 30820.TM: 1 [P] Gene Chromosome: 6p21.3)
(31) P2X5 (Purinergic receptor P2X ligand-gated ion channel 5, an ion channel gated by extracellular ATP, may be involved in synaptic transmission and neurogenesis, deficiency may contribute to the pathophysiology of idiopathic detrusor instability); 422 aa), pI: 7.63, MW: 47206 TM: 1 [P] Gene Chromosome: 17p13.3).
(32) CD72 (B-cell differentiation antigen CD72, Lyb-2); 359 aa, pI: 8.66, MW: 40225, TM: 1 5 [P] Gene Chromosome: 9p13.3).
(33) LY64 (Lymphocyte antigen 64 (RP105), type I membrane protein of the leucine rich repeat (LRR) family, regulates B-cell activation and apoptosis, loss of function is associated with increased disease activity in patients with systemic lupus erythematosis); 661 aa, pI: 6.20, MW: 74147 TM: 1 [P] Gene Chromosome: 5q12).
(34) FcRH1 (Fc receptor-like protein 1, a putative receptor for the immunoglobulin Fc domain that contains C2 type Ig-like and ITAM domains, may have a role in B-lymphocyte differentiation); 429 aa, pI: 5.28, MW: 46925 TM: 1 [P] Gene Chromosome: 1q21-1q22).
(35) IRTA2 (Immunoglobulin superfamily receptor translocation associated 2, a putative immunoreceptor with possible roles in B cell development and lymphomagenesis; deregulation of the gene by translocation occurs in some B cell malignancies); 977 aa, pI: 6.88, MW: 106468, TM: 1 [P] Gene Chromosome: 1q21)

(36) TENB2 (TMEFF2, tomoregulin, TPEF, HPP1, TR, putative transmembrane proteoglycan, related to the EGF/ heregulin family of growth factors and follistatin); 374 aa)

(37) PSMA-FOLH1 (Folate hydrolase (prostate-specific membrane antigen) 1)

(38) SST (Somatostatin Receptor; note that there are 5 subtypes)

(38.1) SSTR2 (Somatostatin receptor 2)

(38.2) SSTR5 (Somatostatin receptor 5)

(38.3) SSTR1

(38.4) SSTR3

(38.5) SSTR4

AvB6—Both subunits (39+40)

(39) ITGAV (Integrin, alpha V)

(40) ITGB6 (Integrin, beta 6)

(41) CEACAM5 (Carcinoembryonic antigen-related cell adhesion molecule 5)

(42) MET (met proto-oncogene; hepatocyte growth factor receptor)

(43) MUC1 (Mucin 1, cell surface associated)

(44) CA9 (Carbonic anhydrase IX)

(45) EGFRvIII (Epidermal growth factor receptor (EGFR), transcript variant 3,

(46) CD33 (CD33 molecule)

(47) CD19 (CD19 molecule)

(48) IL2RA (Interleukin 2 receptor, alpha); NCBI Reference Sequence: NM_000417.2);

(49) AXL (AXL receptor tyrosine kinase)

(50) CD30—TNFRSF8 (Tumor necrosis factor receptor superfamily, member 8)

(51) BCMA (B-cell maturation antigen)—TNFRSF17 (Tumor necrosis factor receptor superfamily, member 17)

(52) CT Ags-CTA (Cancer Testis Antigens)

(53) CD174 (Lewis Y)-FUT3 (fucosyltransferase 3 (galactoside 3(4)-L-fucosyltransferase, Lewis blood group)

(54) CLEC14A (C-type lectin domain family 14, member A; Genbank accession no. NM175060)

(55) GRP78—HSPA5 (heat shock 70 kDa protein 5 (glucose-regulated protein, 78 kDa)

(56) CD70 (CD70 molecule) L08096

(57) Stem Cell specific antigens. For example:

5T4 (see entry (63) below)

CD25 (see entry (48) above)

CD32

LGR5/GPR49

Prominin/CD133

(58) ASG-5

(59) ENPP3 (Ectonucleotide pyrophosphatase/phosphodiesterase 3)

(60) PRR4 (Proline rich 4 (lacrimal))

(61) GCC-GUCY2C (guanylate cyclase 2C (heat stable enterotoxin receptor)

(62) Liv-1—SLC39A6 (Solute carrier family 39 (zinc transporter), member 6)

(63) 5T4, Trophoblast glycoprotein, TPBG-TPBG (trophoblast glycoprotein)

(64) CD56—NCMA1 (Neural cell adhesion molecule 1)

(65) CanAg (Tumor associated antigen CA242)

(66) FOLR1 (Folate Receptor 1)

(67) GPNMB (Glycoprotein (transmembrane) nmb)

(68) TIM-1—HAVCR1 (Hepatitis A virus cellular receptor 1)

(69) RG-1/Prostate tumor target Mindin-Mindin/RG-1

(70) B7-H4—VTCN1 (V-set domain containing T cell activation inhibitor 1

(71) PTK7 (PTK7 protein tyrosine kinase 7)

(72) CD37 (CD37 molecule)

(73) CD138—SDC1 (syndecan 1)

(74) CD74 (CD74 molecule, major histocompatibility complex, class II invariant chain)

(75) Claudins-CLs (Claudins)

(76) EGFR (Epidermal growth factor receptor)

(77) Her3 (ErbB3)-ERBB3 (v-erb-b2 erythroblastic leukemia viral oncogene homolog 3 (avian))

(78) RON-MST1R (macrophage stimulating 1 receptor (c-met-related tyrosine kinase))

(79) EPHA2 (EPH receptor A2)

(80) CD20—MS4A1 (membrane-spanning 4-domains, subfamily A, member 1)

(81) Tenascin C-TNC (Tenascin C)

(82) FAP (Fibroblast activation protein, alpha)

(83) DKK-1 (Dickkopf 1 homolog (*Xenopus laevis*)

(84) CD52 (CD52 molecule)

(85) CS1—SLAMF7 (SLAM family member 7)

(86) Endoglin-ENG (Endoglin)

(87) Annexin A1—ANXA1 (Annexin A1)

(88) V-CAM (CD106)-VCAM1 (Vascular cell adhesion molecule 1)

An additional tumour-associate antigen and cognate antibodies of interest are:

(89) ASCT2 (ASC transporter 2, also known as SLC1A5).

ASCT2 antibodies are described in WO 2018/089393, which is incorporated herein by reference The cell binding agent may be labelled, for example to aid detection or purification of the agent either prior to incorporation as a conjugate, or as part of the conjugate. The label may be a biotin label. In another embodiment, the cell binding agent may be labelled with a radioisotope.

Methods of Treatment

The conjugates of the present invention may be used in a method of therapy. Also provided is a method of treatment, comprising administering to a subject in need of treatment a therapeutically-effective amount of a conjugate of formula IV. The term "therapeutically effective amount" is an amount sufficient to show benefit to a patient. Such benefit may be at least amelioration of at least one symptom. The actual amount administered, and rate and time-course of administration, will depend on the nature and severity of what is being treated. Prescription of treatment, e.g. decisions on dosage, is within the responsibility of general practitioners and other medical doctors.

A conjugate may be administered alone or in combination with other treatments, either simultaneously or sequentially dependent upon the condition to be treated. Examples of treatments and therapies include, but are not limited to, chemotherapy (the administration of active agents, including, e.g. drugs); surgery; and radiation therapy.

Pharmaceutical compositions according to the present invention, and for use in accordance with the present invention, may comprise, in addition to the active ingredient, i.e. a conjugate of formula IV, a pharmaceutically acceptable excipient, carrier, buffer, stabiliser or other materials well known to those skilled in the art. Such materials should be non-toxic and should not interfere with the efficacy of the active ingredient. The precise nature of the carrier or other material will depend on the route of administration, which may be oral, or by injection, e.g. cutaneous, subcutaneous, or intravenous.

Pharmaceutical compositions for oral administration may be in tablet, capsule, powder or liquid form. A tablet may comprise a solid carrier or an adjuvant. Liquid pharmaceutical compositions generally comprise a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included. A capsule may comprise a solid carrier such a gelatin.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers, antioxidants and/or other additives may be included, as required.

The Conjugates can be used to treat proliferative disease and autoimmune disease. The term "proliferative disease" pertains to an unwanted or uncontrolled cellular proliferation of excessive or abnormal cells which is undesired, such as, neoplastic or hyperplastic growth, whether in vitro or in vivo.

Examples of proliferative conditions include, but are not limited to, benign, pre-malignant, and malignant cellular proliferation, including but not limited to, neoplasms and tumours (e.g., histocytoma, glioma, astrocyoma, osteoma), cancers (e.g. lung cancer, small cell lung cancer, gastrointestinal cancer, bowel cancer, colon cancer, breast carcinoma, ovarian carcinoma, prostate cancer, testicular cancer, liver cancer, kidney cancer, bladder cancer, pancreatic cancer, brain cancer, sarcoma, osteosarcoma, Kaposi's sarcoma, melanoma), leukemias, psoriasis, bone diseases, fibroproliferative disorders (e.g. of connective tissues), and atherosclerosis. Other cancers of interest include, but are not limited to, haematological; malignancies such as leukemias and lymphomas, such as non-Hodgkin lymphoma, and subtypes such as DLBCL, marginal zone, mantle zone, and follicular, Hodgkin lymphoma, AML, and other cancers of B or T cell origin. Any type of cell may be treated, including but not limited to, lung, gastrointestinal (including, e.g. bowel, colon), breast (mammary), ovarian, prostate, liver (hepatic), kidney (renal), bladder, pancreas, brain, and skin.

Examples of autoimmune disease include the following: rheumatoid arthritis, autoimmune demyelinative diseases (e.g., multiple sclerosis, allergic encephalomyelitis), psoriatic arthritis, endocrine ophthalmopathy, uveoretinitis, systemic lupus erythematosus, myasthenia gravis, Graves' disease, glomerulonephritis, autoimmune hepatological disorder, inflammatory bowel disease (e.g., Crohn's disease), anaphylaxis, allergic reaction, Sjögren's syndrome, type I diabetes mellitus, primary biliary cirrhosis, Wegener's granulomatosis, fibromyalgia, polymyositis, dermatomyositis, multiple endocrine failure, Schmidt's syndrome, autoimmune uveitis, Addison's disease, adrenalitis, thyroiditis, Hashimoto's thyroiditis, autoimmune thyroid disease, pernicious anemia, gastric atrophy, chronic hepatitis, lupoid hepatitis, atherosclerosis, subacute cutaneous lupus erythematosus, hypoparathyroidism, Dressler's syndrome, autoimmune thrombocytopenia, idiopathic thrombocytopenic purpura, hemolytic anemia, pemphigus vulgaris, pemphigus, dermatitis herpetiformis, alopecia arcata, pemphigoid, scleroderma, progressive systemic sclerosis, CREST syndrome (calcinosis, Raynaud's phenomenon, esophageal dysmotility, sclerodactyly, and telangiectasia), male and female autoimmune infertility, ankylosing spondolytis, ulcerative colitis, mixed connective tissue disease, polyarteritis nedosa, systemic necrotizing vasculitis, atopic dermatitis, atopic rhinitis, Goodpasture's syndrome, Chagas' disease, sarcoidosis, rheumatic fever, asthma, recurrent abortion, antiphospholipid syndrome, farmer's lung, erythema multiforme, post cardiotomy syndrome, Cushing's syndrome, autoimmune chronic active hepatitis, bird-fancier's lung, toxic epidermal necrolysis, Alport's syndrome, alveolitis, allergic alveolitis, fibrosing alveolitis, interstitial lung disease, erythema nodosum, pyoderma gangrenosum, transfusion reaction, Takayasu's arteritis, polymyalgia rheumatica, temporal arteritis, schistosomiasis, giant cell arteritis, ascariasis, aspergillosis, Sampter's syndrome, eczema, lymphomatoid granulomatosis, Behcet's disease, Caplan's syndrome, Kawasaki's disease, dengue, encephalomyelitis, endocarditis, endomyocardial fibrosis, endophthalmitis, erythema elevatum et diutinum, psoriasis, erythroblastosis fetalis, eosinophilic faciitis, Shulman's syndrome, Felty's syndrome, filariasis, cyclitis, chronic cyclitis, heterochronic cyclitis, Fuch's cyclitis, IgA nephropathy, Henoch-Schonlein purpura, graft versus host disease, transplantation rejection, cardiomyopathy, Eaton-Lambert syndrome, relapsing polychondritis, cryoglobulinemia, Waldenstrom's macroglobulemia, Evan's syndrome, and autoimmune gonadal failure.

In some embodiments, the autoimmune disease is a disorder of B lymphocytes (e.g., systemic lupus erythematosus, Goodpasture's syndrome, rheumatoid arthritis, and type I diabetes), Th1-lymphocytes (e.g., rheumatoid arthritis, multiple sclerosis, psoriasis, Sjögren's syndrome, Hashimoto's thyroiditis, Graves' disease, primary biliary cirrhosis, Wegener's granulomatosis, tuberculosis, or graft versus host disease), or Th2-lymphocytes (e.g., atopic dermatitis, systemic lupus erythematosus, atopic asthma, rhinoconjunctivitis, allergic rhinitis, Omenn's syndrome, systemic sclerosis, or chronic graft versus host disease). Generally, disorders involving dendritic cells involve disorders of Th1-lymphocytes or Th2-lymphocytes. In some embodiments, the autoimmunie disorder is a T cell-mediated immunological disorder.

A "chemotherapeutic agent" is a chemical compound useful in the treatment of cancer, regardless of mechanism of action. Classes of chemotherapeutic agents include, but are not limited to: alkylating agents, antimetabolites, spindle poison plant alkaloids, cytotoxic/antitumor antibiotics, topoisomerase inhibitors, antibodies, photosensitizers, and kinase inhibitors. Chemotherapeutic agents include compounds used in "targeted therapy" and conventional chemotherapy.

Examples of chemotherapeutic agents include: erlotinib (TARCEVA@, Genentech/OSI Pharm.), docetaxel (TAXOTERE@, Sanofi-Aventis), 5-FU (fluorouracil, 5-fluorouracil, CAS No. 51-21-8), gemcitabine (GEMZAR®, Lilly), PD-0325901 (CAS No. 391210-10-9, Pfizer), cisplatin (cis-diamine, dichloroplatinum(II), CAS No. 15663-27-1), carboplatin (CAS No. 41575-94-4), paclitaxel (TAXOL@, Bristol-Myers Squibb Oncology, Princeton, N.J.), trastuzumab (HERCEPTIN@, Genentech), temozolomide (4-methyl-5-oxo-2,3,4,6,8-pentazabicyclo [4.3.0] nona-2,7, 9-triene-9-carboxamide, CAS No. 85622-93-1, TEMODAR®, TEMODAL@, Schering Plough), tamoxifen ((Z)-2-[4-(1,2-diphenylbut-1-enyl)phenoxy]-N,N-dimethylethanamine, NOLVADEX®, ISTUBAL®, VALODEX®), and doxorubicin (ADRIAMYCIN®), Akti-1/2, HPPD, and rapamycin.

More examples of chemotherapeutic agents include: oxaliplatin (ELOXATIN®, Sanofi), bortezomib (VELCADE®, Millennium Pharm.), sutent (SUNITINIB®, SU 1248, Pfizer), letrozole (FEMARA®, Novartis), imatinib mesylate (GLEEVEC®, Novartis), XL-518 (Mek inhibitor, Exelixis, WO 2007/044515), ARRY-886 (Mek inhibitor, AZD6244, Array BioPharma, Astra Zeneca), SF-1126 (PI3K inhibitor, Semafore Pharmaceuticals), BEZ-235 (PI3K inhibitor, Novartis), XL-147 (PI3K inhibitor, Exelixis), PTK787/ZK 222584 (Novartis), fulvestrant (FASLODEX®, AstraZeneca), leucovorin (folinic acid), rapamycin (sirolimus, RAPAMUNE®, Wyeth), lapatinib (TYKERB®, GSK572016, Glaxo Smith Kline), lonafarnib (SARASAR™, SCH 66336, Schering Plough), sorafenib (NEXAVAR@, BAY43-9006, Bayer Labs), gefitinib (IRESSA®, AstraZeneca), irinotecan (CAMPTOSAR®, CPT-11, Pfizer), tipifarnib (ZARNESTRA™, Johnson & Johnson), ABRAXANE™ (Cremophor-free), albumin-engineered nanoparticle formulations of paclitaxel (American Pharmaceutical Partners, Schaumberg, II), vandetanib (rINN, ZD6474, ZACTIMA®, AstraZeneca), chloranmbucil, AG1478, AG1571 (SU 5271; Sugen), temsirolimus (TORISEL®, Wyeth), pazopanib (GlaxoSmithKline), canfosfamide (TELCYTA®, Telik), thiotepa and cyclosphosphamide (CYTOXAN@, NEOSAR®); alkyl sulfonates such as busulfan, improsulfan and piposulfan; aziridines such as benzodopa, carboquone, meturedopa, and uredopa; ethylenimines and methylamelamines including altretamine, triethylenemelamine, triethylenephosphoramide, triethylenethiophosphoramide and trimethylomelamine; acetogenins (especially bullatacin and bullatacinone); a camptothecin (including the synthetic analog topotecan); bryostatin; callystatin; CC-1065 (including its adozelesin, carzelesin and bizelesin synthetic analogs); cryptophycins (particularly cryptophycin 1 and cryptophycin 8); dolastatin; duocarmycin (including the synthetic analogs, KW-2189 and CB1-TM1); eleutherobin; pancratistatin; a sarcodictyin; spongistatin; nitrogen mustards such as chlorambucil, chlornaphazine, chlorophosphamide, estramustine, ifosfamide, mechlorethamine, mechlorethamine oxide hydrochloride, melphalan, novembichin, phenesterine, prednimustine, trofosfamide, uracil mustard; nitrosoureas such as carmustine, chlorozotocin, fotemustine, lomustine, nimustine, and ranimnustine; antibiotics such as the enediyne antibiotics (e.g. calicheamicin, calicheamicin gamma1I, calicheamicin omega1I (Angew Chem. Intl. Ed. Engl. (1994) 33:183-186); dynemicin, dynemicin A; bisphosphonates, such as clodronate; an esperamicin; as well as neocarzinostatin chromophore and related chromoprotein enediyne antibiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, morpholino-doxorubicin, cyanomorpholino-doxorubicin, 2-pyrrolino-doxorubicin and deoxydoxorubicin), epirubicin, esorubicin, idarubicin, nemorubicin, marcellomycin, mitomycins such as mitomycin C, mycophenolic acid, nogalamycin, olivomycins, peplomycin, porfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogs such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elfornithine; elliptinium acetate; an epothilone; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; podophyllinic acid; 2-ethylhydrazide; procarbazine; PSK@ polysaccharide complex (JHS Natural Products, Eugene, Oreg.); razoxane; rhizoxin; sizofiran; spirogermanium; tenuazonic acid; triaziquone; 2,2',2"-trichlorotriethylamine; trichothecenes (especially T-2 toxin, verracurin A, roridin A and anguidine); urethan; vindesine; dacarbazine; mannomustine; mitobronitol; mitolactol; pipobroman; gacytosine; arabinoside ("Ara-C"); cyclophosphamide; thiotepa; 6-thioguanine; mercaptopurine; methotrexate; platinum analogs such as cisplatin and carboplatin; vinblastine; etoposide (VP-16); ifosfamide; mitoxantrone; vincristine; vinorelbine (NAVELBINE®); novantrone; teniposide; edatrexate; daunomycin; aminopterin; capecitabine (XELODA®, Roche); ibandronate; CPT-11; topoisomerase inhibitor RFS 2000; difluoromethylornithine (DMFO); retinoids such as retinoic acid; and pharmaceutically acceptable salts, acids and derivatives of any of the above.

Also included in the definition of "chemotherapeutic agent" are: (i) anti-hormonal agents that act to regulate or inhibit hormone action on tumors such as anti-estrogens and selective estrogen receptor modulators (SERMs), including, for example, tamoxifen (including NOLVADEX®; tamoxifen citrate), raloxifene, droloxifene, 4-hydroxytamoxifen, trioxifene, keoxifene, LY117018, onapristone, and FARESTON® (toremifine citrate); (ii) aromatase inhibitors that inhibit the enzyme aromatase, which regulates estrogen production in the adrenal glands, such as, for example, 4(5)-imidazoles, aminoglutethimide, MEGASE® (megestrol acetate), AROMASIN® (exemestane; Pfizer), formestanie, fadrozole, RIVISOR® (vorozole), FEMARA® (letrozole; Novartis), and ARIMIDEX® (anastrozole; AstraZeneca); (iii) anti-androgens such as flutamide, nilutamide, bicalutamide, leuprolide, and goserelin; as well as troxacitabine (a 1,3-dioxolane nucleoside cytosine analog); (iv) protein kinase inhibitors such as MEK inhibitors (WO 2007/044515); (v) lipid kinase inhibitors; (vi) antisense oligonucleotides, particularly those which inhibit expression of genes in signaling pathways implicated in aberrant cell proliferation, for example, PKC-alpha, Raf and H-Ras, such as oblimersen (GENASENSE®, Genta Inc.); (vii) ribozymes such as VEGF expression inhibitors (e.g., ANGIOZYME®) and HER2 expression inhibitors; (viii) vaccines such as gene therapy vaccines, for example, ALLOVECTIN®, LEUVECTIN®, and VAXID®; PROLEUKIN® rIL-2; topoisomerase 1 inhibitors such as LURTOTECAN®; ABARELIX® rmRH; (ix) anti-angiogenic agents such as bevacizumab (AVASTIN®, Genentech); and pharmaceutically acceptable salts, acids and derivatives of any of the above.

Also included in the definition of "chemotherapeutic agent" are therapeutic antibodies such as alemtuzumab (Campath), bevacizumab (AVASTIN®, Genentech); cetuximab (ERBITUX®, Imclone); panitumumab (VECTIBIX®, Amgen), rituximab (RITUXAN®, Genentech/Biogen Idec), pertuzumab (OMNITARG™, 2C4, Genentech), trastuzumab (HERCEPTIN®, Genentech), tositumomab (Bexxar, Corixia), and the antibody drug conjugate, gemtuzumab ozogamicin (MYLOTARG@, Wyeth).

Humanized monoclonal antibodies with therapeutic potential as chemotherapeutic agents in combination with the conjugates of the invention include: alemtuzumab, apolizumab, aselizumab, atlizumab, bapineuzumab, bevacizumab, bivatuzumab mertansine, cantuzumab mertansine, cedelizumab, certolizumab pegol, cidfusituzumab, cidtuzumab, daclizumab, eculizumab, efalizumab, epratuzumab, erlizumab, felvizumab, fontolizumab, gemtuzumab ozogamicin, inotuzumab ozogamicin, ipilimumab, labetuzumab, lintuzumab, matuzumab, mepolizumab, motavizumab, motovizumab, natalizumab, nimotuzumab, nolovizumab, numavizumab, ocrelizumab, omalizumab, palivizumab, pascolizumab, pecfusituzumab, pectuzumab, pertuzumab, pexelizumab, ralivizumab, ranibizumab, reslivizumab, reslizumab, resyvizumab, rovelizumab, ruplizumab, sibrotuzumab, siplizumab, sontuzumab, tacatuzumab tetraxetan, tadocizumab, talizumab, tefibazumab, tocilizumab, toralizumab, trastuzumab, tucotuzumab celmoleukin, tucusituzumab, umavizumab, urtoxazumab, and visilizumab.

Formulations

While it is possible for the conjugate to be used (e.g., administered) alone, it is often preferable to present it as a composition or formulation.

In one embodiment, the composition is a pharmaceutical composition (e.g., formulation, preparation, medicament) comprising a conjugate, as described herein, and a pharmaceutically acceptable carrier, diluent, or excipient.

In one embodiment, the composition is a pharmaceutical composition comprising at least one conjugate, as described herein, together with one or more other pharmaceutically acceptable ingredients well known to those skilled in the art, including, but not limited to, pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents.

In one embodiment, the composition further comprises other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Remington's Pharmaceutical Sciences,* 20th edition, pub. Lippincott, Williams & Wilkins, 2000; and *Handbook of Pharmaceutical Excipients,* 2nd edition, 1994.

Another aspect of the present invention pertains to methods of making a pharmaceutical composition comprising admixing at least one [$^{11}$C]-radiolabelled conjugate or conjugate-like compound, as defined herein, together with one or more other pharmaceutically acceptable ingredients well known to those skilled in the art, e.g., carriers, diluents, excipients, etc. If formulated as discrete units (e.g., tablets, etc.), each unit contains a predetermined amount (dosage) of the active compound.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the active compound with a carrier which constitutes one or more accessory ingredients. In general, the formulations are prepared by uniformly and intimately bringing into association the active compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for parenteral administration (e.g., by injection), include aqueous or non-aqueous, isotonic, pyrogen-free, sterile liquids (e.g., solutions, suspensions), in which the active ingredient is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the active ingredient in the liquid is from about 1 ng/ml to about 10 µg/ml, for example from about 10 ng/ml to about 1 µg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the Conjugates, and compositions comprising the Conjugates, can vary from patient to patient. Determining the optimal dosage will generally involve the balancing of the level of therapeutic benefit against any risk or deleterious side effects. The selected dosage level will depend on a variety of factors including, but not limited to, the activity of the particular compound, the route of administration, the time of administration, the rate of excretion of the compound, the duration of the treatment, other drugs, compounds, and/or materials used in combination, the severity of the condition, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

In general, a suitable dose of the active compound is in the range of about 100 ng to about 25 mg (more typically about 1 µg to about 10 mg) per kilogram body weight of the subject per day. Where the active compound is a salt, an ester, an amide, a prodrug, or the like, the amount administered is calculated on the basis of the parent compound and so the actual weight to be used is increased proportionately.

The dosage amounts described above may apply to the conjugate or to the effective amount of compound that is releasable after cleavage of the linker.

For the prevention or treatment of disease, the appropriate dosage of an ADC of the invention will depend on the type of disease to be treated, as defined above, the severity and course of the disease, whether the molecule is administered for preventive or therapeutic purposes, previous therapy, the patient's clinical history and response to the antibody, and the discretion of the attending physician. The molecule is suitably administered to the patient at one time or over a series of treatments. Depending on the type and severity of the disease, about 1 µg/kg to 100 mg/kg or more of molecule is an initial candidate dosage for administration to the patient, whether, for example, by one or more separate administrations, or by continuous infusion. For repeated administrations over several days or longer, depending on the condition, the treatment is sustained until a desired suppression of disease symptoms occurs. Other dosage regimens may be useful. The progress of this therapy is easily monitored by conventional techniques and assays.

Drug Loading

The drug loading (p) is the average number of drugs per Ligand unit, which may be a cell binding agent, e.g. antibody.

The average number of drugs per antibody in preparations of ADC from conjugation reactions may be characterized by conventional means such as UV, reverse phase HPLC, HIC, mass spectroscopy, ELISA assay, and electrophoresis. The quantitative distribution of ADC in terms of p may also be determined. By ELISA, the averaged value of p in a particular preparation of ADC may be determined (Hamblett et al (2004) Clin. Cancer Res. 10:7063-7070; Sanderson et al (2005) Clin. Cancer Res. 11:843-852). However, the distribution of p (drug) values is not discernible by the antibody-antigen binding and detection limitation of ELISA. Also, ELISA assay for detection of antibody-drug conjugates does not determine where the drug moieties are attached to the antibody, such as the heavy chain or light chain fragments, or the particular amino acid residues. In some instances, separation, purification, and characterization of homogeneous ADC where p is a certain value from ADC with other drug loadings may be achieved by means such as reverse phase HPLC or electrophoresis. Such techniques are also applicable to other types of conjugates. For some antibody-drug conjugates, p may be limited by the number of attachment sites on the antibody. For example, an antibody may have only one or several cysteine thiol groups, or may have only one or several sufficiently reactive thiol groups through which a linker may be attached. Higher drug loading may cause aggregation, insolubility, toxicity, or loss of cellular permeability of certain antibody-drug conjugates.

Typically, fewer than the theoretical maximum of drug moieties are conjugated to an antibody during a conjugation reaction. An antibody may contain, for example, many lysine residues that do not react with the Drug Linker. Only the most reactive lysine groups may react with an amine-reactive linker reagent. Also, only the most reactive cysteine thiol groups may react with a thiol-reactive linker reagent. Generally, antibodies do not contain many, if any, free and reactive cysteine thiol groups which may be linked to a drug moiety. Most cysteine thiol residues in the antibodies of the compounds exist as disulfide bridges and must be reduced with a reducing agent such as dithiothreitol (DTT) or TCEP, under partial or total reducing conditions. The loading (drug/antibody ratio) of an ADC may be controlled in several different manners, including: (i) limiting the molar excess of Drug Linker relative to antibody, (ii) limiting the conjugation reaction time or temperature, and (iii) partial or limiting reductive conditions for cysteine thiol modification.

Certain antibodies have reducible interchain disulfides, i.e. cysteine bridges. Antibodies may be made reactive for conjugation with linker reagents by treatment with a reducing agent such as DTT (dithiothreitol). Each cysteine bridge will thus form, theoretically, two reactive thiol nucleophiles. Additional nucleophilic groups can be introduced into antibodies through the reaction of lysines with 2-iminothiolane (Traut's reagent) resulting in conversion of an amine into a thiol. Reactive thiol groups may be introduced into the antibody (or fragment thereof) by engineering one, two, three, four, or more cysteine residues (e.g., preparing mutant antibodies comprising one or more non-native cysteine amino acid residues). U.S. Pat. No. 7,521,541 teaches engineering antibodies by introduction of reactive cysteine amino acids.

Cysteine amino acids may be engineered at reactive sites in an antibody and which do not form intrachain or intermolecular disulfide linkages (Junutula, et al., 2008b Nature Biotech., 26(8):925-932; Dornan et al (2009) Blood 114 (13):2721-2729; U.S. Pat. Nos. 7,521,541; 7,723,485; WO2009/052249). The engineered cysteine thiols may react with Drug Linkers of the present invention (i.e. of formula I) which have thiol-reactive, electrophilic groups such as maleimide or alpha-halo amides to form ADC with cysteine engineered antibodies. The location of the drug unit can thus be designed, controlled, and known. The drug loading can be controlled since the engineered cysteine thiol groups typically react with drug-linker reagents in high yield. Engineering an IgG antibody to introduce a cysteine amino acid by substitution at a single site on the heavy or light chain gives two new cysteines on the symmetrical antibody. A drug loading near 2 can be achieved with near homogeneity of the conjugation product ADC.

Where more than one nucleophilic or electrophilic group of the antibody reacts with Drug Linkers, then the resulting product may be a mixture of ADC compounds with a distribution of drug units attached to an antibody, e.g. 1, 2, 3, etc. Liquid chromatography methods such as polymeric reverse phase (PLRP) and hydrophobic interaction (HIC) may separate compounds in the mixture by drug loading value. Preparations of ADC with a single drug loading value (p) may be isolated, however, these single loading value ADCs may still be heterogeneous mixtures because the drug units may be attached, via the linker, at different sites on the antibody.

Thus the antibody-drug conjugate compositions of the invention may include mixtures of antibody-drug conjugates where the antibody has one or more drug moieties and where the drug moieties may be attached to the antibody at various amino acid residues.

In one embodiment, the average number of drugs per cell binding agent is in the range 1 to 20. In some embodiments the range is selected from 1 to 10, 2 to 10, 2 to 8, 2 to 6, and 4 to 10.

In some embodiments, there is one drug per cell binding agent.

General Synthetic Routes

Compounds of formula I where $R^L$ is of formula Ia may be synthesised from a compound of Formula 2:

Formula 2

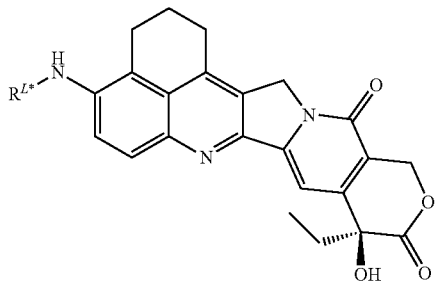

where $R^{L*}$ is -QH by linking a compound of Formula 3:

Formula 3

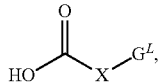

or an activated version thereof.

Such a reaction may be carried out under amide coupling conditions.

Compounds of Formula 2 may be synthesised by the deprotection of a compound of Formula 4:

Formula 4

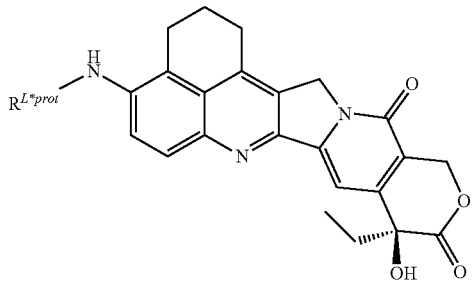

where $R^{L*prot}$ is -Q-Prot$^N$, where Prot$^N$ is an amine protecting group.

Compounds of Formula 4 may be synthesised by the coupling of a compound of Formula 5:

Formula 5

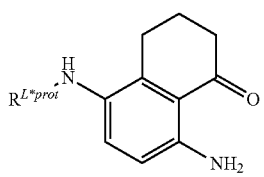

with the compound A3 using the Friedlander reaction.

Compounds of Formula 5 may be synthesised from compounds of Formula 6:

Formula 6

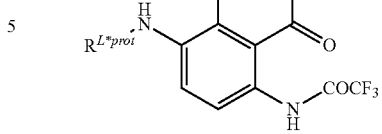

by removal of the trifluoroacetamide protecting group.

Compounds of Formula 6 may be synthesised by coupling: $R^{L*prot}$—OH to the compound 17.

Compounds of formula I where $R^L$ is of formula Ia or Ib may be synthesised from the compound I11 by coupling of the compound $R^L$—OH, or an activated form thereof.

Amine Protecting Groups

Amine protecting groups are well-known to those skilled in the art. Particular reference is made to the disclosure of suitable protecting groups in Greene's Protecting Groups in Organic Synthesis, Fourth Edition, John Wiley & Sons, 2007 (ISBN 978-0-471-69754-1), pages 696-871.

Further Preferences

The following preferences may apply to all aspects of the invention as described above, or may relate to a single aspect. The preferences may be combined together in any combination.

$Q^X$

In one embodiment, Q is an amino acid residue. The amino acid may be a natural amino acid or a non-natural amino acid.

In one embodiment, Q is selected from: Phe, Lys, Val, Ala, Cit, Leu, Ile, Arg, and Trp, where Cit is citrulline.

In one embodiment, Q comprises a dipeptide residue. The amino acids in the dipeptide may be any combination of natural amino acids and non-natural amino acids. In some embodiments, the dipeptide comprises natural amino acids. Where the linker is a cathepsin labile linker, the dipeptide is the site of action for cathepsin-mediated cleavage. The dipeptide then is a recognition site for cathepsin.

In one embodiment, Q is selected from:
$^{NH}$-Phe-Lys-$^{C=O}$,
$^{NH}$-Val-Ala-$^{C=O}$
$^{NH}$-Val-Lys-$^{C=O}$
$^{NH}$-Ala-Lys-$^{C=O}$
$^{NH}$-Val-Cit-$^{C=O}$
$^{NH}$-Phe-Cit-$^{C=O}$
$^{NH}$-Leu-Cit-$^{C=O}$
$^{NH}$-Ile-Cit-$^{C=O}$
$^{NH}$-Phe-Arg-$^{C=O}$
$^{NH}$-Trp-Cit-$^{C=O}$, and
$^{NH}$-Gly-Val-$^{C=O}$;
where Cit is citrulline.

Preferably, Q is selected from:
$^{NH}$-Phe-Lys-$^{C=O}$
$^{NH}$-Val-Ala-$^{C=O}$
$^{NH}$-Val-Lys-$^{C=O}$
$^{NH}$-Ala-Lys-$^{C=O}$, and
$^{NH}$-Val-Cit-$^{C=O}$ Most preferably, Q is selected from $^{NH}$-Phe-Lys-$^{C=O}$, $^{NH}$-Val-Cit-$^{C=O}$ or $^{NH}$-Val-Ala-$^{C=O}$. Other dipeptide combinations of interest include:
$^{NH}$-Gly-Gly-$^{C=O}$
$^{NH}$-Gly-Val-$^{C=O}$
$^{NH}$-Pro-Pro-$^{C=O}$, and
$^{NH}$-Val-Glu-$^{C=O}$.

Other dipeptide combinations may be used, including those described by Dubowchik et al., *Bioconjugate Chemistry*, 2002, 13, 855-869, which is incorporated herein by reference.

In some embodiments, Q is a tripeptide residue. The amino acids in the tripeptide may be any combination of natural amino acids and non-natural amino acids. In some embodiments, the tripeptide comprises natural amino acids. Where the linker is a cathepsin labile linker, the tripeptide is the site of action for cathepsin-mediated cleavage. The tripeptide then is a recognition site for cathepsin. Tripeptide linkers of particular interest are:

$^{NH}$-Glu-Val-Ala-$^{C=O}$
$^{NH}$-Glu-Val-Cit-$^{C=O}$
$^{NH}$-αGlu-Val-Ala-$^{C=O}$
$^{NH}$-αGlu-Val-Cit-$^{C=O}$

In some embodiments, Q is a tetrapeptide residue. The amino acids in the tetrapeptide may be any combination of natural amino acids and non-natural amino acids. In some embodiments, the tetrapeptide comprises natural amino acids. Where the linker is a cathepsin labile linker, the tetrapeptide is the site of action for cathepsin-mediated cleavage. The tetrapeptide then is a recognition site for cathepsin. Tetrapeptide linkers of particular interest are:

$^{NH}$-Gly-Gly-Phe-Gly$^{C=O}$; and $^{NH}$-Gly-Phe-Gly-Gly$^{C=O}$.

In some embodiments, the tetrapeptide is:

$^{NH}$-Gly-Gly-Phe-Gly$^{C=O}$.

In the above representations of peptide residues, $^{NH}$- represents the N-terminus, and -$^{C=O}$ represents the C-terminus of the residue. The C-terminus binds to the NH of A*.

Glu represents the residue of glutamic acid, i.e.:

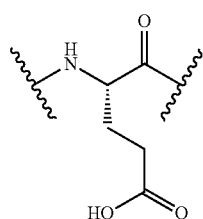 [SMILES: *N[C@@H](CCC(=O)O)C(*)=O]

αGlu represents the residue of glutamic acid when bound via the α-chain, i.e.:

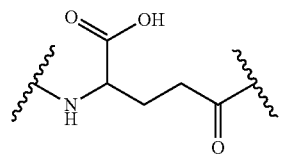 [SMILES: *NC(CCC(*)=O)C(=O)O]

In one embodiment, the amino acid side chain is chemically protected, where appropriate. The side chain protecting group may be a group as discussed above. Protected amino acid sequences are cleavable by enzymes. For example, a dipeptide sequence comprising a Boc side chain-protected Lys residue is cleavable by cathepsin.

Protecting groups for the side chains of amino acids are well known in the art and are described in the Novabiochem Catalog, and as described above.

$G^L$ $G^L$ may be selected from

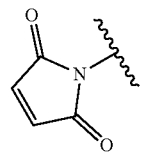 (G$^{L1-1}$)

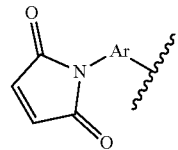 (G$^{L1-2}$)

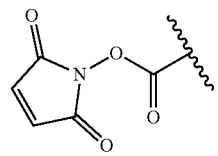 (G$^{L2}$)

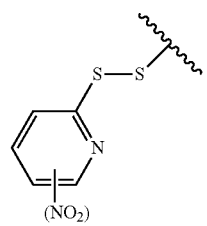 (G$^{L3-1}$)

(NO$_2$)

where the NO$_2$ group is optional

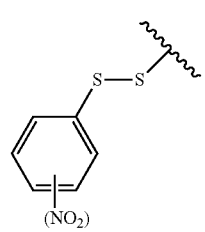 (G$^{L3-2}$)

(NO$_2$)

where the NO$_2$ group is optional

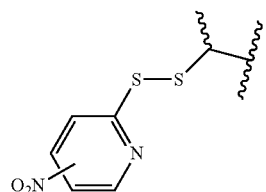 (G$^{L3-3}$)

where the NO$_2$ group is optional

-continued (G$^{L3-4}$)

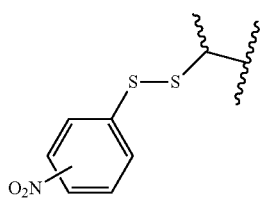

where the NO$_2$ group is optional (G$^{L4}$)

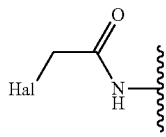

Where Hal = I, Br, Cl (G$^{L5}$)

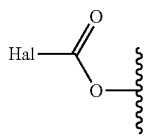

(G$^{L6}$)

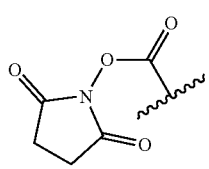

(G$^{L7}$)

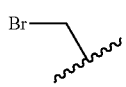

(G$^{L8}$)

(G$^{L9}$)

(G$^{L10}$)

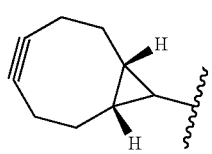

(G$^{L11}$)

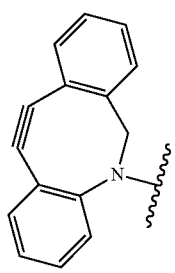

-continued (G$^{L12}$)

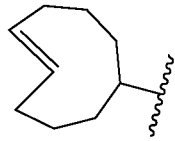

(G$^{L13}$)

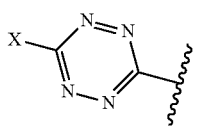

(G$^{L14}$)

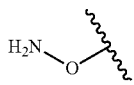

where Ar represents a C$_{5-6}$ arylene group, e.g. phenylene, and X represents C$_{1-4}$ alkyl.

In some embodiments, G$^L$ is selected from G$^{L1-1}$ and G$^{L1-2}$. In some of these embodiments, G$^L$ is G$^{L1-1}$.

G$^{LL}$

G$^{LL}$ may be selected from:

(G$^{LL1-1}$)

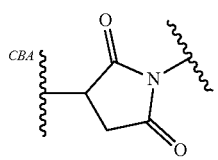

(G$^{LL1-2}$)

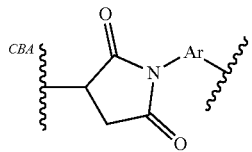

(G$^{LL2}$)

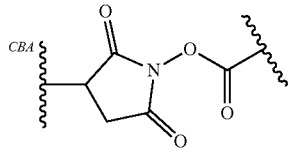

(G$^{LL3-1}$)

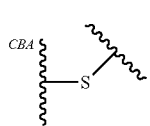

(G$^{LL3-2}$)

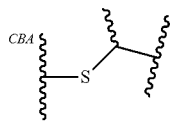

(G$^{LL4}$)

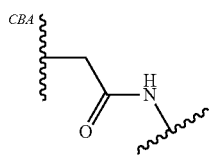

(G^{LL5}) 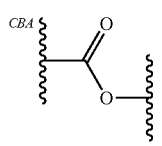
(G^{LL6}) 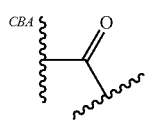
(G^{LL7}) 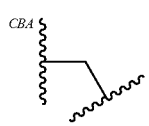
(G^{LL8-1}) 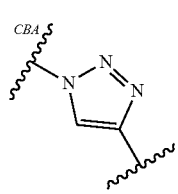
(G^{LL8-2}) 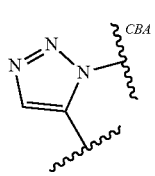
(G^{LL9-1}) 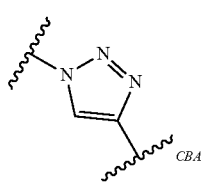
(G^{LL9-2}) 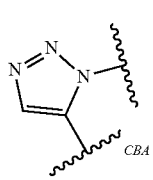
(G^{LL10}) 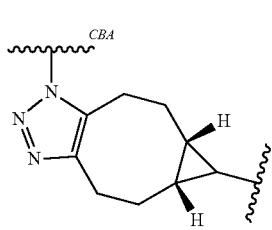
(G^{LL11}) 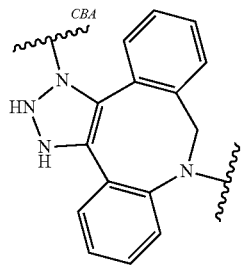
(G^{LL12}) 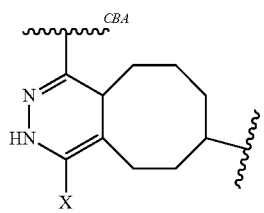
(G^{LL13}) 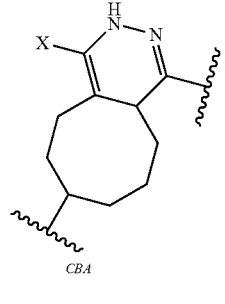
(G^{LL14}) 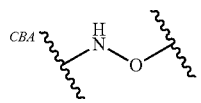
where r represents a $C_{5-6}$ arylene group, e.g. phenylene and X represent $C_{1-4}$ alkyl.
In some embodiments, $G^{LL}$ is selected from $G^{LL1-1}$ and $G^{LL1-2}$. In some of these embodiments, $G^{LL}$ is $G^{LL1-1}$.
X
X is:
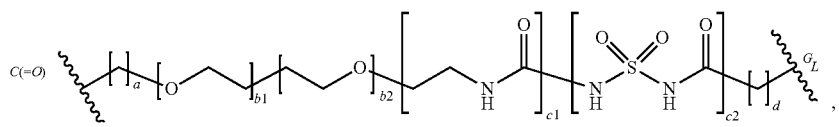

where a=0 to 5, b1=0 to 16, b2=0 to 16, c=0 or 1, d=0 to 5, wherein atleast b1 orb2=0 and at least c1 or c2=0.

a may be 0, 1, 2, 3, 4 or 5. In some embodiments, a is 0 to 3. In some of these embodiments, a is 0 or 1. In further embodiments, a is 0.

b1 may be 0, 1, 2, 3, 4, 5, 6, 7, 8, 9, 10, 11, 12, 13, 14, 15 or 16. In some embodiments, b1 is 0 to 12. In some of these embodiments, b1 is 0 to 8, and may be 0, 2, 3, 4, 5 or 8.

b2 may be 0, 1, 2, 3, 4, 5, 6, 7, 8, 9, 10, 11, 12, 13, 14, 15 or 16. In some embodiments, b2 is 0 to 12. In some of these embodiments, b2 is 0 to 8, and may be 0, 2, 3, 4, 5 or 8.

Only one of b1 and b2 may not be 0.

c1 may be 0 or 1.

c2 may be 0 or 1.

Only one of c1 and c2 may not be 0.

d may be 0, 1, 2, 3, 4 or 5. In some embodiments, d is 0 to 3. In some of these embodiments, d is 1 or 2. In further embodiments, d is 2. In further embodiments, d is 5.

In some embodiments of X, a is 0, b1 is 0, c1 is 1, c2 is 0 and d is 2, and b2 may be from 0 to 8. In some of these embodiments, b2 is 0, 2, 3, 4, 5 or 8.

In some embodiments of X, a is 1, b2 is 0, c1 is 0, c2 is 0 and d is 0, and b1 may be from 0 to 8. In some of these embodiments, b1 is 0, 2, 3, 4, 5 or 8.

In some embodiments of X, a is 0, b1 is 0, c1 is 0, c2 is 0 and d is 1, and b2 may be from 0 to 8. In some of these embodiments, b2 is 0, 2, 3, 4, 5 or 8.

In some embodiments of X, b1 is 0, b2 is 0, c1 is 0, c2 is 0 and one of a and d is 0. The other of a and d is from 1 to 5. In some of these embodiments, the other of a and d is 1. In other of these embodiments, the other of a and d is 5.

In some embodiments of X, a is 1, b2 is 0, c1 is 0, c2 is 1, d is 2, and b1 may be from 0 to 8. In some of these embodiments, b2 is 0, 2, 3, 4, 5 or 8.

In some embodiments, $R^L$ is of formula Ib.

In some embodiments, $R^{LL}$ is is formula Ib'.

$R^{L1}$ and $R^{L2}$ are independently selected from H and methyl, or together with the carbon atom to which they are bound form a cyclopropylene or cyclobutylene group.

In some embodiments, both $R^{L1}$ and $R^{L2}$ are H.

In some embodiments, $R^{L1}$ is H and $R^{L2}$ is methyl.

In some embodiments, both $R^{L1}$ and $R^{L2}$ are methyl.

In some embodiments, $R^{L1}$ and $R^{L2}$ together with the carbon atom to which they are bound form a cyclopropylene group.

In some embodiments, $R^{L1}$ and $R^{L2}$ together with the carbon atom to which they are bound form a cyclobutylene group.

In the group Ib, in some embodiments, e is 0. In other embodiments, e is 1 and the nitro group may be in any available position of the ring. In some of these embodiments, it is in the ortho position. In others of these embodiments, it is in the para position.

In some embodiments of the fifth aspect of the invention, the enantiomerically enriched form has an enantiomeric ratio greater than 60:40, 70:30; 80:20 or 90:10. In further embodiments, the enantiomeric ratio is greater than 95:5, 97:3 or 99:1.

In some embodiments, $R^L$ is selected from:

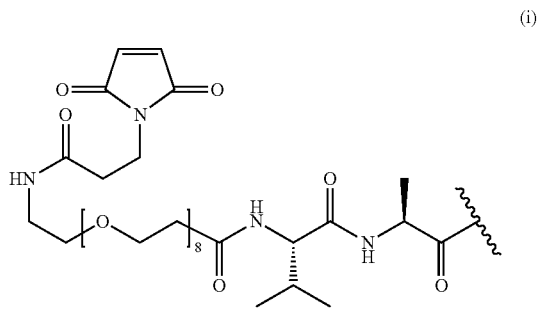

(i)

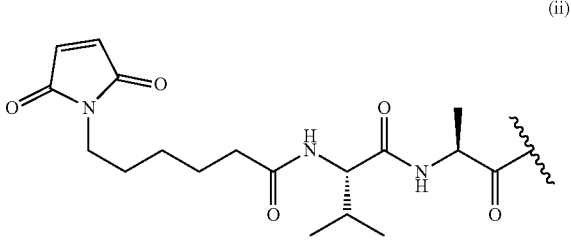

(ii)

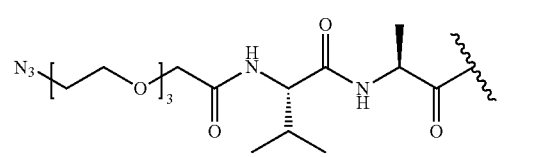

(iii)

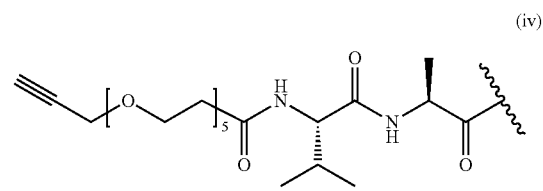

(iv)

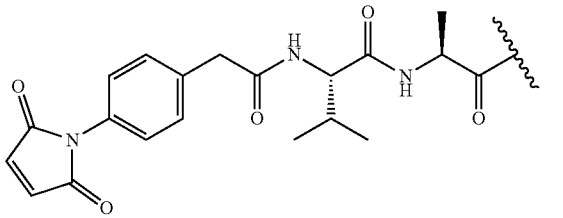

(v)

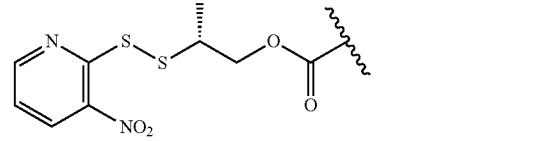

(vi)

-continued (vii)

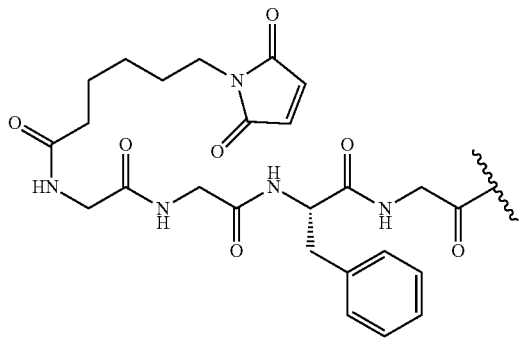

(viii)

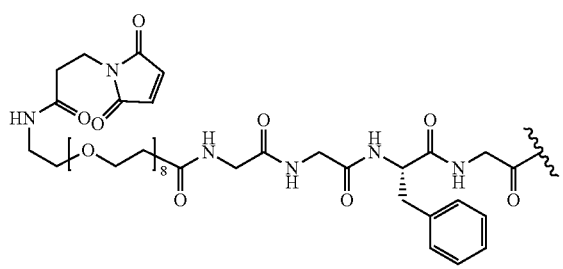

(ix)

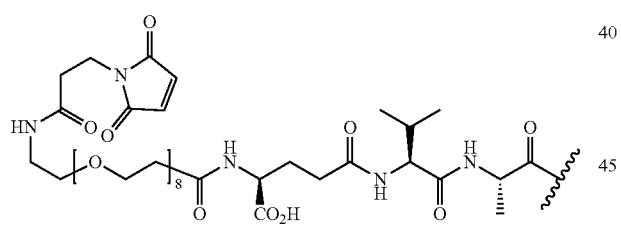

In some embodiments, $R^{LL}$ is a group derived from the $R^L$ groups above.

In one embodiment of the first aspect of the invention, the compound of formula I is:

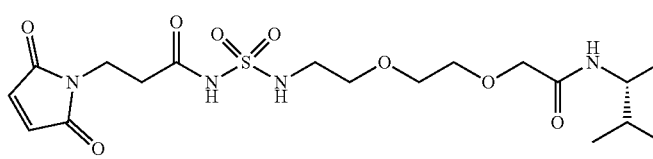

Further Preferences

In some embodiments, the compound of formula I is of the formula $I^P$:

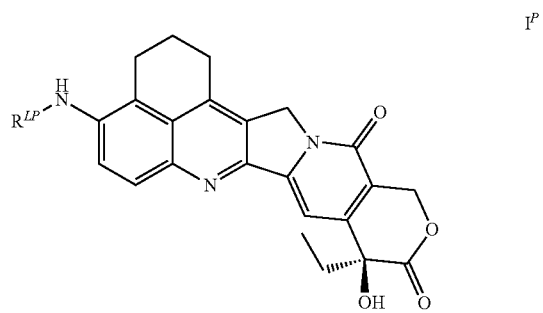

and salts and solvates thereof, wherein $R^{LP}$ is a linker for connection to a cell binding agent, which is selected from:

(ia):

wherein
$Q^P$ is:

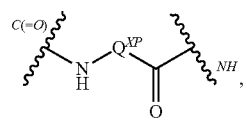

where $Q^{XP}$ is such that $Q^P$ is an amino-acid residue, a dipeptide residue or a tripeptide residue;

$X^P$ is:

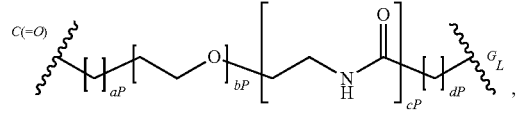

where aP=0 to 5, bP=0 to 16, cP=0 or 1, dP=0 to 5;
$G^L$ is a linker for connecting to a Ligand Unit;

(ib):

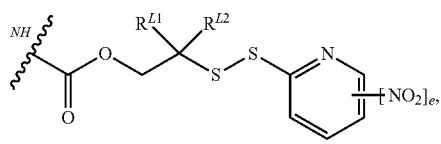

where $R^{L1}$ and $R^{L2}$ are independently selected from H and methyl, or together with the carbon atom to which they are bound form a cyclopropylene or cyclobutylene group; and e is 0 or 1.

aP may be 0, 1, 2, 3, 4 or 5. In some embodiments, aP is 0 to 3. In some of these embodiments, aP is 0 or 1. In further embodiments, aP is 0.

bP may be 0, 1, 2, 3, 4, 5, 6, 7, 8, 9, 10, 11, 12, 13, 14, 15 or 16. In some embodiments, b is 0 to 12. In some of these embodiments, bP is 0 to 8, and may be 0, 2, 4 or 8.

cP may be 0 or 1.

dP may be 0, 1, 2, 3, 4 or 5. In some embodiments, dP is 0 to 3. In some of these embodiments, dP is 1 or 2. In further embodiments, dP is 2.

In some embodiments of $X^P$, aP is 0, cP is 1 and dP is 2, and bP may be from 0 to 8. In some of these embodiments, bP is 0, 4 or 8.

The preferences for $Q^X$ above for compounds of Formula I may apply to $Q^{XP}$, where appropriate.

The preferences for $G^L$, $R^{L1}$, $R^{L2}$ and e above for compounds of Formula I may apply to compounds of Formula IP.

In some embodiments, the conjugate of formula IV is of the formula $IV^P$:

$$L-(D^{LP})_p \qquad (IV^P)$$

or a pharmaceutically acceptable salt or solvate thereof, wherein L is a Ligand unit (i.e., a targeting agent), $D^{LP}$ is a Drug Linker unit that is of formula $III^P$:

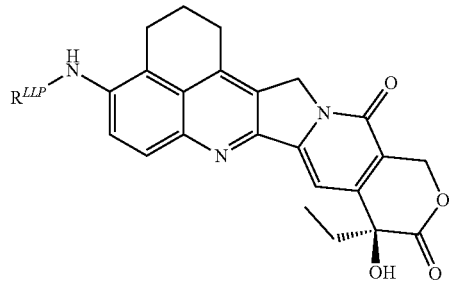

$R^{LLP}$ is a linker connected to the Ligand unit selected from
(ia'):

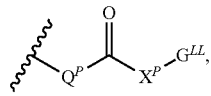

where $Q^P$ and $X^P$ are as defined above and $G^{LL}$ is a linker connected to a Ligand Unit; and (ib'):

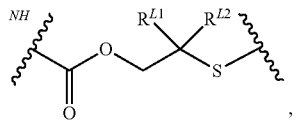

where $R^{L1}$ and $R^{L2}$ are as defined above; and p is an integer of from 1 to 20.

In some embodiments, the compound of formula I is of the formula $I^{P2}$:

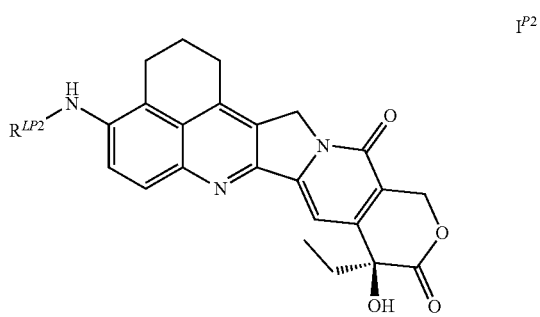

and salts and solvates thereof, wherein $R^{LP2}$ is a linker for connection to a cell binding agent, which is selected from:
(ia):

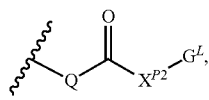

wherein
Q is:

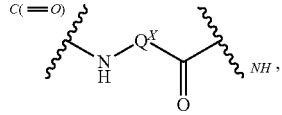

where $Q^X$ is such that Q is an amino-acid residue, a dipeptide residue, a tripeptide residue or a tetrapeptide residue;

$X^{P2}$ is:

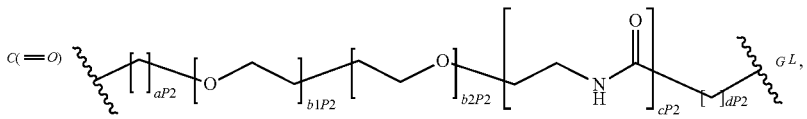

where aP2=0 to 5, b1P2=0 to 16, b2P2=0 to 16, cP2=0 or 1, dP2=0 to 5, wherein at least b1P2 or b2P2=0 (i.e. only one of b1 and b2 may not be 0);
$G^L$ is a linker for connecting to a Ligand Unit;
(ib):

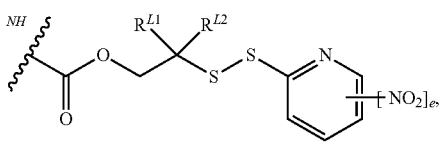

where $R^{L1}$ and $R^{L2}$ are independently selected from H and methyl, or together with the carbon atom to which they are bound form a cyclopropylene or cyclobutylene group; and
e is 0 or 1.

aP2 may be 0, 1, 2, 3, 4 or 5. In some embodiments, aP2 is 0 to 3. In some of these embodiments, aP2 is 0 or 1. In further embodiments, aP2 is 0.

b1P2 may be 0, 1, 2, 3, 4, 5, 6, 7, 8, 9, 10, 11, 12, 13, 14, 15 or 16. In some embodiments, b1P2 is 0 to 12. In some of these embodiments, b1P2 is 0 to 8, and may be 0, 2, 3, 4, 5 or 8.

b2P2 may be 0, 1, 2, 3, 4, 5, 6, 7, 8, 9, 10, 11, 12, 13, 14, 15 or 16. In some embodiments, b2P2 is 0 to 12. In some of these embodiments, b2P2 is 0 to 8, and may be 0, 2, 3, 4, 5 or 8.

Only one of b1P2 and b2P2 may not be 0.

cP2 may be 0 or 1.

dP2 may be 0, 1, 2, 3, 4 or 5. In some embodiments, dP2 is 0 to 3. In some of these embodiments, dP2 is 1 or 2. In further embodiments, dP2 is 2. In further embodiments, dP2 is 5.

In some embodiments of $X^{P2}$, aP2 is 0, b1P2 is 0, cP2 is 1 and dP2 is 2, and b2P2 may be from 0 to 8. In some of these embodiments, b2P2 is 0, 2, 3, 4, 5 or 8.

In some embodiments of $X^{P2}$, aP2 is 1, b2P2 is 0, cP2 is 0 and dP2 is 0, and b1P2 may be from 0 to 8. In some of these embodiments, b1P2 is 0, 2, 3, 4, 5 or 8.

In some embodiments of $X^{P2}$, aP2 is 0, b1P2 is 0, cP2 is 0 and dP2 is 1, and b2P2 may be from 0 to 8. In some of these embodiments, b2P2 is 0, 2, 3, 4, 5 or 8.

In some embodiments of $X^{P2}$, b1P2 is 0, b2P2 is 0, cP2 is 0 and one of aP2 and dP2 is 0.

The other of aP2 and d is from 1 to 5. In some of these embodiments, the other of aP2 and d is 1. In other of these embodiments, the other of aP2 and dP2 is 5.

The preferences for $Q^X$ above for compounds of Formula I may apply to $Q^X$ in Formula $Ia^{P2}$, where appropriate.

The preferences for $G^L$, $R^{L1}$, $R^{L2}$ and e above for compounds of Formula I may apply to compounds of Formula $I^{P2}$.

In some embodiments, the conjugate of formula IV is of the formula $IV^{P2}$:

$$L-(D^{LP2})_p \qquad (IV^{P2})$$

or a pharmaceutically acceptable salt or solvate thereof, wherein L is a Ligand unit (i.e., a targeting agent), $D^{LP2}$ is a Drug Linker unit that is of formula $III^{P2}$:

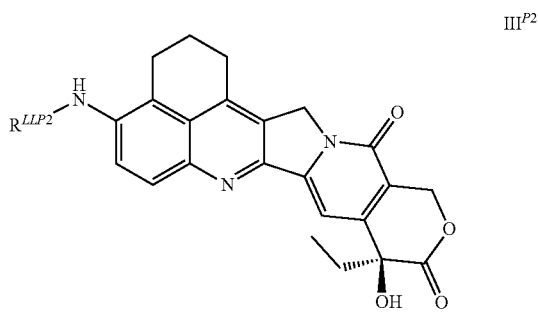

$R^{LLP2}$ is a linker connected to the Ligand unit selected from
(ia'):

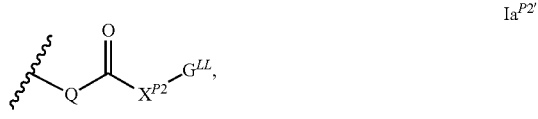

where Q and $X^{P2}$ are as defined above and $G^{LL}$ is a linker connected to a Ligand Unit; and
(ib'):

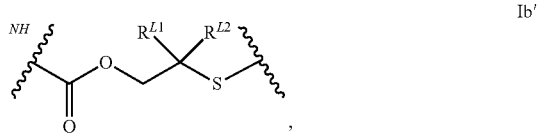

where $R^{L1}$ and $R^{L2}$ are as defined above; and
p is an integer of from 1 to 20.

EXAMPLES

General Information

Flash chromatography was performed using a Biotage@ Isolera™ and fractions checked for purity using thin-layer chromatography (TLC). TLC was performed using Merck Kieselgel 60 F254 silica gel, with fluorescent indicator on aluminium plates. Visualisation of TLC was achieved with UV light.

Extraction and chromatography solvents were bought and used without further purification from VWR U.K.

All fine chemicals were purchased from Sigma-Aldrich unless otherwise stated.

Pegylated reagents were obtained from Quanta biodesign US via Stratech UK.

LC/MS Conditions

Method A

Positive mode electrospray mass spectrometry was performed using a Waters Aquity H-class SQD2.

Mobile phases used were solvent A (water with 0.1% formic acid) and solvent B (acetonitrile with 0.1% formic acid). Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Detection was at 254 nm. Columns: Waters Acquity UPLCO BEH Shield RP18 1.7 µm 2.1×50 mm at 50° C. fitted with Waters Acquity UPLC® BEH Shield RP18 VanGuard Pre-column, 130A, 1.7 µm, 2.1 mm×5 mm.

Method B

The HPLC (Waters Alliance 2695) was run using a mobile phase of water (A) (formic acid 0.1%) and acetonitrile (B) (formic acid 0.1%).

Initial composition 5% B held over 25 seconds, then increased from 5% B to 100% B over a 1 minute 35 seconds' period. The composition was held for 50 seconds at 100% B, then returned to 5% B in 5 seconds and held there for 5 seconds. The total duration of the gradient run was 3.0 minutes. Flow rate was 0.8 mL/minute. Wavelength detection range: 190 to 800 nm. Columns: Waters Acquity UPLC® BEH Shield RP18 1.7 µm 2.1×50 mm at 50° C. fitted with Waters Acquity UPLC@ BEH Shield RP18 VanGuard Pre-column, 130A, 1.7 µm, 2.1 mm×5 mm.

Method C

The HPLC (Waters Alliance 2695) was run using a mobile phase of water (A) (formic acid 0.1%) and acetonitrile (B) (formic acid 0.1%).

Initial composition 5% B held over 1 min, then increase from 5% B to 100% B over a 9 min period. The composition was held for 2 min at 100% B, then returned to 5% B in 0.10 minutes and hold there for 3 min. Total gradient run time equals 15 min. Flow rate 0.6 mL/min. Wavelength detection range: 190 to 800 nm. Oven temperature: 50° C. Column: ACE Excel 2 C18-AR, 2µ, 3.0×100 mm.

HPLC Conditions

Reverse-phase ultra-fast high-performance liquid chromatography (UFLC) was carried out on a Shimadzu Prominence™ machine using a Phenomenex™ Gemini NX 5p C18 column (at 50° C.) dimensions: 150×21.2 mm. Eluents used were solvent A (H$_2$O with 0.1% formic acid) and solvent B (CH$_3$CN with 0.1% formic acid). All UFLC experiments were performed with gradient conditions: Initial composition 13% B increased to 30% B over a 3 minutes period, then increased to 45% B over 8 minutes and again to 100% over 6 minutes before returning to 13% over 2 min and hold for 1 min. The total duration of the gradient run was 20.0 minutes. Flow rate was 20.0 mL/minute and detection was at 254 and 223 nm.

NMR Method

Proton NMR chemical shift values were measured on the delta scale at 400 MHz using a Bruker AV400. The following abbreviations have been used: s, singlet; d, doublet; t, triplet; q, quartet; quin, quintet; m, multiplet; br, broad. Coupling constants are reported in Hz.

Synthesis of Key Intermediates

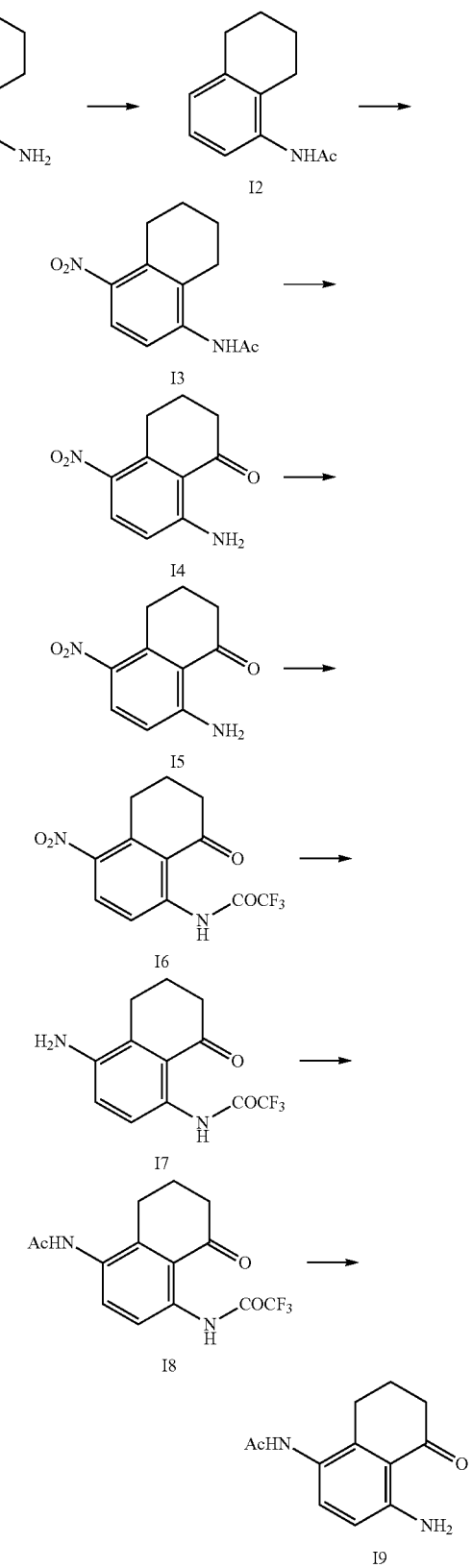

a) N-(5,6,7,8-tetrahydronaphthalen-1-yl)acetamide (I2)

5,6,7,8-tetrahydronaphthalen-1-amine I1 (8.54 g, 58.0 mmol) was dissolved in dichloromethane (80 mL). Triethylamine (18 mL, 129 mmol) was added and the mixture cooled to 0° C. Dropwise, acetic anhydride (11.5 mL, 122 mmol) was added, upon completion of the addition, the reaction mixture was warmed to rt and stirred for 45 min, whereupon LCMS indicated the reaction was complete. The mixture was diluted with $CH_2Cl_2$, washed with $H_2O$, sat. $NaHCO_3$, 10% citric acid, the organic phase dried over $MgSO_4$ and concentrated in vacuo. The off-white solid was triturated with 1:3 $Et_2O$/isohexane to afford 12 (10.8 g, 57.1 mmol, 98% Yield) as a white solid which was used without further purification. LC/MS (method A): retention time 1.44 mins (ES+) m/z 190 $[M+H]^+$ b) N-(4-nitro-5,6,7,8-tetrahydronaphthalen-1-yl)acetamide (I3)

N-(5,6,7,8-tetrahydronaphthalen-1-yl)acetamide 12 (1.00 g, 5.2840 mmol) was added portion-wise to sulfuric acid (15 mL, 281 mmol) at −5° C. Sodium nitrate (450 mg, 5.2945 mmol) was added portion-wise to the reaction mixture and stirred for 30 min at −5° C. whereupon LCMS indicated no further reaction progress. The reaction mixture was poured onto ice with external cooling, the aqueous mixture extracted with $CH_2Cl_2$, the organic phase dried over $MgSO_4$ and purified by Isolera (10-80% EtOAc in isohexane) to afford a mixture of N-(4-nitro-5,6,7,8-tetrahydronaphthalen-1-yl)acetamide 13 and N-(2-nitro-5,6,7,8-tetrahydronaphthalen-1-yl)acetamide (956 mg, 4.0811 mmol, 77% Yield) as a white/yellow solid. LC/MS (method A): retention time 1.53 mins (ES+) m/z 235 $[M+H]^+$.

c) N-(4-nitro-8-oxo-5,6,7,8-tetrahydronaphthalen-1-yl)acetamide (I4)

N-(4-nitro-5,6,7,8-tetrahydronaphthalen-1-yl)acetamide 13 (1.01 g, 4.31 mmol) was dissolved in acetone (30 mL). Magnesium sulfate in water (3.9 mL, 5.9 mmol, 1.5 mol/L) was added and the mixture was cooled to 0° C. Potassium permanganate (2.07 g, 13.0 mmol) was added portionwise to the reaction mixture and the mixture warmed to rt and stirred for 50 min, whereupon TLC indicated the reaction was complete. The reaction mixture was filtered through Celite, the solids washed with $CHCl_3$ and the resulting organic mixture washed with $H_2O$, brine, dried over $MgSO_4$ and purified by isolera (20-50% EtOAc in isohexane) to afford a mixture of N-(4-nitro-8-oxo-5,6,7,8-tetrahydronaphthalen-1-yl)acetamide 14 and N-(2-nitro-8-oxo-5,6,7,8-tetrahydronaphthalen-1-yl)acetamide (709 mg, 2.86 mmol, 66%) as a white/yellow solid. LC/MS (method A): retention time 1.44 mins (ES+) m/z 190 $[M+H]^+$ d) 8-amino-5-nitro-3,4-dihydronaphthalen-1(2H)-one (I5)

A mixture of N-(4-nitro-8-oxo-5,6,7,8-tetrahydronaphthalen-1-yl)acetamide 14 and N-(2-nitro-8-oxo-5,6,7,8-tetrahydronaphthalen-1-yl)acetamide (709 mg, 2.8561 mmol) and 6N hydrochloric acid (7 mL) were stirred at 80° C. for 2.5 h, whereupon LCMS indicated the reaction was complete. The reaction mixture was cooled in an ice bath and 6N NaOH solution was added until the pH was basic. The aqueous mixture was extracted with $CH_2Cl_2$, the organic phase dried over $MgSO_4$ and concentrated in vacuo. Isolera (0-50% EtOAc in isohexane) afforded 8-amino-5-nitro-3,4-dihydronaphthalen-1(2H)-one 15 (320 mg, 1.552 mmol, 54% Yield) as a yellow/orange solid. LC/MS (method A): retention time 1.54 mins (ES+) m/z 207 $[M+H]^+$ e) 2,2,2-trifluoro-N-(4-nitro-8-oxo-5,6,7,8-tetrahydronaphthalen-1-yl)acetamide (I6)

8-amino-5-nitro-3,4-dihydronaphthalen-1(2H)-one I5 (430 mg, 2.0854 mmol) was dissolved in dichloromethane (20 mL). Pyridine (340 μL, 4.20 mmol) was added and the mixture cooled to 0° C. Trifluoroacetic anhydride (590 μL, 4.197 mmol) was added and stirred for 30 min, whereupon LCMS indicated the reaction was complete. The mixture was diluted with $CH_2Cl_2$, washed with $H_2O$, the organic phase dried over $MgSO_4$ and concentrated in vacuo to afford 2,2,2-trifluoro-N-(4-nitro-8-oxo-5,6,7,8-tetrahydronaphthalen-1-yl)acetamide 16 (630 mg, 2.0846 mmol, >99% Yield) as a yellow solid, which was used without further purification. LC/MS (method A): retention time 1.86 min (ES+) m/z 301X $[M-H]^-$ f) N-(4-amino-8-oxo-5,6,7,8-tetrahydronaphthalen-1-yl)-2,2,2-trifluoroacetamide (I7)

Zinc (2.73 g, 41.7 mmol) was suspended in methanol (80 mL), formic acid (4 mL) and water (4 mL) and the mixture cooled to 0° C. 2,2,2-trifluoro-N-(4-nitro-8-oxo-5,6,7,8-tetrahydronaphthalen-1-yl)acetamide I6 (568 mg, 2.0865 mmol) was added portion-wise and the mixture stirred at 0° C. for 30 min, whereupon LCMS indicated the reaction was complete. The reaction mixture was filtered, the filtrate diluted with EtOAc and washed with sat $NaHCO_3$. The organic phase was dried over $MgSO_4$ and concentrated in vacuo to afford N-(4-amino-8-oxo-5,6,7,8-tetrahydronaphthalen-1-yl)-2,2,2-trifluoroacetamide I7 (568 mg, 2.0865 mmol, >99% Yield) as a yellow solid, which was used without further purification. LC/MS (method A): retention time 1.65 min (ES+) m/z 273 $[M+H]^+$ g) N-(4-acetamido-8-oxo-5,6,7,8-tetrahydronaphthalen-1-yl)-2,2,2-trifluoroacetamide (I8)

N-(8-amino-4-oxo-tetralin-5-yl)-2,2,2-trifluoro-acetamide I7 (568 mg, 2.0865 mmol) was dissolved in dichloromethane (20 mL). Triethylamine (580 μL, 4.16 mmol) then acetyl chloride (297 μL, 4.173 mmol) were added and the mixture stirred for 30 min, whereupon LCMS indicated the reaction was complete. The reaction mixture was diluted with $CH_2Cl_2$, washed with $H_2O$, the organic phase dried over $MgSO_4$ and concentrated in vacuo to afford N-(8-acetamido-4-oxo-tetralin-5-yl)-2,2,2-trifluoro-acetamide 18 (655 mg, 2.084 mmol, >99% yield) as a yellow solid, which was used without further purification. LC/MS (method A): retention time 1.55 min (ES+) m/z 315 $[M+H]^+$ h) N-(4-amino-5-oxo-5,6,7,8-tetrahydronaphthalen-1-yl)acetamide (I9)

N-(8-acetamido-4-oxo-tetralin-5-yl)-2,2,2-trifluoro-acetamide I8 (2.77 g, 8.81 mmol) was dissolved in methanol (240 mL) and water (17 mL). Potassium carbonate (4.88 g, 35.3 mmol) was added and the mixture stirred for 1.5 h at 50° C., whereupon LCMS indicated the reaction was complete. The reaction mixture was cooled, concentrated in vacuo, dissolved in 10% MeOH in $CH_2Cl_2$ and washed with H₂O. The organic phase was dried over MgSO₄ and purified by isolera chromatography (2-15% MeOH in CH₂Cl₂) to afford N-(8-amino-1-oxo-tetralin-5-yl)acetamide 19 (1.20 g, 5.50 mmol, 62.3% Yield) as a yellow solid. LC/MS (method A): retention time 0.98 min (ES+) m/z 219 [M+H]⁺

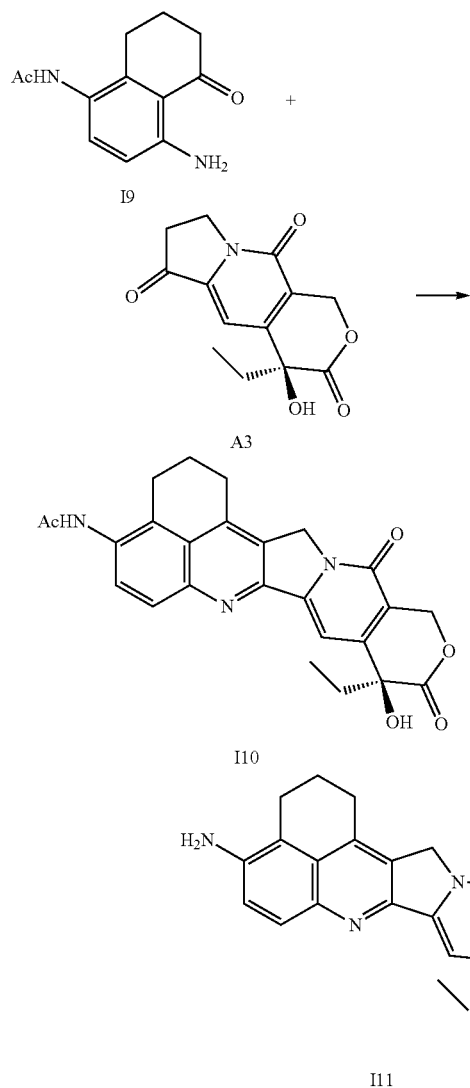

i) (S)—N-(9-ethyl-9-hydroxy-10,13-dioxo-2,3,9,10, 13,15-hexahydro-1H,12H-benzo[de]pyrano[3',4':6,7] indolizino[1,2-b]quinolin-4-yl)acetamide (I10)

N-(8-amino-1-oxo-tetralin-5-yl)acetamide 19 (641 mg, 2.94 mmol, 1.0 eq.), (S)-4-ethyl-4-hydroxy-7,8-dihydro-1H-pyrano[3,4-f]indolizine-3,6,10(4H)-trione A3 (840 mg, 3.19 mmol, 1.1 eq.) and PPTS (740 mg, 2.95 mmol, 1.0 eq.) were dissolved in toluene (60 mL) and stirred at reflux for 3 h, whereupon LCMS indicated 19 had been consumed. The reaction mixture was cooled and concentrated in vacuo. The resulting solids were triturated with acetonitrile, then acetone to afford I10 as a brown solid with minor TsOH contamination (1.26 g, 96%). LC/MS (method A): retention time 1.32 mins (ES+) m/z 447 [M+H]⁺ j) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11)

(S)—N-(9-ethyl-9-hydroxy-10,13-dioxo-2,3,9,10,13,15-hexahydro-1H,12H-benzo[de]pyrano[3',4':6,7]indolizino[1, 2-b]quinolin-4-yl)acetamide (I10) (1.26 g, 2.83 mmol, 1.0 eq.) was dissolved in hydrochloric acid (6 mol/L) in H₂O (12 mL) and the mixture stirred for 5 h at 80° C., whereupon LCMS indicated I10 had been consumed. The reaction mixture was diluted with H₂O and concentrated in vacuo to afford (S)-4-amino-9-ethyl-9-hydroxy-1,2,3,9,12,15-hexahydro-10H,13H-benzo[de]pyrano[3',4':6,7]indolizino[1,2-b]quinoline-10,13-dione I11 (1.51 g, 2.85 mmol, 90 mass %, 101% Yield) as a red crystaline solid. LC/MS (method A): retention time 1.36 mins (ES+) m/z 405 [M+H]⁺.

Alternate Synthesis of I11

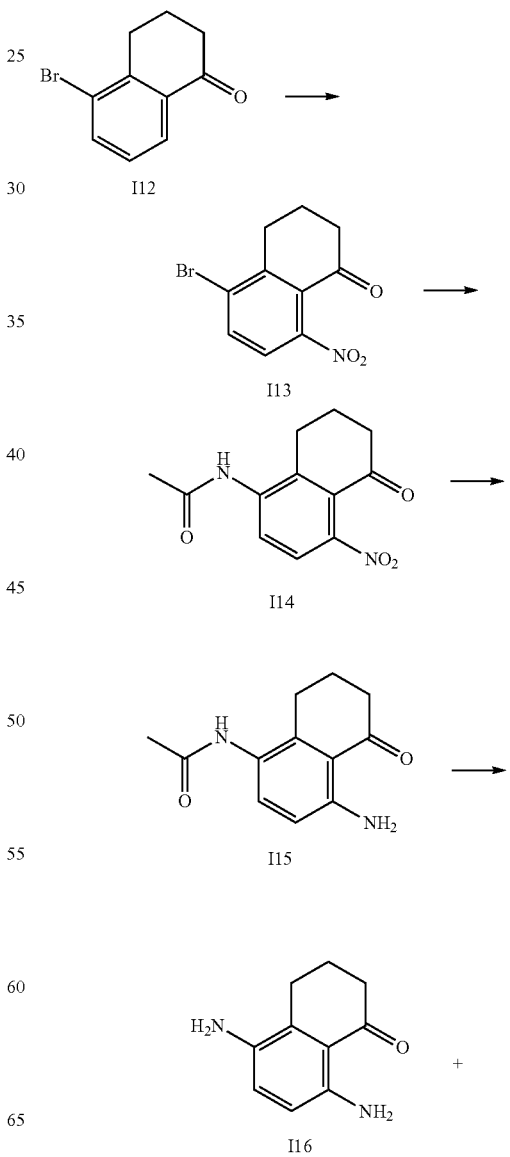

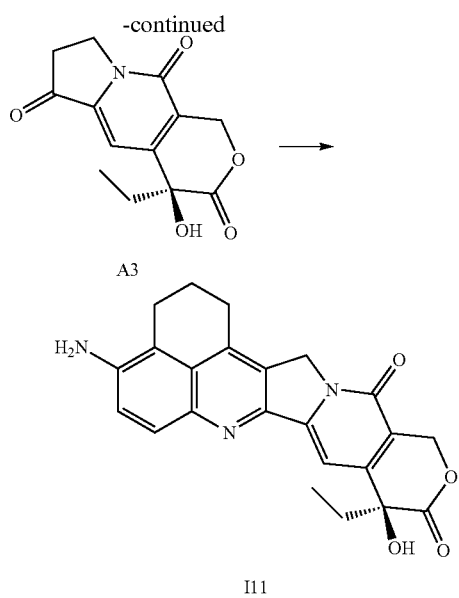

IPC, Purity and Assay Method for this Synthesis

| Instrument | Thermo U-3000 |
|---|---|
| Column | ACE Excel 3 C18-PFP (3.0 mm × 150 mm) |
| Oven | 40° C. |
| Mobile phase | A: 10 mM Ammomium Formate in water pH = 3.5 |
| | B: CAN |

| Gradient program | Time (min) | A % | B % |
|---|---|---|---|
| | 0.0 | 90 | 10 |
| | 20.0 | 10 | 90 |
| | 23.0 | 10 | 90 |
| | 24.0 | 90 | 10 |
| | 30.0 | 90 | 10 |
| | Re-equilibration time: 6 min | | |

| Flow rate | 1.0 ml/min |
|---|---|
| Detector | UV 220 nm |
| Diluent | ACN | a) 5-bromo-8-nitro-tetralin-1-one (I13)

A solution of potassium nitrate (1.15 eq., 13.83 g) dissolved in sulphuric acid (Conc., 5.0 rel. vol., 160 mL), was added (addition time 4-12 h, maintaining the temperature below 10° C.) to a solution of 5-bromotetralin-1-one (I12) (1.0 equiv., 26.77 g) in sulfuric acid (Conc., 5.0 rel. vol., 160 mL) under nitrogen. When the reaction was complete the reaction mixture was transferred to flask containing water (36 rel. vol., 1.15 L) adjusting the transfer rate to keep the temperature below 10° C. The resulting solid was filtered, washed with water (4.0 rel. vol., 128 mL) three times and then dried at ~40° C. for 24h. The dry cake was dissolved in a mixture of acetone (2.5 rel. vol., 80 mL) and water (0.38 rel. vol., 12.2 mL) heated to ~75° C. and then cooled to ~20° C. The resulting solid was removed by filtration. The solvent was swapped to ethanol by distillation and the solution volume reduced to a 2.0 rel. vol. (64 mL). The solution was cooled to ~25° C. and the resulting solid collected by filtration. The solid was washed with ethanol (1.0 Rel. Vol., 32 mL) then dried under vacuum at 40° C. to give 5-bromo-8-nitro-tetralin-1-one I13 (15.36 g, 40%) as a brown solid; RT 14.0 min Method 1 IPC, purity and assay method for bromo-8-nitro-tetralin-1-one.

| Instrument | Thermo U-3000 |
|---|---|
| Column | ACE Excel 3 C18-PFP (3.0 mm × 150 mm) |
| Oven | 40° C. |
| Mobile phase | A: 10 mM Ammomium Formate in water pH = 3.5 |
| | B: ACN |

| Gradient program | Time (min) | A % | B % |
|---|---|---|---|
| | 0.0 | 90 | 10 |
| | 20.0 | 10 | 90 |
| | 23.0 | 10 | 90 |
| | 24.0 | 90 | 10 |
| | 30.0 | 90 | 10 |
| | Re-equilibration time: 6 min | | |

| Flow rate | 1.0 ml/min |
|---|---|
| Detector | UV 220 nm |
| Diluent | ACN | b) N-(8-nitro-1-oxo-tetralin-5-yl)acetamide (I14)

A solution of bromo-8-nitro-tetralin-1-one (I13)(1.0 eq., 18.0 g, 90.6% ww), acetamide (1.2 eq., 4.72 g), tris(dibenzylideneacetone)dipalladium(0) (0.01 eq., 0.61 g) and potassium phosphate (1.4 eq., 19.8 g) in dioxane (15 rel. vol., 270 mL) under nitrogen was heated to ~70° C. When the reaction was complete the solution was cooled to ~20° C. and diluted with dioxane (5 rel. vol., 90.0 mL) and filtered. The solvent was swapped to ethanol and the volume reduced to a total reaction volume of 3 rel. vol. (54.0 mL). the solution was cooled to ~20° C. and the resulting solid collected by filtration and washed with MTBE (methyl tert-butyl ether) (1.0 rel. vol., 18.0 mL). The solid was dried under vacuum at 40° C. to give N-(8-nitro-1-oxo-tetralin-5-yl)acetamide 114 (10.0 g, 60.6%) as a dark yellow solid; RT 8.86 min.

c) N-(8-amino-1-oxo-tetralin-5-yl)acetamide (I15)

Palladium hydroxide on carbon (20% w/w, 0.15 eq., 5.25 g) was added to a solution of N-(8-nitro-1-oxo-tetralin-5-yl)acetamide (I14)(1.0 eq., 32.6 g) in methanol (40 rel. vol., 1250 mL). The reaction mixture was placed under a hydrogen atmosphere at ~40 psi, at ~40° C. for 8h. The hydrogen was removed and replaced with nitrogen and the catalyst was removed by filtration over cellulose, washing the cellulose with methanol (4.0 rel. vol., 130 mL). The solution volume was reduced to 4.0 rel. vol. by distillation and then diluted with MTBE (4 rel. vol, 130 mL). The resulting solid was collect by filtration, washed with MTBE (2 rel. vol., 65 mL) and dried under vacuum at 40° C. to give N-(8-amino-1-oxo-tetralin-5-yl)acetamide I15 (21.1 g, 77.8%) as a grey green solid; RT 5.44 min.

d) 5,8-diaminotetralin-1-one (I16)

A solution of N-(8-amino-1-oxo-tetralin-5-yl)acetamide (I15)(1.0 eq., 10.0 g) in hydrochloric acid (5M, 6.0 rel. vol., 60 mL), was held at ~90° C. for 3h. The temperature was reduced to 25° C. and sodium hydroxide (2M, 4.0 rel. vol., 40 mL) was added until pH 10.0 was achieved, maintaining the temperature 25° C. The resulting solid was collected by filtration and washed with water (2.0 rel. vol., 20 mL). The wet cake was dissolved in tetrahydrofuran (60 rel. vol., 600 mL) and filtered. The solution was concentrated to 5.0 rel. vol. and heptane (20 rel. vol., 200 mL) added. The solution was concentrated to 10.0 rel. vol. and further heptane (20 rel. vol., 200 mL) added, and then the volume reduce d to 10.0 rel. vol. again. The resulting solid was collected by filtration and washed with heptane (5.0 rel. vol., 50 mL). The solid was dried under vacuum at 40° C. for 17h to give 5,8-diaminotetralin-1-one (I16)(6.90 g, 82.7%) as a yellow solid; 1H NMR (400 MHz DMSO-d6) δ ppm 1.82 (m, 2H), 2.38 (t, J=2.0 Hz, 2H), 2.47 (t, J=2.0 Hz, 2H), 6.34 (d, J=2.0 Hz, 1H), 6.68 (d, J=2.0 Hz, 1H); RT 3.90 e) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11)

A solution of 5,8-diaminotetralin-1-one (I16)(1.0 eq., 5.0 g), (4S)-4-ethyl-4-hydroxy-7,8-dihydro-1H-pyrano[3,4-f]indolizine-3,6,10-trione (A3)(1.06 eq., 7.9 g), and pyridinium para-toluenesulfonate (1.0 eq., 7.2 g) in toluene (50.0 rel. vol., 250 mL) was held at 120° C. for 15 h. The volume of the solution was reduced to 2.0 rel. vol. and then diluted with acetonitrile (20 rel. vol., 100 mL) and water (20 rel. vol., 100 mL). The resulting slurry was filtered and the solid washed with aqueous acetonitrile (1:1, 20 rel. vol., 100 mL). The solid was slurried with aqueous methanol (water:MeOH 3:1, 40 rel. vol., 200 mL), filtered and washed with aqueous methanol (1:1, 20 rel. vol., 100 mL). The solid was slurried with water (60 rel. vol., 300 mL) at 50° C., filtered and washed with water (10 rel. vol., 50 mL). The solid was slurried with aqueous acetonitrile (water:acetonitrile, 1:3, 40 rel. vol., 200 mL) at 30° C., filtered and washed with aqueous acetonitrile (water:acetonitrile, 1:3, 5 rel. vol., 50 mL) and then dried under vacuum at 40° C. to give (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11) as white solid (5.0 g, 43.7%); RT 5.13.

Synthesis of 118 a) tert-butyl (S)-(2-((2-((1-((2-((4-amino-5-oxo-5,6,7,8-tetrahydronaphthalen-1-yl)amino)-2-oxoethyl)amino)-1-oxo-3-phenylpropan-2-yl)amino)-2-oxoethyl) amino)-2-oxoethyl) carbamate (I17)

Boc-GGFG-OH (227 mg, 0.52 mmol) and EEDQ (157 mg, 0.634 mmol) were solubilised in CH$_2$Cl$_2$ (25 mL) and the mixture stirred for 15 min, until the peptide has gone into solution. Compound I16 (100 mg, 0.56747 mmol) was subsequently added and the mixture left to stir until complete. After 1h, the reaction looked 90% complete by LVMC. The mixture has gone thicker as the product is crashing out. The mixture was left for another hour before vaccing down to dryness. The crude was taken up in Et$_2$O (50 mL). The solid was filtered and subsequently taken up in CH$_2$Cl$_2$ (50 mL) to purify further. The solid was filtered and dried to give product I17 (273 mg, 0.459 mmol, 80.9% Yield) as a grey solid. Analytical data: LCMS 3 min: ES$^+$=1.46 min, m/z 595.7 [M+H].$^+$.

b) (S)-2-(2-(2-aminoacetamido)acetamido)-N-(2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)-3-phenylpropanamide (I18)

Aniline I17 (450 mg, 1.045 mMol), lactone A5 (280 mg, 1.064 mMol) and pyridinium p-toluenesulfonate (273 mg, 1.086 mMol) were solubilised in toluene (20 mL) and the mixture was heated to 150° C. (high reflux). MeOH (4 mL) was added to help solubilise the mixture. After 7h the crude reaction was vacced down to dryness. The crude product was purified by silica gel chromatography (CHCl$_3$/MeOH, 100% to 65:35) to give product 118 (259 mg, 0.359 mMol, 78.1 yield). Analytical data: LCMS 3 min: ES+=1.17 min, m/z 722.8 [M+H].$^+$.

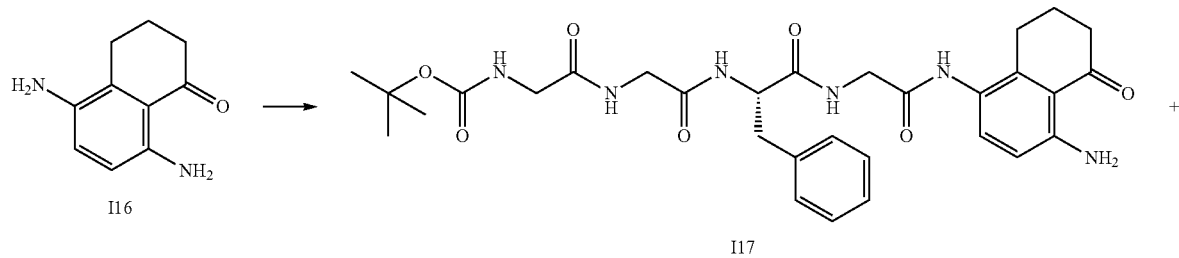

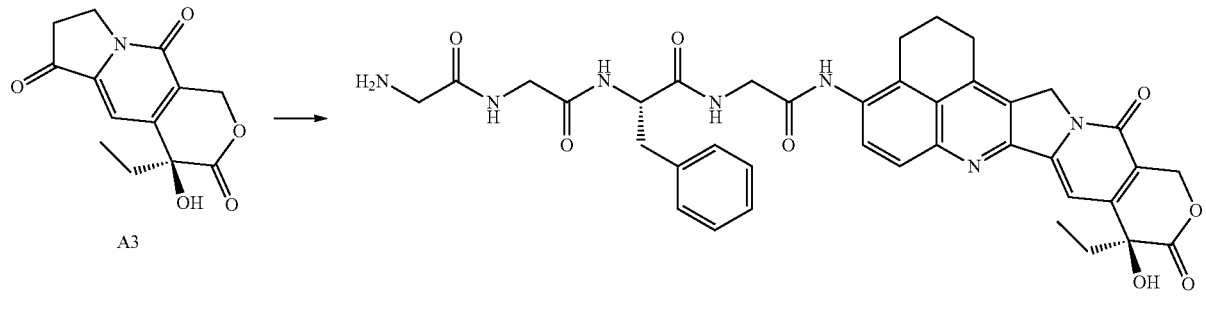

Alternative Synthesis of I16

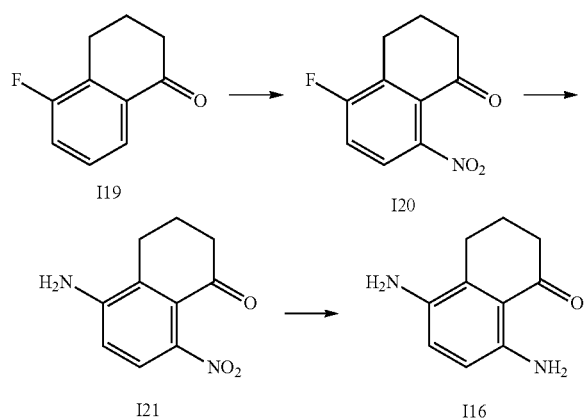

a) 5-Fluoro-8-nitro-tetralin-1-one (I20)

5-fluorotetralin-1-one 119 (4.7 g, 29 mmol) was solubilised in ½ the amount of sulfuric acid (120 mL) in a 3 neck round bottom flask. The mixture was stirred until all the solid has dissolved and then cooled to 0-5° C. In a dropping funnel, dissolve potassium nitrate (3 g, 29.6730 mmol) into the remaining half of sulfuric acid (120 mL) at 0-5° C. Slowly add to the SM mixture making sure to maintain the solution cool (45 min). Stir at 0-5° C. until complete. The reaction mixture was subsequently quenched with water (250 mL) and left to stir at 0-5° C. The solid was filtered and washed with water (50 mL). The solid was dried in a vacuum oven for 2h at 50° C. The crude solid was slurried in $Et_2O$ overnight before being cooled to 0° C. and filtered. The wet cake was washed with more cold $Et_2O$ (50 mL) and left to dry in a vacuum oven at 50° C. to give pure product I20 (5.5 g, 26 mmol, 92% yield) as a light pink ine powder. LCMS (Method B): $ES^+$=1.55 min, m/z 210.1 [M+H].$^+$.

b) 5-Amino-8-nitro-tetralin-1-one (I21)

Compound 120 (2.7 g, 13 mmol) was solubilised in $CH_3CN$ (2.5 mL) and $NH_4OH$ (21 mass %) in $H_2O$ (8 mL, 40 mmol) was added to a sealed pressure resistant tube and heated to 185° C. Once complete, the mixture was transferred to a round bottom flask and vacced down. The crude was purified by silica gel column chromatography ($CHCl_3$/MeOH; 100 to 99:1) to give pure product I21 (1.1 g, 5.3 mmol, 41% yield) as a black solid. LCMS (Method B): $ES^+$=1.34 min, m/z 207.1 [M+H].$^+$.

c) 5,8-diaminotetralin-1-one (I16)

Compound I21 (1.35 g, 6.55 mmol) was dissolved in a mixture of methanol (20 mL), $H_2O$ (1 mL) and formic acid (1 mL) at 0° C. Zinc (8.5 g, 130 mmol) was slowly added, making sure to keep the temperature below 40° C. A little more formic acid/$H_2O$ (0.5 mL) was added to push the reaction to completion. The reaction mixture was filtered, and the filtrate diluted with EtOAc and $CH_2Cl_2$ before being vacced down. The crude was dry loading onto silica gel column chromatography ($CHCl_3$/EtOAc; 100 to 7:3 then $CHCl_3$/MeOH; 99:1 to 98:2) to give pure product 116 (1.015 g, 5.760 mmol, 88.0% Yield). LCMS (Method B): ES+=0.2 min, m/z not observed.

Example 1

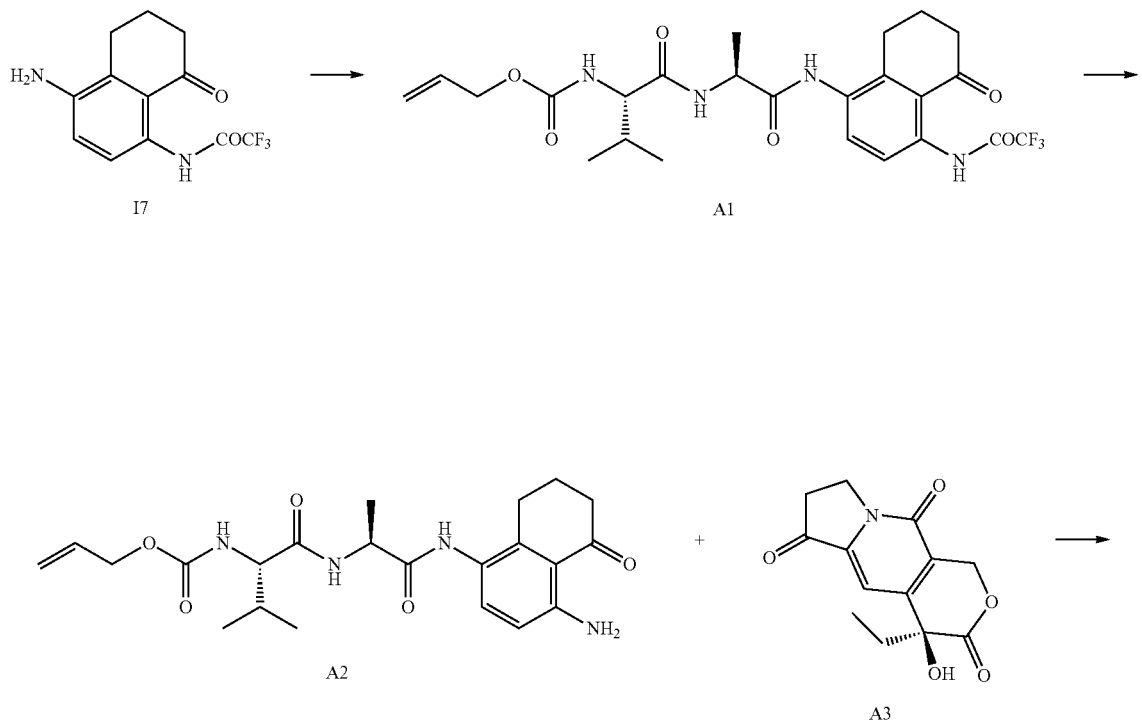

-continued

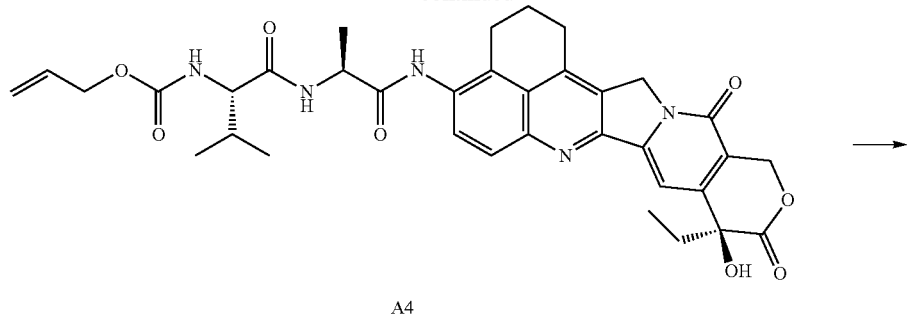

A4

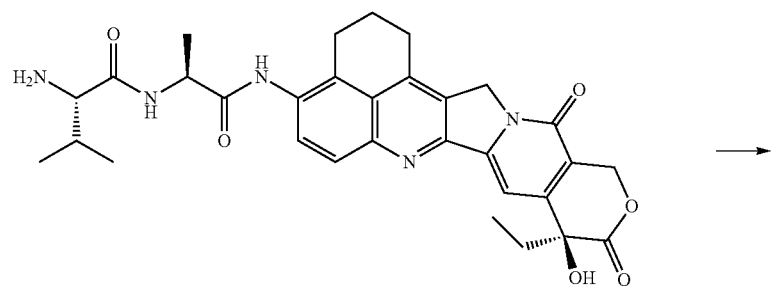

A5

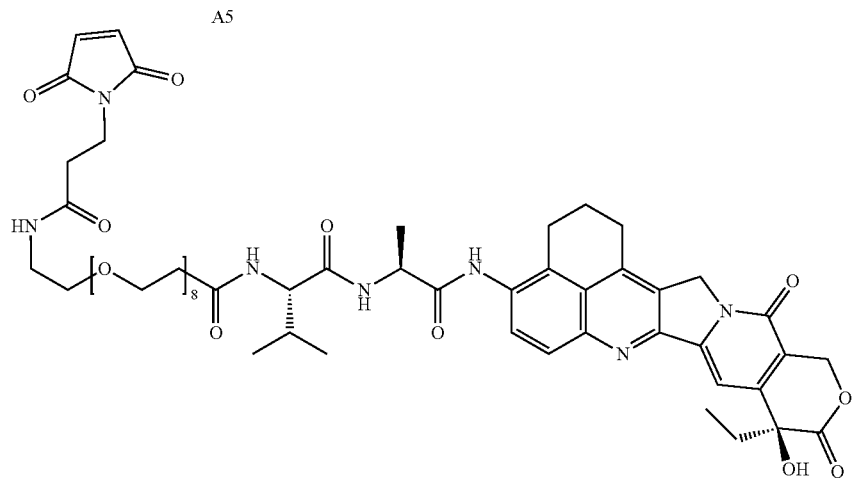

1 a) Allyl ((S)-3-methyl-1-oxo-1-(((S)-1-oxo-1-((5-oxo-4-(2,2,2-trifluoroacetamido)-5,6,7,8-tetrahydronaphthalen-1-yl)amino)propan-2-yl)amino)butan-2-yl)carbamate (A1)

DCC (6.54 g, 31.7 mMol) and HOPO (3.36 g, 30.2 mMol) were added to a solution of alloc-Val-Ala-OH (9.09 g, 31.7 mmol) and 17 (7.85 g, 28.8 mMol) in CH$_2$Cl$_2$ (300 mL) at 25° C. The resulting mixture was left to stir overnight. The white solid that formed during the reaction was filtered out and washed with cold CH$_2$Cl$_2$. The filtrate was washed with water (150 mL) and brine (150 mL). The organic layer was dried over MgSO$_4$, filtered and evaporated. The crude product was purified by silica gel chromatography (Hex/EtOAc, 60:40). Product A1 isolated was contaminated with co-eluting DCU (21.1 g, 140% yield). LC/MS (Method B): ES$^+$=1.81 min, m/z 527.6 [M+H].$^+$.

b) Allyl ((S)-1-(((S)-1-((4-amino-5-oxo-5,6,7,8-tetrahydronaphthalen-1-yl)amino)-1-oxopropan-2-yl)amino)-3-methyl-1-oxobutan-2-yl)carbamate (A2)

Protected aniline A1 (18 g, 34.19 mMol) was solubilised in a mixture of MeOH and H$_2$O 10:1 (165 mL) and K$_2$CO$_3$ was added (10 g, 72.36 mMol). The mixture was stirred at 50° C. until complete. The mixture was vacced down to almost dryness and the residue was taken up with CH$_2$Cl$_2$ and washed with H$_2$O and brine, before being dried over MgSO$_4$, filtered and evaporated. The crude product was purified by silica gel chromatography (CHCl$_3$/MeOH, 100% to 7:3). The isolated product A2 was contaminated with a co-eluting impurity (10.71 g, 73% yield). LC/MS (Method B): ES+=1.46 min, m/z 431.7 [M+H].$^+$.

c) Allyl ((S)-1-(((S)-1-(((S)-9-ethyl-9-hydroxy-10, 13-dioxo-2,3,9,10,13,15-hexahydro-1H,12H-benzo[de]pyrano[3',4':6,7]indolizino[1,2-b]quinolin-4-yl) amino)-1-oxopropan-2-yl)amino)-3-methylbutan-2-yl)carbamate (A4)

Aniline A2 (450 mg, 1.045 mMol), lactone A3 (280 mg, 1.064 mMol) and pyridinium p-toluenesulfonate (273 mg, 1.086 mMol) were solubilised in toluene (20 mL) and the mixture was heated to 130° C. (high reflux). Every now and then a few drops of MeOH is added to help solubilise the mixture. After 7h the crude reaction was vacced down to dryness. The crude product was purified by silica gel chromatography (CHCl$_3$/MeOH, 100% to 95:5) to give product A4 (360 mg, 52.3% yield). LC/MS (Method B): ES$^+$=1.51 min, m/z 658.8 [M+H].$^+$.

d) Allyl (S)-2-amino-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (A5)

Excess piperidine was added (642 µL) to a solution of A4 (543 mg, 0.82 mMol) and PdP(Ph$_3$)$_4$(89 mg, 0.08 mMol) in CH$_2$Cl$_2$ (15 mL). The mixture was allowed to stir at room temperature for 20 min, at which point the reaction had gone to completion (as monitored by LC/MS). The reaction mixture was diluted with CH$_2$Cl$_2$ (25 mL) and the organic phase was washed with H$_2$O (25 mL) and brine (25 mL). The organic phase was dried over MgSO$_4$, filtered and excess solvent removed by rotary evaporation under reduced pressure to afford crude product A5 which was used as such in the next step. LC/MS (Method B): ES$^+$=1.15 min, m/z 574.6 [M+H].$^+$.

e) 1-(3-(2,5-dioxo-2,5-dihydro-1H-pyrrol-1-yl)propanamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-3,6,9,12,15,18,21,24-octaoxaheptacosan-27-amide (1)

Pyridine (83 µL, 1.03 mMol) and Mal-dPEG$_8$-OTFP (767 mg, 1.03 mMol) were added to a solution of crude A5 (assumed 1.03 mMol) in dry CH$_2$Cl$_2$ (50 mL) under an argon atmosphere. The reaction was stirred overnight and as the reaction was not complete 0.5 eq. of Mal-dPEG$_8$-OTFP was added to try to push the reaction. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by reverse phase HPLC (gradient of H$_2$O/CH$_3$CN+0.05% FA) and freezedried to give 1 (1.189 g, 31% yield over 2 steps). LC/MS (Method B): ES+=1.43 min, m/z 1149.3 [M+H].$^+$. LC/MS (Method C): ES$^+$=5.37 min, m/z 1149.4 [M+H].$^+$.

Example 2

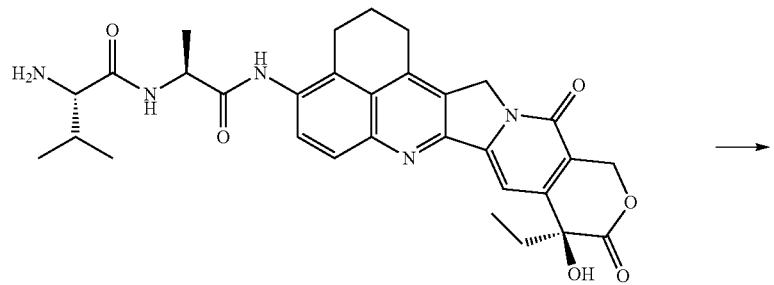

A5

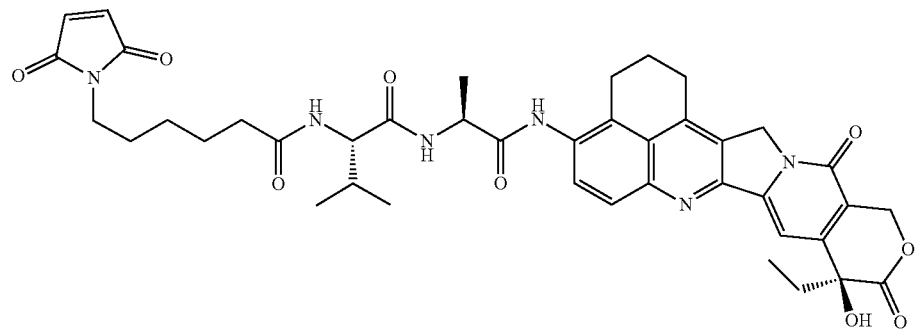

6-(2,5-dioxo-2,5-dihydro-1H-pyrrol-1-yl)-N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)hexanamide (2)

Mal-caproic acid (56 mg, 0.26 mMol) and EDCI.HCl (51 mg, 0.26 mMol) were added to a solution of crude A5 (assumed 0.26 mMol) in dry $CH_2Cl_2$ (20 mL) under an argon atmosphere. The reaction was stirred overnight and as the reaction was incomplete, another 0.5 eq of Mal-caproic acid and EDCI.HCl were added. The reaction was diluted with $CH_2Cl_2$ (25 mL) and the organic phase was washed with $H_2O$ (2×50 mL) and brine before being dried over $MgSO_4$, filtered and excess solvent removed by rotary evaporation under reduced pressure by rotary evaporation under reduced pressure. The crude was purified by silica gel column chromatography ($CHCl_3$/MeOH 95:5) to give 2 (31.6 mg, 20% yield over 2 steps). LC/MS (Method B): $ES^+$=1.56 min, m/z 767.8 [M+H].$^+$. LC/MS (Method C) 15 min: $ES^+$=6.05 min, m/z 767.8 [M+H].$^+$.

Example 3

(S)-2-(2-(2-(2-(2-azidoethoxy)ethoxy)ethoxy)acetamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (3)

Azido-$dPEG_3$-acid (77.5 mg, 0.31 mMol) and EDCI.HCl (60 mg, 0.31 mMol) were added to a solution of crude A5 (assumed 0.31 mMol) in dry $CH_2Cl_2$ (20 mL) under an argon atmosphere. The reaction was stirred overnight and as the reaction was incomplete, another 0.5 eq. of azido-$dPEG_3$-OH and EDCI.HCl were added. The reaction was diluted with $CH_2Cl_2$ (25 mL) and the organic phase was washed with $H_2O$ (2×50 mL) and brine before being dried over $MgSO_4$, filtered and excess solvent removed by rotary evaporation under reduced pressure by rotary evaporation under reduced pressure. The crude was purified by preparative HPLC and the fractions were freezedried to give pure 3 (92.2 mg, 24.7% yield over 2 steps). LC/MS (Method B): $ES^+$=1.69 min, m/z 789.9 [M+H].$^+$. LC/MS (Method C): $ES^+$=6.68 min, m/z 790.0 [M+H].$^+$.

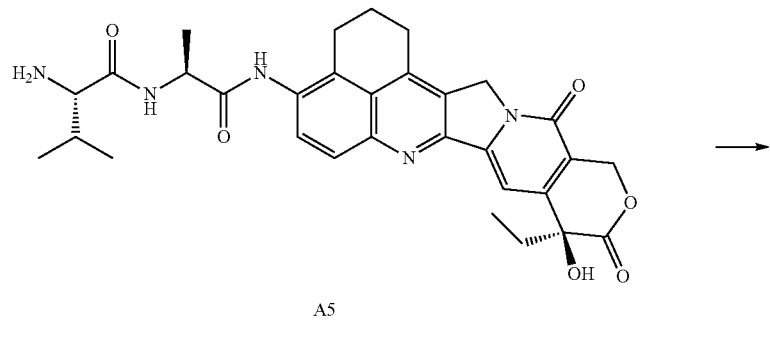

A5

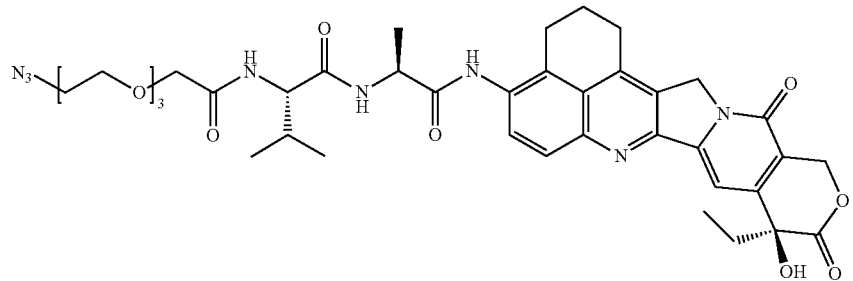

3

Example 4

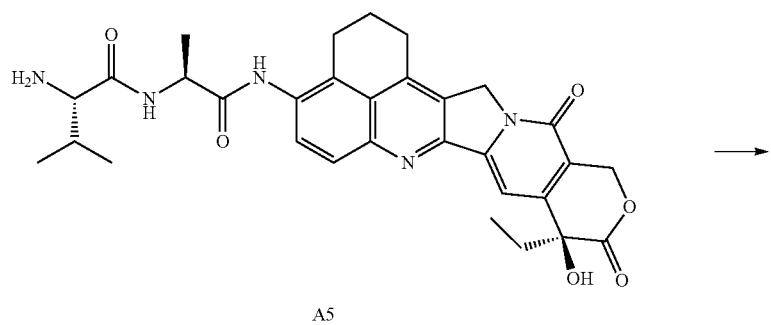

A5

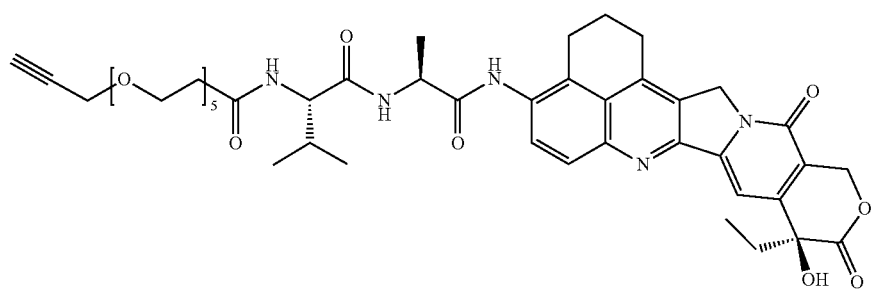

4

N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-4,7,10,13,16-pentaoxanonadec-18-ynamide (4)

Propargyl-dPEG$_5$-acid (56 mg, 0.19 mMol) and EDCI.HCl (37 mg, 0.19 mMol) were added to a solution of crude A5 (assumed 0.19 mMol) in dry CH$_2$Cl$_2$ (10 mL) under an argon atmosphere. The reaction was stirred overnight and as the reaction was incomplete, another 0.5 eq. of Propargyl-dPEG$_5$-OH and EDCI.HCl were added. The reaction was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by preparative HPLC and the fractions were freeze dried to give pure 4 (22 mg, 16.7% yield over 2 steps). LC/MS (Method B): ES$^+$=1.54 min, m/z 860.9 [M+H].$^+$. LCMS (Method C): ES$^+$=5.57 min, m/z 860.9 [M+H].$^+$.

Example 5

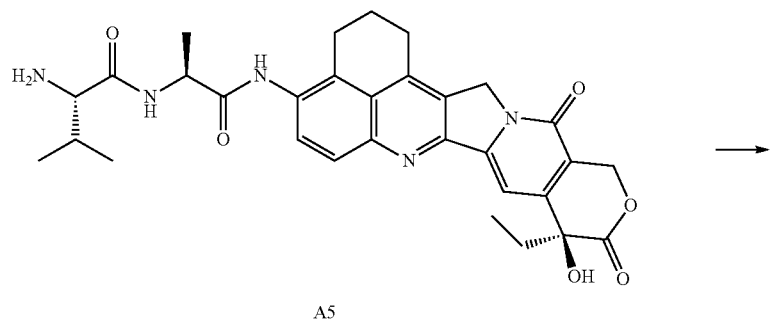

A5

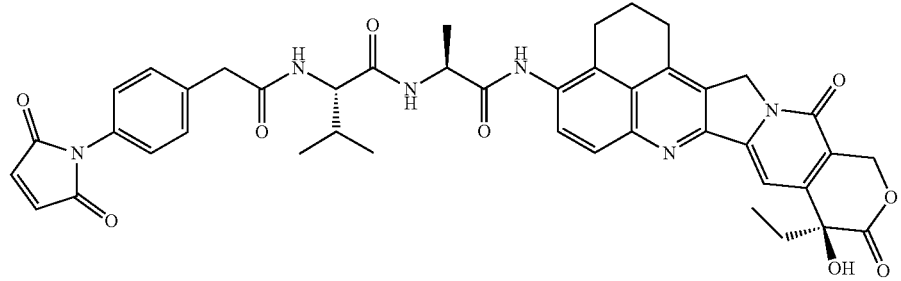

5

(S)-2-(2-(4-(2,5-dioxo-2,5-dihydro-1H-pyrrol-1-yl)phenyl)acetamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)-3-methylbutanamide (5)

PM-acetic-OSu (64 mg, 0.19 mMol) was added to a solution of crude A5 (assumed 0.19 mMol) in dry CH$_2$Cl$_2$ (10 mL) under an argon atmosphere. The reaction was not proceeding so DIPEA (51 μL, 0.28 mMol) was added. The reaction was stirred until complete. The mixture was diluted with CH$_2$Cl$_2$ (25 mL) and the organic phase was washed with H$_2$O (2×50 mL) and brine before being dried over MgSO$_4$, filtered and excess solvent removed by rotary evaporation under reduced pressure by rotary evaporation under reduced pressure. The crude was purified by preparative HPLC and the fractions were freezedried to give pure 5 (2.5 mg, 1.6% yield over 2 steps). LC/MS (Method B): ES$^+$=1.54 min, m/z 787.7 [M+H].$^+$. LC/MS (Method C): ES$^+$=5.61 min, m/z 787.8 [M+H].$^+$.

Example 6

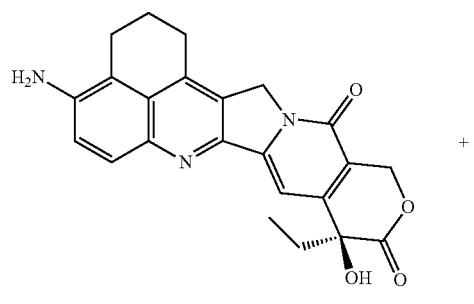

I11

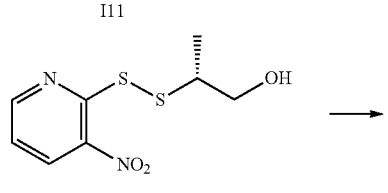

A6

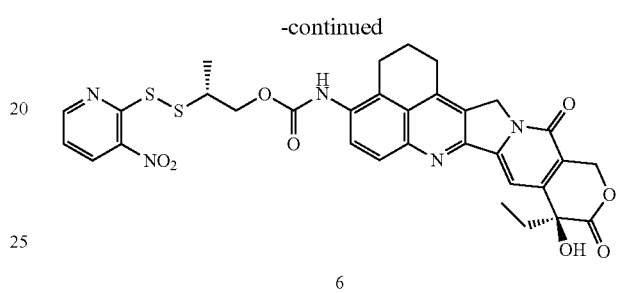

6

(R)-2-((3-nitropyridin-2-yl)disulfaneyl)propyl ((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)carbamate (6)

(i) (2R)-2-[(3-nitro-2-pyridyl)disulfanyl]propan-1-ol A6 (25 mg, 0.1015 mmol, 1.0 eq.) was dissolved in dichloromethane (1 mL). Pyridine (8.5 μL, 0.11 mmol, 1.0 eq.), then triphosgene (11 mg, 0.0370685 mmol, 0.33 eq.) were added and the mixture stirred under Ar for 45 min, whereupon LCMS (Et$_2$NH quench) indicated the formation of the corresponding carbamate.

(ii) (S)-4-amino-9-ethyl-9-hydroxy-1,2,3,9,12,15-hexahydro-10H,13H-benzo[de]pyrano[3',4':6,7]indolizino[1,2-b]quinoline-10,13-dione (I11) (43 mg, 0.09026 mmol, 1.0 eq.) was dissolved in dichloromethane (2 mL), N,N-diisopropylethylamine (42 μL, 0.241 mmol, 2.7 eq.) and pyridine (25 μL, 0.309 mmol, 3.4 eq.). The reaction mixture from step (i) was added and the mixture stirred for 30 min, whereupon LCMS indicated the reaction was complete. The reaction mixture was concentrated in vacuo and purified by isolera chromatography (0-4% MeOH in CH$_2$Cl$_2$) to afford 6 (22 mg, 0.03256 mmol, 36% Yield, QC=96.8%) as a yellow solid. LC/MS (Method B): RT=1.86 min, 676.6 [M+H]$^+$.

Example 7

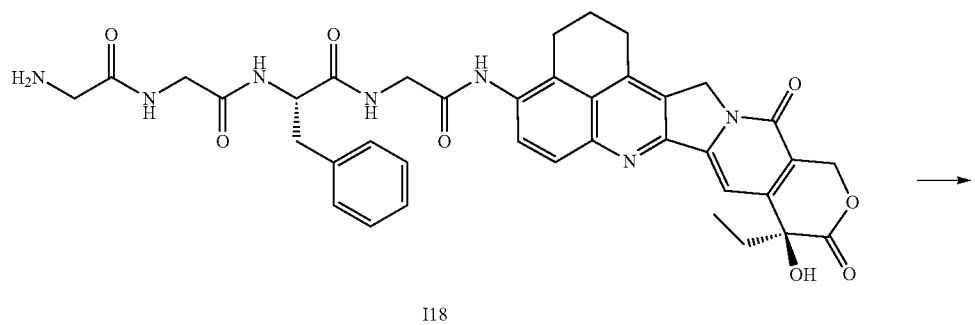

I18

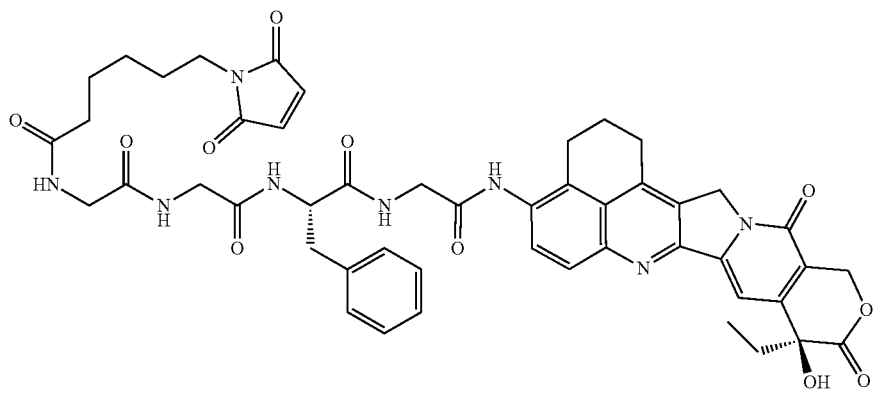

7

6-(2,5-dioxo-2,5-dihydro-1H-pyrrol-1-yl)-N-(2-((2-(((S)-1-((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)amino)-1-oxo-3-phenylpropan-2-yl)amino)-2-oxoethyl)amino)-2-oxoethyl)hexanamide (7)

Compound I18 (259 mg, 0.3588 mmol) was solubilised in CH$_2$Cl$_2$ (25 mL). The starting material was not soluble at all so DMA (1 mL) was added. As no improvement was observed, DIPEA (68 μL, 0.390 mmol) was added and all the solid went in solution. Maleimide caproic acid (69 mg, 0.358 mmol) was added and the mixture left to stir at r.t. overnight and which point LCMS analysis revealed the reaction to be complete. The reaction mixture was quenched with MeOH (2 mL) and vacced down to dryness. The crude product was purified by preparative HPLC and subsequently freezedried to give compound 7 as an ochre solid (38.2 mg, 11% yield). Analytical data: LCMS 3 min: ES$^+$=1.47 min, m/z 916.2 [M+H].$^+$ LCMS 15 min: ES$^+$=5.46 min, m/z 916.1 [M+H].$^+$.

Example 8

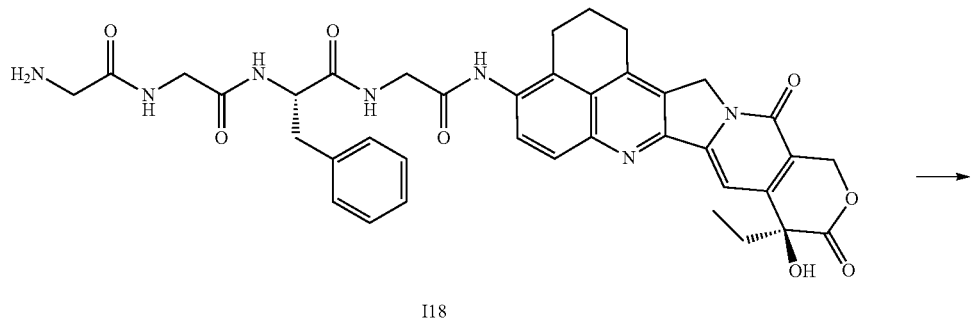

I18

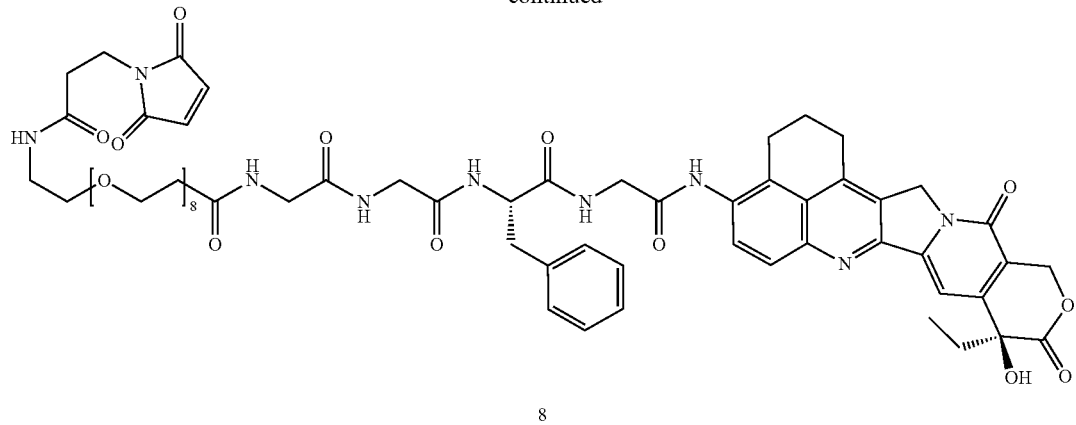

8

1-(3-(2,5-dioxo-2,5-dihydro-1H-pyrrol-1-yl)propanamido)-N-(2-((2-(((S)-1-((2-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-2-oxoethyl)amino)-1-oxo-3-phenylpropan-2-yl)amino)-2-oxoethyl)amino)-2-oxoethyl)-3,6,9,12,15,18,21,24-octaoxaheptacosan-27-amide (8)

Compound I18 (70 mg, 0.096 mmol) was solubilised in CH$_2$Cl$_2$ (5 mL). The starting material was not soluble at all so DMA (0.5 mL) was added. As no improvement was observed, DIPEA (19 µL, 0.106 mmol) was added and all the solid went in solution. Mal-dPEG$_8$-OH (63 mg, 0.106 mmol) and EDCI.HCl (19 mg, 0.099 mMol) were added and the mixture left to stir at r.t. overnight and which point LCMS analysis revealed the reaction to be complete. The reaction mixture was quenched with MeOH (2 mL) and vacced down to dryness. The crude product was purified by preparative HPLC and subsequently freezedried to give 8 as an ochre solid (30 mg, 24% yield). LCMS 3 min: ES$^+$=1.44 min, m/z 1297.6 [M+H].$^+$.

Example 9—Alternatie Synthesis of 1

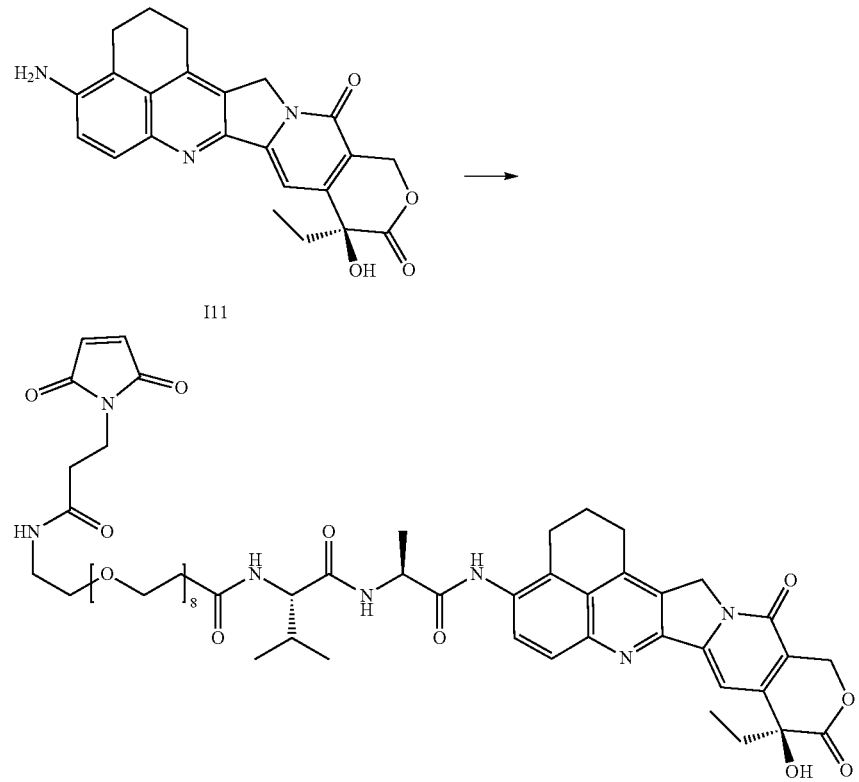

(S)-4-amino-9-ethyl-9-hydroxy-1,2,3,9,12,15-hexahydro-10H,13H-benzo[de]pyrano[3',4':6,7]indolizino[1,2-b]quinoline-10,13-dione I11 (371 mg, 0.779 mmol, 1.0 eq.) was dissolved in dichloromethane (30 mL). N,N-diisopropylethylamine (69 μL, 0.396 mmol, 0.51 eq.), and (2S)-2-[[(2S)-2-[3-[2-[2-[2-[2-[2-[2-[2-[3-(2,5-dioxopyrrol-1-yl)propanoylamino]ethoxy]ethoxy]ethoxy]ethoxy]ethoxy]ethoxy]ethoxy]propanoylamino]-3-methyl-butanoyl]amino]propanoic acid (664 mg, 0.871 mmol, 1.1 eq.) in N,N-dimethylacetamide (10 mL) were added, followed by EDCI.HCl (226 mg, 1.18 mmol, 1.5 eq.) and the mixture stirred for 2 h, whereupon LCMS indicated good conversion, but that the reaction had stalled. The reaction mixture was warmed to 30° C. and stirred for 30 min, LCMS indicated no change so CH$_2$Cl$_2$ was removed in vacuo and Et$_2$O added to the resulting DMA solution. The precipitated oil was collected, Et$_2$O removed in vacuo and the precipitation process repeated. The combined precipitates were purified by HPLC (10-60% B in A over 13 min) to afford 1 (200 mg, 0.174 mmol, 98% purity, 22% Yield) as a yellow residue after freeze-drying. LC/MS (method A): retention time 1.44 mins (ES$^+$) m/z 1149 [M+H]$^{+1}$H NMR (600 MHz, Chloroform-d) δ 8.81 (s, 1H), 7.83 (s, 2H), 7.48 (s, 1H), 7.18 (dd, J=18.7, 7.5 Hz, 2H), 6.69 (s, 2H), 6.43 (s, 1H), 5.68 (d, J=16.1 Hz, 1H), 5.27 (d, J=16.1 Hz, 1H), 5.03 (d, J=18.4 Hz, 1H), 4.90 (d, J=18.4 Hz, 1H), 4.75 (p, J=7.2 Hz, 1H), 4.32 (dd, J=7.4, 5.8 Hz, 1H), 4.05 (s, 1H), 3.83 (t, J=7.2 Hz, 3H), 3.78-3.68 (m, 3H), 3.68-3.57 (m, 31H), 3.53 (t, J=5.1 Hz, 3H), 3.40 (q, J=5.3 Hz, 2H), 3.06-2.91 (m, 3H), 2.84 (dt, J=16.3, 6.2 Hz, 1H), 2.63 (ddd, J=14.8, 8.5, 4.2 Hz, 1H), 2.57-2.44 (m, 4H), 2.30 (dq, J=13.4, 6.7 Hz, 1H), 2.10 (p, J=6.4 Hz, 3H), 1.91 (ddt, J=16.8, 14.3, 7.2 Hz, 3H), 1.54 (d, J=7.1 Hz, 3H), 1.02 (dd, J=15.5, 6.9 Hz, 10H).

Example 10—Alternate Synthesis of A2

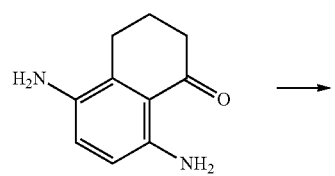

I16

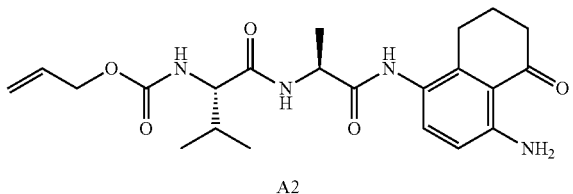

A2

Allyl ((S)-1-(((S)-1-((4-amino-5-oxo-5,6,7,8-tetrahydronaphthalen-1-yl)amino)-1-oxopropan-2-yl)amino)-3-methyl-1-oxobutan-2-yl)carbamate (A2)

EDCI.HCl (7.71 g, 31.2 mMol) was added to a solution of alloc-Val-Ala-OH (8.49 g, 31.2 mmol) in CH$_2$Cl$_2$ (200 mL) and stirred for 15 min or until solubilised. 116 (5 g, 28.3 mMol) was subsequently added and the resulting mixture was left to stir until the reaction was completed. The volatiles were removed under reduced pressure. The crude product was taken up in Et$_2$O (50 mL) and the mixture sonicated for 3 min. The solid was filtrated and taken up again in CH2Cl2 (50 mL), sonicated for 3 min and filtered again to give pure product A2 as a grey solid (12.21 g, 79% yield). LC/MS (Method B): ES$^+$=1.47 min, m/z 431.5 [M+H].$^+$.

Example 11

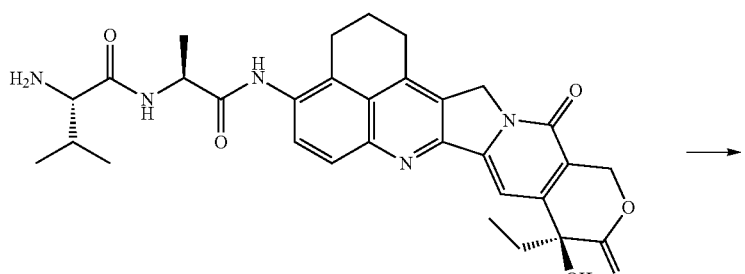

A5

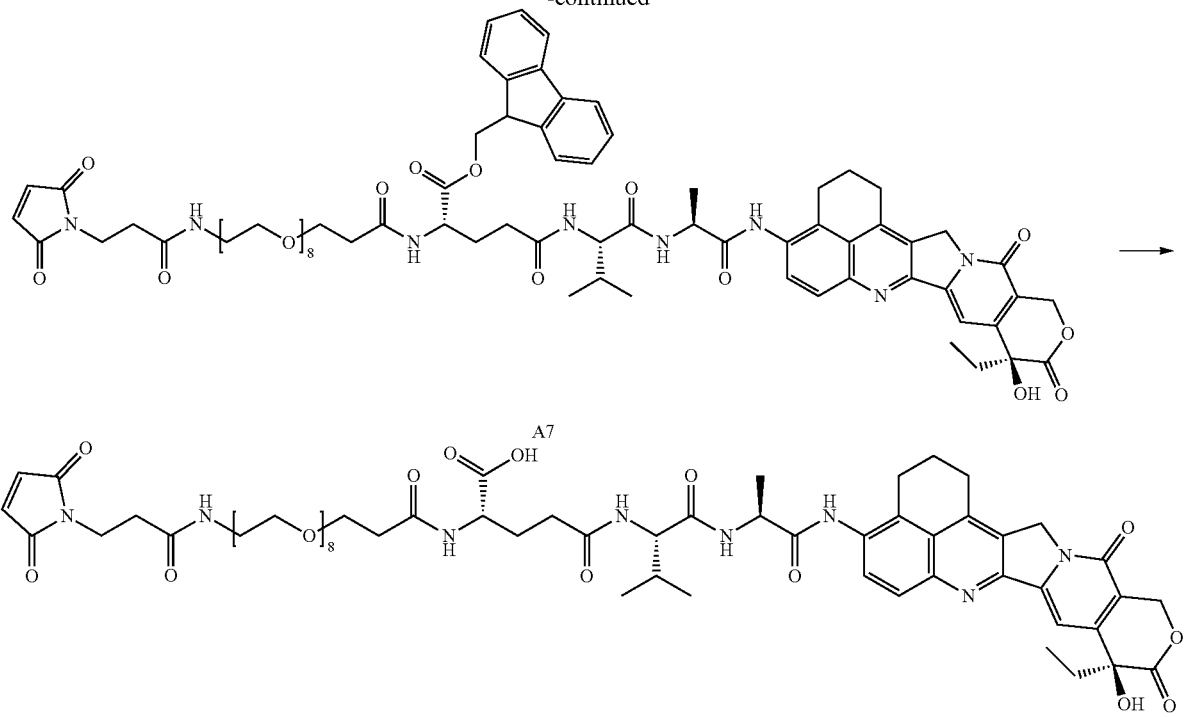

a) (9H-fluoren-9-yl)methyl N2-(1-(2,5-dioxo-2,5-dihydro-1H-pyrrol-1-yl)-3-oxo-7,10,13,16,19,22,25,28-octaoxa-4-azahentriacontan-31-oyl)-N5-((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-L-glutaminate (A7)

EDCI.HCl (0.10 mmol, 1.2 eq) was added to a solution of A5 (0.087 mmol, 1.0 eq) and Mal-PEG$_8$-Glu-OH (0.10 mmol, 1.2 eq) in DCM (5 mL) and the resulting mixture stirred at room temperature overnight. The reaction mixture was evaporated to dryness and purified by column (8-12% MeOH/DCM) to leave the product as a white solid. Yield=80 mg (63%). LC/MS (Method B) rt 1.66 min m/z (1456.2) M+H.

b) N2-(1-(2,5-dioxo-2,5-dihydro-1H-pyrrol-1-yl)-3-oxo-7,10,13,16,19,22,25,28-octaoxa-4-azahentriacontan-31-oyl)-N5-((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-L-glutamine (9)

1-Methylpyrrolidine (200 µL) was added to a solution of A7 (0.06 mmol) in DMF (0.8 mL) and stirred at room temperature for 10 mins. The solvent was removed under vacuum and the residue purified by prep HPLC (30% MeCN/water+0.05% formic acid over 8.5 mins). Fractions containing product were freeze dried to give the product as an off-white solid. Yield=23 mg (30%). LC/MS (Method B) rt 1.43 min m/z (1278.4) M+H.

Example 12—Conjugation

Herceptin-C239i Antibody

Herceptin antibodies were engineered to have cysteine inserted between the 239 and 240 positions were produced following the methods described in Dimasi, N., et al., Molecular Pharmaceutics, 2017, 14, 1501-1516 (DOI: 10.1021/acs.molpharmaceut.6b00995).

ConjA

A 50 mM solution of DL-dithiothreitol (DTT) in phosphate-buffered saline pH 7.4 (PBS) was added (150 molar equivalent/antibody, 40 micromoles, 800 µL) to a 10 mL solution of Herceptin-C239i antibody (40 mg, 267 nanomoles) in reduction buffer containing PBS and 1 mM ethylenediaminetetraacetic acid (EDTA) and a final antibody concentration of 4.0 mg/mL. The reduction mixture was allowed to react at room temperature for 4 hours 45 minutes (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 20 molar equivalent/antibody, 5.33 micromoles, 106.7 µL) in DMSO was added and the reoxidation mixture was allowed to react for 16 hours at room temperature with gentle (60 rpm) shaking at an antibody concentration of 4 mg/mL (or more DHAA added and reaction left for longer until full reoxidation of the cysteine thiols to reform the inter-chain cysteine disulfides is observed by UHPLC). The reoxidation mixture was then sterile-filtered and diluted in a conjugation buffer containing PBS and 1 mM EDTA for a final antibody concentration of 3.6 mg/mL. Compound 1 was added as a DMSO solution (10 molar equivalent/antibody, 1.33 micromoles, in 0.55 mL DMSO) to 5.0 mL of this reoxidised antibody solution (20 mg, 133 nanomoles) for a 10% (v/v) final DMSO concentration. The solution was mixed for 2 hours at room temperature, then the conjugation was quenched by addition of N-acetyl cysteine (6.67 micromoles, 67 μL at 100 mM), then purified by spin filtration into PBS using a 15 mL Amicon Ultracell 30 kDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjA at 214 nm and 330 nm (Compound 1 specific) shows unconjugated light chains and a mixture of unconjugated heavy chains and heavy chains attached to a single molecule of Compound 1, consistent with a drug-per-antibody ratio (DAR) of 1.89 molecules of Compound 1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjA at 280 nm shows a monomer purity of 98%. UHPLC SEC analysis gives a concentration of final ConjA at 2.14 mg/mL in 6.5 mL, obtained mass of ConjA is 13.9 mg (70% yield).

ConjA*

A 10 mM solution of Tris(2-carboxyethyl)phosphine (TCEP) in phosphate-buffered saline pH 7.4 (PBS) was added (10 molar equivalent/antibody, 400 nanomoles, 40 μL) to a 2.4 mL solution of Tratuzumab antibody (6 mg, 40 nanomoles) in reduction buffer containing PBS and 1 mM ethylenediaminetetraacetic acid (EDTA) and a final antibody concentration of 2.5 mg/mL. The reduction mixture was allowed to react at room temperature for 16 hours (or until full reduction is observed by UHPLC) in an orbital shaker with gentle (60 rpm) shaking. The reduced antibody solution was buffer exchanged (to remove all the excess reducing agent), via spin filter centrifugation, into a conjugation buffer containing PBS and 1 mM EDTA for a final antibody concentration of 2.0 mg/mL. Compound 1 was added as a DMSO solution (20 molar equivalent/antibody, 400 nanomoles, in 0.15 mL DMSO) to 1.35 mL of this reduced antibody solution (3 mg, 20 nanomoles) for a 10% (v/v) final DMSO concentration. The solution was mixed for 2 hours at room temperature, then the conjugation was quenched by addition of N-acetyl cysteine (2 micromoles, 20 μL at 100 mM), then purified via spin filter centrifugation using a 15 mL Amicon Ultracell 30 KDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjA* at 214 nm and 330 nm (Compound 1 specific) shows a mixture of unconjugated light chains, light chains attached to a single molecule of Compound 1, unconjugated heavy chains and heavy chains attached to up to three molecules of Compound 1, consistent with a drug-per-antibody ratio (DAR) of 7.89 molecules of Compound 1 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjA* at 280 nm shows a monomer purity of 98.5%. UHPLC SEC analysis gives a concentration of final ConjA* at 2.02 mg/mL in 1.25 mL, obtained mass of ConjA* is 2.5 mg (84% yield).

ConjB

A 10 mM solution of Tris(2-carboxyethyl)phosphine (TCEP) in phosphate-buffered saline pH 7.4 (PBS) was added (10 molar equivalent/antibody, 3.56 micromoles, 356 μL) to a 11.1 mL solution of Tratuzumab antibody (53.4 mg, 356 nanomoles) in reduction buffer containing PBS, pH 7.4 and 1 mM ethylenediaminetetraacetic acid (EDTA) and a final antibody concentration of 4.84 mg/mL. The reduction mixture was allowed to react at 37° C. for 1 hour 30 minutes (or until full reduction is observed by UHPLC) in an orbital shaker with gentle (60 rpm) shaking. Compound 2 was added as a DMSO solution (15 molar equivalent/antibody, 5.1 micromoles, in 1.2 mL DMSO) to 10.5 mL of this reduced antibody solution (50.8 mg, 339 nanomoles) for a 10% (v/v) final DMSO concentration. The solution was mixed for 1 hour 30 minutes at room temperature, then the conjugation was quenched by addition of N-acetyl cysteine (25.4 micromoles, 254 μL at 100 mM), then purified on an AKTA™ Start FPLC using a GE Healthcare HiLoad⁷M 26/600 column packed with Superdex 200 PG, eluting with 2.6 mL/min PBS. Fractions corresponding to ConjB monomer peak were pooled, concentrated and buffer exchanged into 25 mM Histidine 205 mM Sucrose pH 6.0 buffer using a 15 mL Amicon Ultracell 50 KDa MWCO spin filter, sterile-filtered and analysed.

UHPLC analysis on a Shimadzu Prominence system using a Thermo Scientific MAbPac 50 mm×2.1 mm column eluting with a gradient of water and acetonitrile on a reduced sample of ConjB at 214 nm and 330 nm (Compound 2 specific) shows a mixture of unconjugated light chains, light chains attached to a single molecule of Compound 2, unconjugated heavy chains and heavy chains attached to up to three molecules of Compound 2, consistent with a drug-per-antibody ratio (DAR) of 7.93 molecules of Compound 2 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjB at 280 nm shows a monomer purity of 98.9%. UHPLC SEC analysis gives a concentration of final ConjB at 2.4 mg/mL in 16 mL, obtained mass of ConjB is 38.4 mg (84% yield).

ConjC

A 10 mM solution of Tris(2-carboxyethyl)phosphine (TCEP) in phosphate-buffered saline pH 7.4 (PBS) was added (40 molar equivalent/antibody, 11.2 micromoles, 1.12 mL) to a 20 mL solution of Herceptin-C239i antibody (42 mg, 280 nanomoles) in reduction buffer containing PBS and 1 mM ethylenediaminetetraacetic acid (EDTA) and a final antibody concentration of 2.1 mg/mL. The reduction mixture was allowed to react at room temperature for 16 hours (or until full reduction is observed by UHPLC) in an orbital shaker with gentle (60 rpm) shaking. The reduced antibody was buffer exchanged, via spin filter centrifugation, into a reoxidation buffer containing PBS and 1 mM EDTA to remove all the excess reducing agent. A 50 mM solution of dehydroascorbic acid (DHAA, 30 molar equivalent/antibody, 7.0 micromoles, 141 μL) in DMSO was added to 22 mL of this reduced buffer exchanged antibody (35.2 mg, 235 nanomoles) and the reoxidation mixture was allowed to react for 2 hours and 30 minutes at room temperature with gentle (60 rpm) shaking at an antibody concentration of 1.6 mg/mL (or more DHAA added and reaction left for longer until full reoxidation of the cysteine thiols to reform the inter-chain cysteine disulfides is observed by UHPLC). The reoxidation mixture was then sterile-filtered. Compound 6 was added as a DMSO solution (20 molar equivalent/antibody, 2.3 micromoles, in 1.36 mL DMSO) to 11.0 mL of this reoxidised antibody solution (17.6 mg, 117 nanomoles) pH adjusted with 1.22 mL of 1 M Sodium Bicarbonate for a 10% (v/v) final DMSO concentration and 10% (v/v) 1 M sodium bicarbonate. The solution was left to react at room temperature for 2 hours with gentle shaking. Then the conjugation was quenched by addition of N-acetyl cysteine (12 micromoles, 117 μL at 100 mM), then purified and buffer exchanged into 25 mM Histidine 205 mM Sucrose pH 6.0 buffer using a 15 mL Amicon Ultracell 50 kDa MWCO spin filter, sterile-filtered and analysed.

UHPLC analysis on a Shimadzu Prominence system using a Sepax Proteomix HIC Butyl-NP5 4.6×35 mm 5 μm column eluting with a gradient of 25 mM sodium phosphate, 1.5 M ammonium sulphate pH 7.4 buffer and 20% acetonitrile (v/v) in 25 mM sodium phosphate pH 7.4 buffer on intact sample of ConjC at 214 nm and 330 nm (Compound 6 specific) showed unconjugated and conjugated antibody attached to one or two molecules of Compound 6, consistent with a drug-per-antibody ratio (DAR) of 1.42 molecules of Compound 6 per antibody.

UHPLC analysis on a Shimadzu Prominence system using a Tosoh Bioscience TSKgel SuperSW mAb HTP 4 μm 4.6×150 mm column (with a 4 μm 3.0×20 mm guard column) eluting with 0.3 mL/minute sterile-filtered SEC buffer containing 200 mM potassium phosphate pH 6.95, 250 mM potassium chloride and 10% isopropanol (v/v) on a sample of ConjC at 280 nm shows a monomer purity of 98%. UHPLC SEC analysis gives a concentration of final ConjC at 1.06 mg/mL in 10.1 mL, obtained mass of ConjC is 10.7 mg (61% yield).

Example 13—In Vitro Assay

Solid test material was dissolved in DMSO to a 2 mM stock solution, from which eight serial dilutions were made at a 1:10 ratio in DMSO and stored at −20° C. until use.

Adherent NCI-N87 cells were washed with D-PBS and detached with Trypsin-EDTA, cell density and viability were then determined in duplicate by Trypan blue exclusion assay using an automated cell counter (LUNA-II™). Cell suspension was diluted to $1 \times 10^5$ cells/ml in growth media (RPMI 1640 with Glutamax+10% (v/v) HyClone™ Fetal Bovine Serum) and vortexed before dispensing 2 mL per well into sterile 3 mL polypropylene plates. Warhead dilutions were then dispensed into the appropriate wells at 10 μl/well and mixed by repeat pipetting. For control wells 10 μl of DMSO was dispensed onto 2 mL cell suspension, and thoroughly mixed. 100 μl of each sample was then aliquoted into 2 replicate wells of a sterile flat 96-well microplate and incubated in a 37° C. CO₂-gassed (5%) incubator. At the end of the incubation period time (7 days), cell viability was measured by CellTiter 96 ™ aqueous One (MTS) assay, which was dispensed at 20 μl/well and incubated for 4 hours at 37° C., 5% $CO_2$. Plates were then read on an EnVision™ Multi-label Plate Reader (Perkin Elmer) using absorbance at 490 nm.

Cell survival percentage was calculated from the mean absorbance of the 2 replicate wells for each sample, compared to the mean absorbance in the two control wells treated with DMSO only (100%). The $IC_{50}$ was determined by fitting each data set to sigmoidal dose-response curves with a variable slope using the non-linear curve fit algorithm on the GraphPad Prism software (San Diego, Calif.).

All the experiments in this report were carried out and tested in three independent experiments. Data are reported as the mean of the three independent replicates.

|  | $IC_{50}$ (nM) |
|---|---|
| I11 | 0.3854 |

Example 14—ADC In Vitro Assay

The concentration and viability of cells from a sub-confluent (80-90% confluency) T75 flask are measured by trypan blue staining, and counted using the LUNA-II™ Automated Cell Counter. Cells were diluted to $2 \times 10^5$/ml, dispensed (50 μl per well) into 96-well flat-bottom plates.

A stock solution (1 ml) of antibody drug conjugate (ADC) (20 μg/ml) was made by dilution of filter-sterilised ADC into cell culture medium. A set of 8×10-fold dilutions of stock ADC were made in a 24-well plate by serial transfer of 100 μl into 900 μl of cell culture medium. ADC dilution was dispensed (50 μl per well) into 4 replicate wells of the 96-well plate, containing 50 μl cell suspension seeded the previously. Control wells received 50 μl cell culture medium. The 96-well plate containing cells and ADCs was incubated at 37° C. in a $CO_2$-gassed incubator for the exposure time.

At the end of the incubation period, cell viability was measured by MTS assay. MTS (Promega) was dispensed (20 μl per well) into each well and incubated for 4 hours at 37° C. in the $CO_2$-gassed incubator. Well absorbance was measured at 490 nm. Percentage cell survival was calculated from the mean absorbance in the 4 ADC-treated wells compared to the mean absorbance in the 4 control untreated wells (100%). $IC_{50}$ was determined from the dose-response data using GraphPad Prism using the non-linear curve fit algorithm: sigmoidal dose-response curve with variable slope.

ADC incubation times were 4 days with MDA-MB-468 and 7 days for NCI-N87. MDA-MB-468 and NCI-N87 were cultured in RPMI 1640 with Glutamax+10% (v/v) HyClone™ Fetal Bovine Serum. NCI-N87 is a Her2-expressing cell line and MDA-MB-468 is a Her2 negative cell line.

| $EC_{50}$ (μg/ml) | NCI-N87 | MDA-MB-468 |
|---|---|---|
| ConjA | 0.1176 | >10 |
| ConjA* | 0.01634 | >10 |
| ConjB | 0.01857 | >10 |
| ConjC | 0.1452 | >10 |

Example 15—ADC In Vivo Assay

Methods and Materials

Mice

Female severe combined immunodeficient mice (Fox Chase SCID™, CB17/lcr-Prkdc$^{scid}$/lcolcrCrl, Charles River) were eight weeks old with a body weight (BW) range of 14.5 to 20.0 grams on Day 1 of the study. The animals were fed adlibitum water (reverse osmosis, 1 ppm Cl), and NIH 31 Modified and Irradiated Lab Diet™ consisting of 18.0% crude protein, 5.0% crude fat, and 5.0% crude fiber. The mice were housed on irradiated Enrich-o'cobs™ Laboratory Animal Bedding in static microisolators on a 12-hour light cycle at 20-22° C. and 40-60% humidity. CR Discovery Services specifically complies with the recommendations of the Guide for Care and Use of Laboratory Animals with respect to restraint, husbandry, surgical procedures, feed and fluid regulation, and veterinary care. The animal care and use program at CR Discovery Services is accredited by the Association for Assessment and Accreditation of Laboratory Animal Care International (AAALAC), which assures compliance with accepted standards for the care and use of laboratory animals.

Tumor Cell Culture

Human NCI-N87 gastric carcinoma lymphoma cells were cultured in RPMI-1640 medium supplemented with 10% fetal bovine serum, 2 mM glutamine, 100 units/mL penicillin, 100 µg/mL streptomycin sulfate and 25 µg/mL gentamicin. The cells were grown in tissue culture flasks in a humidified incubator at 37° C., in an atmosphere of 5% $CO_2$ and 95% air.

In Vivo Implantation and Tumor Growth

The NCI-N87 cells used for implantation were harvested during log phase growth and resuspended in phosphate buffered saline (PBS) containing 50% Matrigel™ (BD Biosciences). On the day of tumor implant, each test mouse was injected subcutaneously in the right flank with $1\times10^7$ cells (0.1 mL cell suspension), and tumor growth was monitored as the average size approached the target range of 100 to 150 $mm^3$. Twelve days later, designated as Day 1 of the study, mice were sorted according to calculated tumor size into fourteen groups, seven designated for efficacy evaluation (n=10) and seven designated for sample collection (n=3) each consisting of animals with individual tumor volumes ranging from 108 to 172 $mm^3$ and group mean tumor volumes of 120-124 $mm^3$. Tumors were measured in two dimensions using calipers, and volume was calculated using the formula:

$$\text{Tumor Volume}(mm^3)=(w^2\times l)/2$$

where w=width and l=length, in mm, of the tumor. Tumor weight may be estimated with the assumption that 1 mg is equivalent to 1 $mm^3$ of tumor volume.

Therapeutic Agents

ConjA* was stored protected from light at 4° C. Sterile PBS was used to dose the vehicle control group.

Treatment

On Day 1 of the study, female SCID mice bearing established NCI-N87 xenografts were sorted into groups. An aliquot of stock solution was diluted with PBS to the appropriate concentration. The agent was administered i.v. via tail vein injection once on Day 1. The dosing volume was 0.2 mL per 20 grams of body weight (10 mL/kg), and was scaled to the body weight of each individual animal.

Group 1 mice received PBS vehicle, and served as the control group. Group 2 received ConjA* at 4 mg/kg.

Tumors were measured using calipers twice per week, and each animal was euthanized when its tumor reached the endpoint volume of 800 $mm^3$ or at the end of the study (Day 68), whichever came first. Animals that exited the study for tumor volume endpoint were documented as euthanized for tumor progression (TP), with the date of euthanasia.

Criteria for Regression Responses

Treatment efficacy may be determined from the incidence and magnitude of regression responses observed during the study. Treatment may cause partial regression (PR) or complete regression (CR) of the tumor in an animal. In a PR response, the tumor volume was 50% or less of its Day 1 volume for three consecutive measurements during the course of the study, and equal to or greater than 13.5 $mm^3$ for one or more of these three measurements. In a CR response, the tumor volume was less than 13.5 $mm^3$ for three consecutive measurements during the course of the study. Animals were scored only once during the study for a PR or CR event and only as CR if both PR and CR criteria were satisfied. An animal with a CR response at the termination of a study was additionally classified as a tumor-free survivor (TFS). Animals were monitored for regression responses.

Toxicity

Animals were weighed daily on Days 1-5, then twice per week until the completion of the study. The mice were observed frequently for overt signs of any adverse, treatment-related (TR) side effects, and clinical signs were recorded when observed. Individual body weight was monitored as per protocol, and any animal with weight loss exceeding 30% for one measurement or exceeding 25% for three consecutive measurements was euthanized as a TR death. Group mean body weight loss was also monitored according to CR Discovery Services protocol. Acceptable toxicity was defined as a group mean body weight (BW) loss of less than 20% during the study and no more than 10% TR deaths.

Results

FIG. 1 presents plots of mean tumor growth in which:

| Vehicle | ● |
|---------|---|
| ConjA*  | ♦ |

Group 1 mice received PBS vehicle i.v. qd×1 and served as the control group. The median TTE for Group 1 was 24.8 days. All control tumors attained the 800 $mm^3$ endpoint.

Group 2 received ConjA* at 4 mg/kg i.v. qd×1. CRs were observed in all 10 mice which were additionally classified as TFSs at the termination of the study.

In the treatment group the body weight nadir was −9.5% on day 50 of the study. No TR deaths were observed.

STATEMENTS OF INVENTION

1. A compound with the formula I:

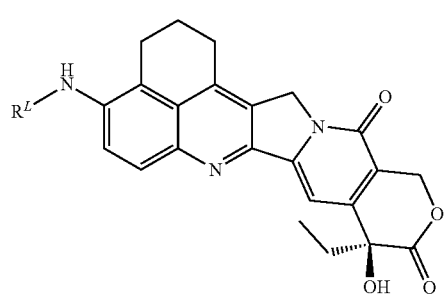

and salts and solvates thereof, wherein $R^L$ is a linker for connection to a Ligand Unit, which is selected from:

(ia):

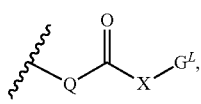

wherein
Q is:

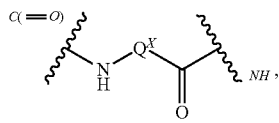

where $Q^X$ is such that Q is an amino-acid residue, a dipeptide residue, a tripeptide residue or a tetrapeptide residue;
X is:

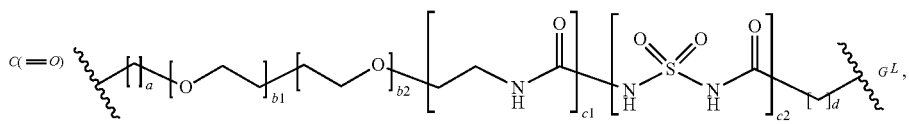

where a=0 to 5, b1=0 to 16, b2=0 to 16, c1=0 or 1, c2=0 or 1, d=0 to 5, wherein at least b1 or b2=0 and at least c1 or c2=0;
$G^L$ is a linker for connecting to a Ligand Unit;
(ib):

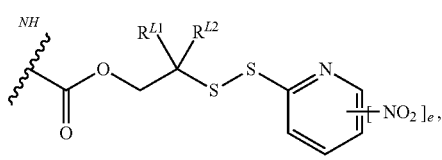

where $R^{L1}$ and $R^{L2}$ are independently selected from an methyl, or together with the carbon atom to which they are bound form a cyclopropylene or cyclobutylene group; and
e is 0 or 1.

2. The compound according to statement 1, wherein $R^L$ is of formula Ia.

3. The compound according to statement 2, wherein Q is an amino acid residue.

4. The compound according to statement 3, wherein Q is selected from: Phe, Lys, Val, Ala, Cit, Leu, Ile, Arg, and Trp.

5. The compound according to statement 2, wherein Q is a dipeptide residue.

6. The compound according to statement 5, wherein Q is selected from:
$^{NH}$-Phe-Lys-$^{C=O}$,
$^{NH}$-Val-Ala-$^{C=O}$
$^{NH}$-Val-Lys-$^{C=O}$
$^{NH}$-Ala-Lys-$^{C=O}$
$^{NH}$-Val-Cit-$^{C=O}$
$^{NH}$-Phe-Cit-$^{C=O}$
$^{NH}$-Leu-Cit-$^{C=O}$
$^{NH}$-Ile-Cit-$^{C=O}$
$^{NH}$-Phe-Arg-$^{C=O}$
$^{NH}$-Trp-Cit-$^{C=O}$, and
$^{NH}$-Gly-Val-$^{C=O}$ 7. The compound according to statement 6, wherein Q is selected from $^{NH}$-Phe-Lys-$^{C=O}$, $^{NH}$-Val-Cit-$^{C=O}$ and $^{NH}$-Val-Ala-$^{C=O}$.

8. The compound according to statement 2, wherein Q is a tripeptide residue.

9. The compound according to statement 8, wherein Q is selected from:
$^{NH}$-Glu-Val-Ala-$^{C=O}$
$^{NH}$-Glu-Val-Cit-$^{C=O}$
$^{NH}$-αGlu-Val-Ala-$^{C=O}$, and
$^{NH}$-αGlu-Val-Cit-$^{C=O}$ 10. The compound according to statement 2, wherein Q is a tetrapeptide residue.

11. The compound according to statement 10, wherein Q is selected from:
$^{NH}$-Gly-Gly-Phe-Gly$^{C=O}$; and
$^{NH}$-Gly-Phe-Gly-Gly $^{C=O}$.

12. The compound according to statement 11, wherein Q is:
$^{NH}$-Gly-Gly-Phe-Gly$^{C=O}$.

13. The compound according to any one of statements 2 to 12, wherein a is 0 to 3.

14. The compound according to statement 13, wherein a is 0 or 1.

15. The compound according to statement 13, wherein a is 0.

16. The compound according to any one of statements 2 to 15, wherein b1 is 0 to 8.

17. The compound according to statement 16, wherein b1 is 0.

18. The compound according to statement 16, wherein b1 is 2.

19. The compound according to statement 16, wherein b1 is 3.

20. The compound according to statement 16, wherein b1 is 4.

21. The compound according to statement 16, wherein b1 is 5.

22. The compound according to statement 16, wherein b1 is 8.

23. The compound according to any one of statements 2 to 15 and 17, wherein b2 is 0 to 8.

24. The compound according to statement 23, wherein b2 is 0.

25. The compound according to statement 23, wherein b2 is 2.

26. The compound according to statement 23, wherein b2 is 3.

27. The compound according to statement 23, wherein b2 is 4.

28. The compound according to statement 23, wherein b2 is 5.

29. The compound according to statement 23, wherein b2 is 8.
30. The compound according to any one of statements 2 to 29, wherein c1 is 0.
31. The compound according to any one of statements 2 to 29, wherein c1 is 1.
32. The compound according to any one of statements 2 to 31, wherein c2 is 0.
33. The compound according to any one of statements 2 to 30, wherein c2 is 1.
34. The compound according to any one of statements 2 to 33, wherein d is 0 to 3.
35. The compound according to statement 34, wherein d is 1 or 2.
36. The compound according to statement 34, wherein d is 2.
37. The compound according to any one of statements 2 to 33, wherein d is 5.
38. The compound according to any one of statements 2 to 12, wherein a is 0, b1 is 0, c1 is 1, c2 is 0 and d is 2, and b2 is from 0 to 8.
39. The compound according to statement 38, wherein b2 is 0, 2, 3, 4, 5 or 8.
40. The compound according to any one of statements 2 to 12, wherein a is 1, b2 is 0, c1 is 0, c2 is 0 and d is 0, and b1 is from 0 to 8.
41. The compound according to statement 40, wherein b1 is 0, 2, 3, 4, 5 or 8.
42. The compound according to any one of statements 2 to 12, wherein a is 0, b1 is 0, c1 is 0, c2 is 0 and d is 1, and b2 is from 0 to 8.
43. The compound according to statement 42, wherein b2 is 0, 2, 3, 4, 5 or 8.
44. The compound according to any one of statements 2 to 12, wherein b1 is 0, b2 is 0, c1 is 0, c2 is 0, one of a and d is 0, and the other of a and d is from 1 to 5.
45. The compound according to statement 44, wherein the other of a and d is 1 or 5.
46. The compound according to any one of statements 2 to 12, wherein a is 1, b2 is 0, c1 is 0, c2 is 1, d is 2, and b1 is from 0 to 8.
47. The compound according to statement 46, wherein b1 is 0, 2, 3, 4, 5 or 8.
48. The compound according to any one of statements 2 to 47, wherein $G^L$ is selected from

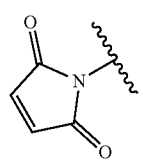
($G^{L1-1}$)

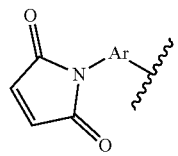
($G^{L1-2}$)

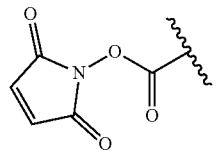
($G^{L2}$)

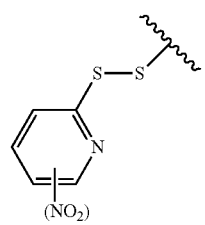
($G^{L3-1}$)

where the $NO_2$ group is optional

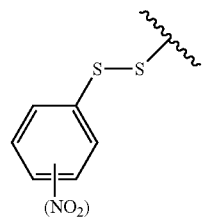
($G^{L3-2}$)

where the $NO_2$ group is optional

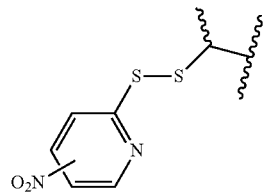
($G^{L3-3}$)

where the $NO_2$ group is optional

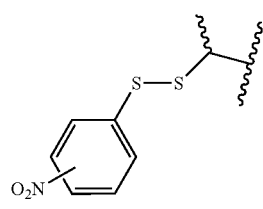
($G^{L3-4}$)

where the $NO_2$ group is optional

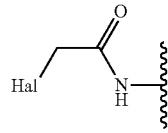
($G^{L4}$)

Where Hal = I, Br, Cl

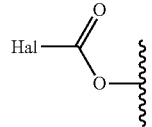
($G^{L5}$)

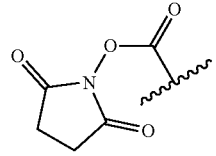
($G^{L6}$)

-continued (G$^{L7}$) 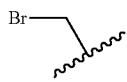

(G$^{L8}$) 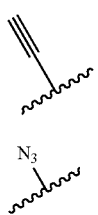

(G$^{L9}$) 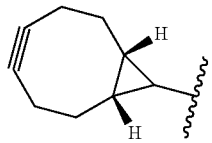

(G$^{L10}$) 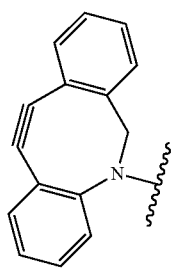

(G$^{L11}$) 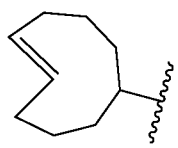

(G$^{L12}$) 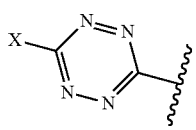

(G$^{L13}$) 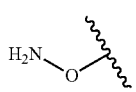

(G$^{L14}$)

where Ar represents a C$_{5-6}$ arylene group, and X represents C$_{1-4}$ alkyl.

49. A compound according to statement 48, wherein G$^L$ is selected from G$^{L1-1}$ and G$^{L1-2}$.

50. A compound according to statement 48, wherein G$^L$ is G$^{L1-1}$.

51. The compound according to statement 1, wherein R$^L$ is of formula Ib.

52. The compound according to statement 51, wherein both R$^{L1}$ and R$^{L2}$ are H.

53. The compound according to statement 51, wherein R$^{L1}$ is H and R$^{L2}$ is methyl.

54. The compound according to statement 51, wherein both R$^{L1}$ and R$^{L2}$ are methyl.

55. The compound according to statement 51, wherein R$^{L1}$ and R$^{L2}$ together with the carbon atom to which they are bound form a cyclopropylene group.

56. The compound according to statement 51, wherein R$^{L1}$ and R$^{L2}$ together with the carbon atom to which they are bound form a cyclobutylene group.

57. The compound according to any one of statements 51 to 56, wherein e is 0.

58. The compound according to any one of statements 51 to 56, wherein e is 1.

59. A conjugate of formula IV:

$$L-(D^L)_p \quad \quad (IV)$$

or a pharmaceutically acceptable salt or solvate thereof, wherein L is a Ligand unit (i.e., a targeting agent), D$^L$ is a Drug Linker unit that is of formula III:

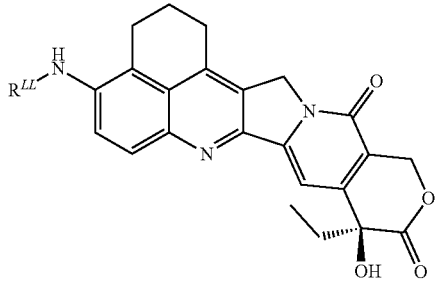

III

R$^{LL}$ is a linker connected to the Ligand unit selected from (ia'):

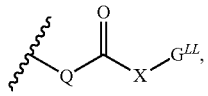

Ia' where Q and X are as defined in any one of statements 1 to 47 and G$^{LL}$ is a linker connected to a Ligand Unit; and

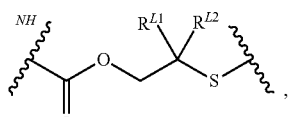

Ib' where R$^{L1}$ and R$^{L2}$ are as defined in any one of statements 1 and 52 to 56; and p is an integer of from 1 to 20.

60. The conjugate according to statement 59, wherein G$^{LL}$ is selected from:

(G$^{LL1-1}$) 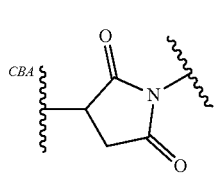

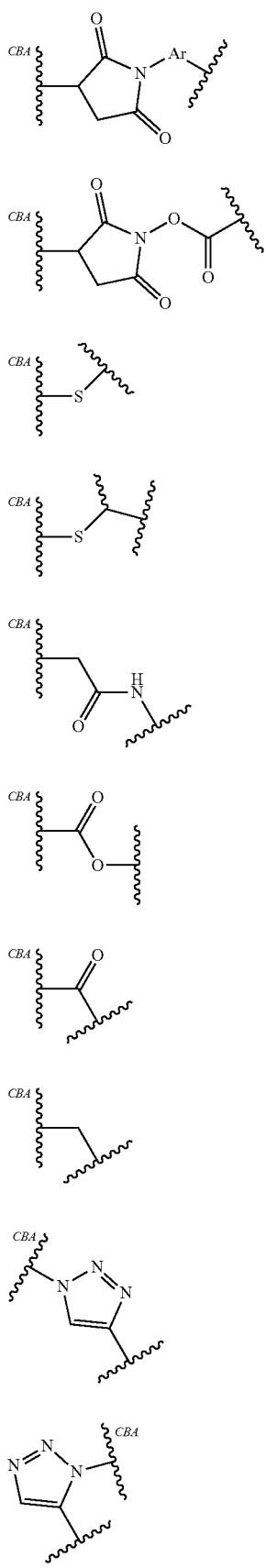
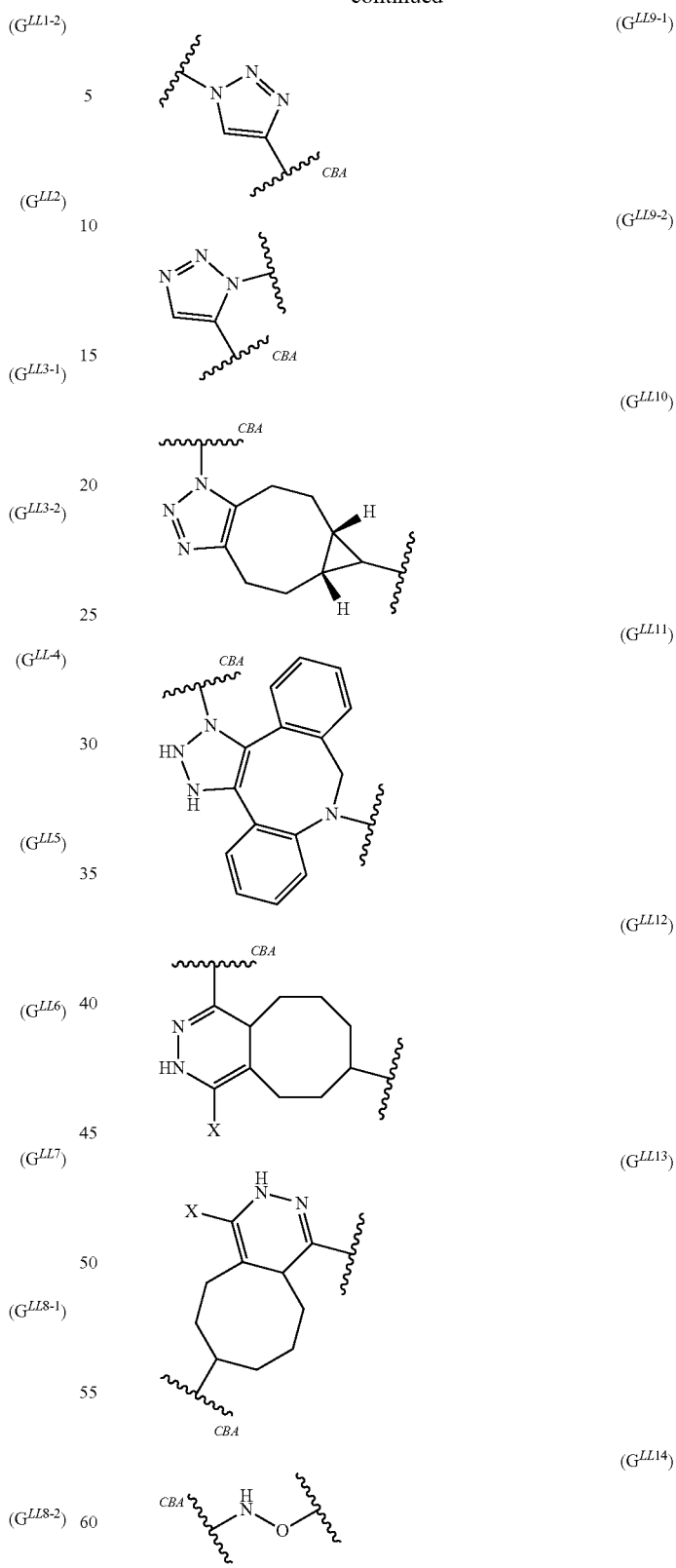
where Ar represents arylene group and X represents $C_{1-4}$ alkyl.
61. The conjugate according to statement 60, wherein $G^{LL}$ is selected from $G^{LL1-1}$ and $G^{LL1-2}$.

62. The conjugate according to statement 61, wherein $G^{LL}$ is $G^{LL-1}$.

63. The conjugate according to any one of statements 59 to 62, wherein the Ligand Unit is a Cell Binding Agent.

64. The conjugate according to any one of statements 59 to 62, wherein the Ligand Unit is an antibody or an active fragment thereof.

65. The conjugate according to statement 64, wherein the antibody or antibody fragment is an antibody or antibody fragment for a tumour-associated antigen.

66. The conjugate according to statement 65, wherein the antibody or antibody fragment is an antibody which binds to one or more tumor-associated antigens or cell-surface receptors selected from (1)-(89):

(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA-FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30—TNFRSF8;
(51) BCMA-TNFRSF17;
(52) CT Ags-CTA;
(53) CD174 (Lewis Y)-FUT3;
(54) CLEC14A;
(55) GRP78—HSPA5;
(56) CD70;
(57) Stem Cell specific antigens;
(58) ASG-5;
(59) ENPP3;
(60) PRR4;
(61) GCC-GUCY2C;
(62) Liv-1—SLC39A6;
(63) 5T4;
(64) CD56—NCMA1;
(65) CanAg;
(66) FOLR1;
(67) GPNMB;
(68) TIM-1—HAVCR1;
(69) RG-1/Prostate tumor target Mindin-Mindin/RG-1;
(70) B7-H4-VTCN1;
(71) PTK7;
(72) CD37;
(73) CD138-SDC1;
(74) CD74;
(75) Claudins-CLs;
(76) EGFR;
(77) Her3;
(78) RON-MST1R;
(79) EPHA2;
(80) CD20-MS4A1;
(81) Tenascin C-TNC;
(82) FAP;
(83) DKK-1;
(84) CD52;
(85) CS1-SLAMF7;
(86) Endoglin-ENG;
(87) Annexin A1-ANXA1;
(88) V-CAM (CD106)-VCAM1;
(89) ASCT2 (SLC1A5).

67. The conjugate according to any one of statements 64 to 66, wherein the antibody or antibody fragment is a cysteine-engineered antibody.

684. The conjugate according to any one of statements 64 to 67, wherein the drug loading (p) of drugs (D) to antibody (Ab) is an integer from 1 to about 10.

69. The conjugate according to statement 68, wherein p is 1, 2, 3, 4, 5, 6, 7, 8, 9 or 10.

70. A mixture of conjugates according to any one of statements 64 to 69, wherein the average drug loading per antibody in the mixture of antibody-drug conjugates is about 1 to about 10.

71. The conjugate or mixture according to any one of statements 59 to 70, for use in therapy.

72. A pharmaceutical composition comprising the conjugate or mixture of any one of statements 59 to 70 and a pharmaceutically acceptable diluent, carrier or excipient.

73. The conjugate or mixture according to any one of statements 59 to 70, or the pharmaceutical composition according to statement 72, for use in the treatment of a proliferative disease in a subject.

74. The conjugate, mixture or pharmaceutical composition according to statement 73, wherein the disease is cancer.

75. Use of a conjugate or mixture according to any one of statements 59 to 70, or the pharmaceutical composition according to statement 72 in a method of medical treatment.

76. A method of medical treatment comprising administering to a patient the pharmaceutical composition of statement 72.

77. The method of statement 76 wherein the method of medical treatment is for treating cancer.

78. The method of statement 77, wherein the patient is administered a chemotherapeutic agent, in combination with the conjugate.

79. Use of a conjugate or mixture according to any one of statements 59 to 70 in a method of manufacture of a medicament for the treatment of a proliferative disease.

80. A method of treating a mammal having a proliferative disease, comprising administering an effective amount of conjugate or mixture according to any one of statements 59 to 70, or the pharmaceutical composition according to statement 72.

81. The compound A:

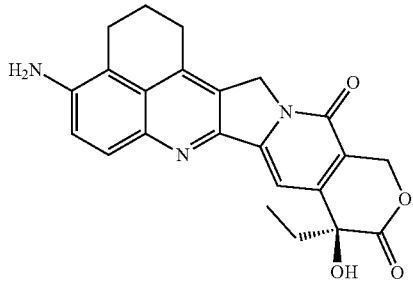

A as a single enantiomer or in an enantiomerically enriched form.

82. A compound with the formula VI:

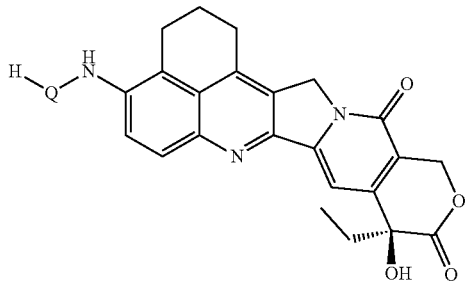

VI where Q is as in any one of statements 1 and 3 and 12.

Statements of Invention from 1st Priority Application (P1)

P1-1. A compound with the formula I:

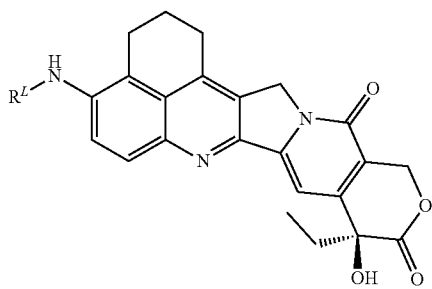

I and salts and solvates thereof, wherein $R^L$ is a linker for connection to a cell binding agent, which is selected from:

(ia):

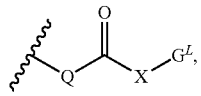

Ia wherein

Q is:

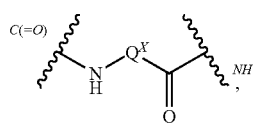

where $Q^X$ is such that Q is an amino-acid residue, a dipeptide residue or a tripeptide residue;

X is:

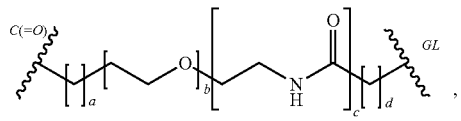

where a=0 to 5, b=0 to 16, c=0 or 1, d=0 to 5;

$G^L$ is a linker for connecting to a Ligand Unit;

(ib):

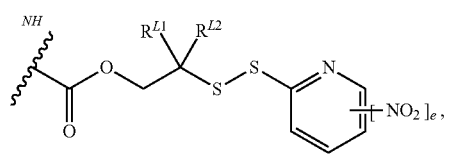

Ib where $R^L1$ and $R^{L2}$ are independently selected from H and methyl, or together with the carbon atom to which they are bound form a cyclopropylene or cyclobutylene group; and e is 0 or 1.

P1-2. The compound according to statement P1-1, wherein $R^L$ is of formula Ia.

P1-3. The compound according to statement P1-2, wherein Q is an amino acid residue.

P1-4. The compound according to statement P1-3, wherein Q is selected from: Phe, Lys, Val, Ala, Cit, Leu, Ile, Arg, and Trp.

P1-5. The compound according to statement P1-2, wherein Q is a dipeptide residue.

P1-6. The compound according to statement P1-5, wherein Q is selected from:

$^{NH}$-Phe-Lys-$^{C=O}$
$^{NH}$-Val-Ala-$^{C=O}$
$^{NH}$-Val-Lys-$^{C=O}$
$^{NH}$-Ala-Lys-$^{C=O}$
$^{NH}$-Val-Cit-$^{C=O}$
$^{NH}$-Phe-Cit-$^{C=O}$
$^{NH}$-Leu-Cit-$^{C=O}$ $^{NH}$-Ile-Cit-$^{C=O}$ $^{NH}$-Phe-Arg-$^{C=O}$ $^{NH}$-Trp-Cit-$^{C=O}$, and $^{NH}$-Gly-Val-$^{C=O}$ P1-7. The conjugate according to statement P1-6, wherein Q is selected from $^{NH}$-Phe-Lys-$^{C=O}$, $^{NH}$-Val-Cit-$^{C=O}$ and $^{NH}$-Val-Ala-$^{C=O}$.

P1-8. The compound according to statement P1-2, wherein Q is a tripeptide residue.

P1-9. The compound according to any one of statements P1-2 to P1-8, wherein a is 0 to 3.

P1-10. The compound according to statement P1-9, wherein a is 0 or 1.

P1-11. The compound according to statement P1-9, wherein a is 0.

P1-12. The compound according to any one of statements P1-2 to P1-11, wherein b is 0 to 8.

P1-13. The compound according to statement P1-12, wherein b is 0.

P1-14. The compound according to statement P1-12, wherein b is 4.

P1-15. The compound according to statement P1-12, wherein b is 8.

P1-16. The compound according to any one of statements P1-2 to P1-15, wherein c is 0.

P1-17. The compound according to any one of statements P1-2 to P1-15, wherein c is 1.

P1-18. The compound according to any one of statements P1-2 to P1-17, wherein d is 0 to 3.

P1-19. The compound according to statement P1-18, wherein d is 1 or 2.

P1-20. The compound according to statement P1-19, wherein d is 2.

P1-21. The compound according to any one of statements P1-2 to P1-8, wherein a is 0, c is 1 and d is 2, and b is 0, 4 or 8.

P1-22. The compound according to any one of statements P1-2 to P1-21, wherein $G^L$ is selected from

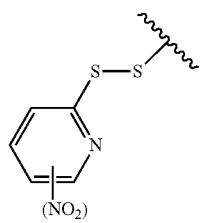
(G$^{L1\text{-}1}$)

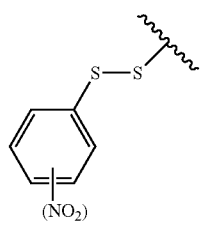
(G$^{L1\text{-}2}$)

(G$^{L2}$)

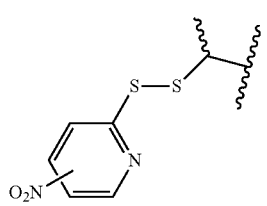
(G$^{L3\text{-}1}$)

where the NO$_2$ group is optional

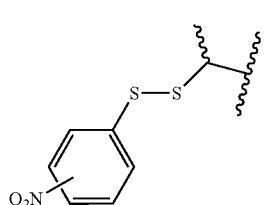
(G$^{L3\text{-}2}$)

where the NO$_2$ group is optional (G$^{L3\text{-}3}$)

where the NO$_2$ group is optional (G$^{L3\text{-}4}$)

where the NO$_2$ group is optional

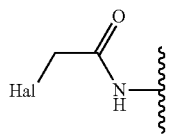
(G$^{L4}$)

Where Hal = I, Br, Cl

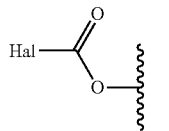
(G$^{L5}$)

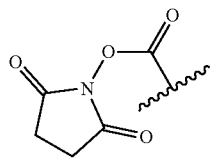
(G$^{L6}$)

-continued

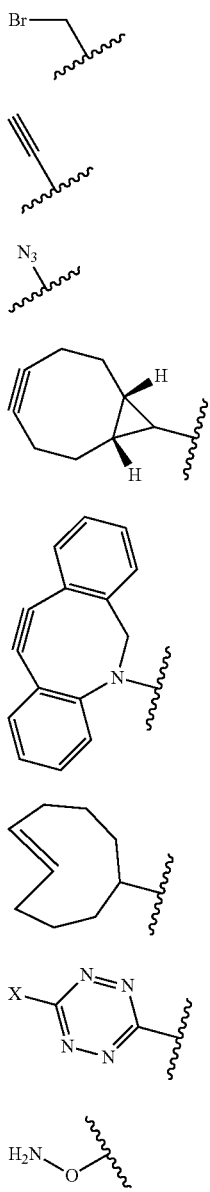

(G$^{L7}$)

(G$^{L8}$)

(G$^{L9}$)

(G$^{L10}$)

(G$^{L11}$)

(G$^{L12}$)

(G$^{L13}$)

(G$^{L14}$)

where Ar represents a C$_{5-6}$ arylene group, and X represents C$_{1-4}$ alkyl.

P1-23. A compound according to statement P1-22, wherein G$^L$ is selected from G$^{L1-1}$ and G$^{L1-2}$.

P1-24. A compound according to statement P1-22, wherein G$^L$ is G$^{L1-1}$.

P1-25. The compound according to statement P1-1, wherein R$^L$ is of formula Ib.

P1-26. The compound according to statement P1-25, wherein both R$^{L1}$ and R$^{L2}$ are H.

P1-27. The compound according to statement P1-25, wherein R$^{L1}$ is H and R$^{L2}$ is methyl.

P1-28. The compound according to statement P1-25, wherein both R$^{L1}$ and R$^{L2}$ are methyl.

P1-29. The compound according to statement P1-25, wherein R$^{L1}$ and R$^{L2}$ together with the carbon atom to which they are bound form a cyclopropylene group.

P1-30. The compound according to statement P1-25, wherein R$^{L1}$ and R$^{L2}$ together with the carbon atom to which they are bound form a cyclobutylene group.

P1-31. The compound according to any one of statements P1-25 to P1-30, wherein e is 0.

P1-32. The compound according to any one of statements P1-25 to P1-30, wherein e is 1.

P1-33. A conjugate of formula IV:

$$L\text{-}(D^L)_p \qquad (IV)$$

or a pharmaceutically acceptable salt or solvate thereof, wherein L is a Ligand unit (i.e., a targeting agent), D$^L$ is a Drug Linker unit that is of formula III:

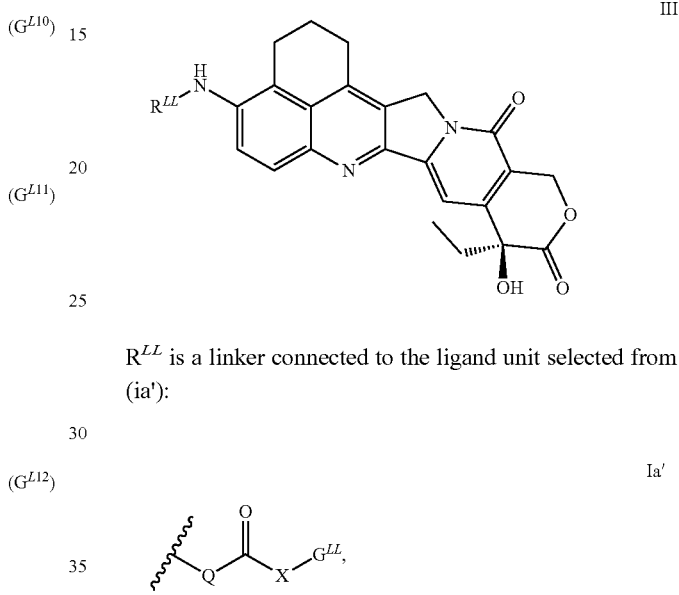

III

R$^{LL}$ is a linker connected to the ligand unit selected from (ia'):

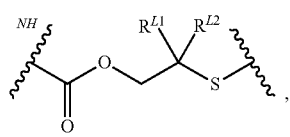

Ia' where Q and X are as defined in any one of statements P1-1 to P1-21 and G$^{LL}$ is a linker connected to a Ligand Unit; and (ib'):

Ib' where R$^{L1}$ and R$^{L2}$ are as defined in any one of statements P1-1 and P1-25 to P1-30; and p is an integer of from 1 to 20.

P1-34. The conjugate according to statement P1-33, wherein G$^{LL}$ is selected from:

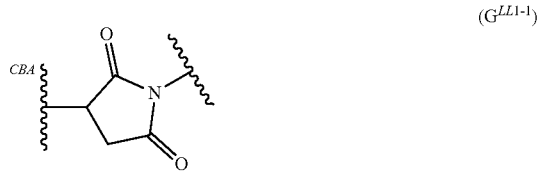

(G$^{LL1-1}$)

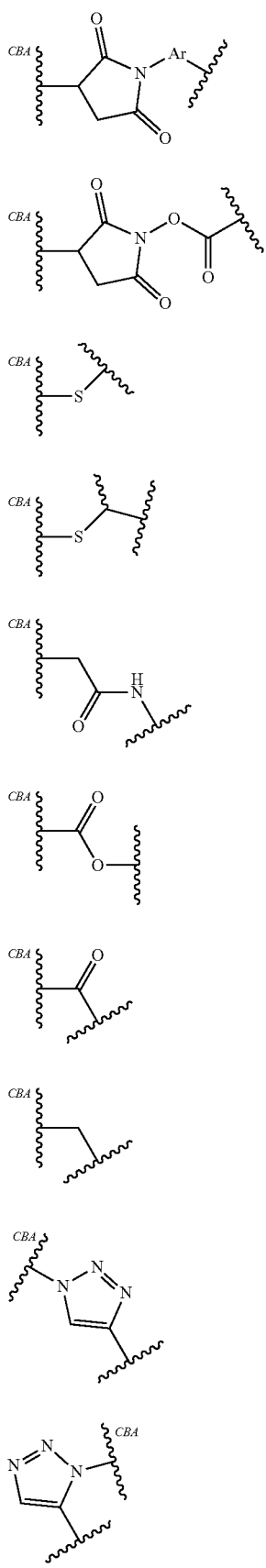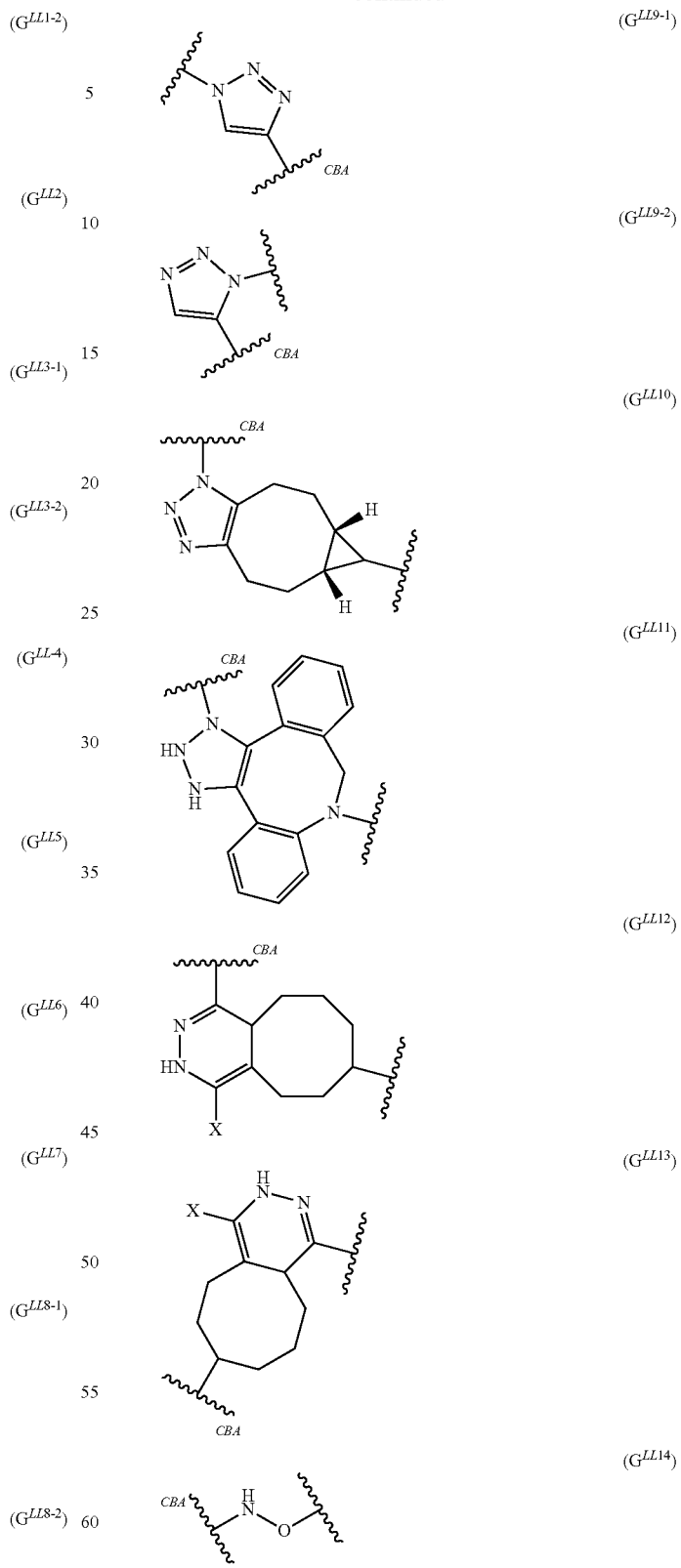
where Ar represents a $C_{5-6}$ arylene group and X represents $C_{1-4}$ alkyl.
P1-35. The conjugate according to statement P1-34, wherein $G^{LL}$ is selected from $G^{LL1-1}$ and $G^{LL1-2}$.

P1-36. The conjugate according to statement P1-35, wherein $G^{LL}$ is $G^{LL1-1}$.

P1-37. The conjugate according to any one of statements P1-33 to P1-36, wherein the cell binding agent is an antibody or an active fragment thereof.

P1-38. The conjugate according to statement P1-37, wherein the antibody or antibody fragment is an antibody or antibody fragment for a tumour-associated antigen.

P1-39. The conjugate according to statement P1-38, wherein the antibody or antibody fragment is an antibody which binds to one or more tumor-associated antigens or cell-surface receptors selected from (1)-(88):

(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA-FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30-TNFRSF8;
(51) BCMA-TNFRSF17;
(52) CT Ags-CTA;
(53) CD174 (Lewis Y)-FUT3;
(54) CLEC14A;
(55) GRP78-HSPA5;
(56) CD70;
(57) Stem Cell specific antigens;
(58) ASG-5;
(59) ENPP3;
(60) PRR4;
(61) GCC-GUCY2C;
(62) Liv-1-SLC39A6;
(63) 5T4;
(64) CD56-NCMA1;
(65) CanAg;
(66) FOLR1;
(67) GPNMB;
(68) TIM-1-HAVCR1;
(69) RG-1/Prostate tumor target Mindin-Mindin/RG-1;
(70) B7-H4-VTCN1;
(71) PTK7;
(72) CD37;
(73) CD138-SDC1;
(74) CD74;
(75) Claudins—CLs;
(76) EGFR;
(77) Her3;
(78) RON-MST1R;
(79) EPHA2;
(80) CD20-MS4A1;
(81) Tenascin C-TNC;
(82) FAP;
(83) DKK-1;
(84) CD52;
(85) CS1-SLAMF7;
(86) Endoglin—ENG;
(87) Annexin A1—ANXA1;
(88) V-CAM (CD106)—VCAM1;
(89) ASCT2 (SLC1A5).

P1-40. The conjugate according to any one of statements P1-37 to P1-39, wherein the antibody or antibody fragment is a cysteine-engineered antibody.

P1-41. The conjugate according to any one of statements P1-37 to P1-40, wherein the drug loading (p) of drugs (D) to antibody (Ab) is an integer from 1 to about 10.

P1-42. The conjugate according to statement P1-41, wherein p is 1, 2, 3, 4, 5, 6, 7, 8, 9 or 10.

P1-43. A mixture of conjugates according to any one of statements P1-33 to P1-42, wherein the average drug loading per antibody in the mixture of antibody-drug conjugate compounds is about 1 to about 10.

P1-44. The conjugate or mixture according to any one of statements P1-33 to P1-43, for use in therapy.

P1-45. A pharmaceutical composition comprising the conjugate or mixture of any one of statements P1-33 to P1-43 and a pharmaceutically acceptable diluent, carrier or excipient.

P1-46. The conjugate or mixture according to any one of statements P1-33 to P1-43, or the pharmaceutical composition according to statement P1-45, for use in the treatment of a proliferative disease in a subject.

P1-47. The conjugate or mixture according to statement P1-46, wherein the disease is cancer.

P1-48. Use of a conjugate or mixture according to any one of statements P1-33 to P1-43, or the pharmaceutical composition according to statement P1-45 in a method of medical treatment.

P1-49. A method of medical treatment comprising administering to a patient the pharmaceutical composition of statement P1-45.

P1-50. The method of statement P1-49 wherein the method of medical treatment is for treating cancer.

P1-51. The method of statement P1-50, wherein the patient is administered a chemotherapeutic agent, in combination with the conjugate.

P1-52. Use of a conjugate or mixture according to any one of statements P1-33 to P1-43 in a method of manufacture of a medicament for the treatment of a proliferative disease.

P1-53. A method of treating a mammal having a proliferative disease, comprising administering an effective amount of conjugate or mixture according to any one of statements P1-33 to P1-43, or the pharmaceutical composition according to statement P1-45.

P1-54. The compound A:

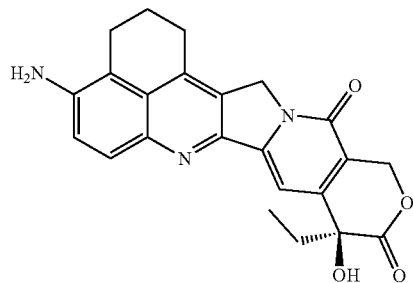

as a single enantiomer or in an enantiomerically enriched form.

Statements of Invention from $2^{nd}$ Priority Application (P2)

P2-1. A compound with the formula I:

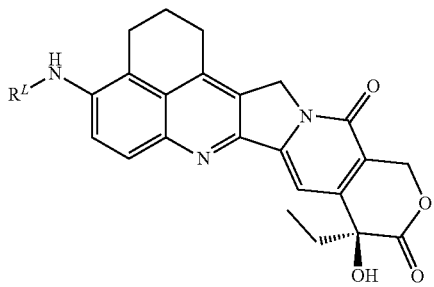

and salts and solvates thereof, wherein $R^L$ is a linker for connection to a cell binding agent, which is selected from:

(ia):

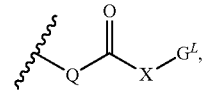

wherein

Q is:

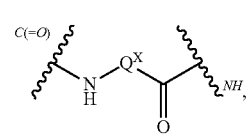

where $Q^X$ is such that Q is an amino-acid residue, a dipeptide residue, a tripeptide residue or a tetrapeptide residue;

X is:

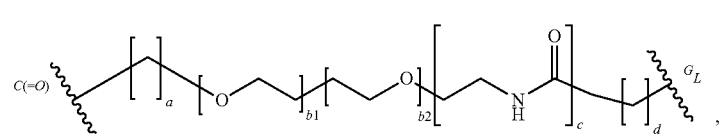

where a=0 to 5, b1=0 to 16, b2=0 to 16, c=0 or 1, d=0 to 5, wherein at least b1 or b2=0;

$G^L$ is a linker for connecting to a Ligand Unit;

(ib):

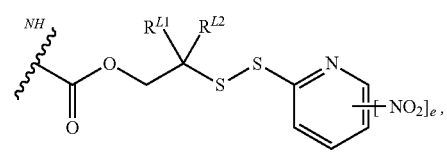

where $R^{L1}$ and $R^{L2}$ are independently selected from H and methyl, or together with the carbon atom to which they are bound form a cyclopropylene or cyclobutylene group; and e is 0 or 1.

P2-2. The compound according to statement P2-1, wherein $R^L$ is of formula Ia.

P2-3. The compound according to statement P2-2, wherein Q is an amino acid residue.

P2-4. The compound according to statement P2-3, wherein Q is selected from: Phe, Lys, Val, Ala, Cit, Leu, Ile, Arg, and Trp.

P2-5. The compound according to statement P2-2, wherein Q is a dipeptide residue.

P2-6. The compound according to statement P2-5, wherein Q is selected from:

$^{NH}$-Phe-Lys-$^{C=O}$
$^{NH}$-Val-Ala-$^{C=O}$
$^{NH}$-Val-Lys-$^{C=O}$
$^{NH}$-Ala-Lys-$^{C=O}$
$^{NH}$-Val-Cit-$^{C=O}$
$^{NH}$-Phe-Cit-$^{C=O}$
$^{NH}$-Leu-Cit-$^{C=O}$
$^{NH}$-Ile-Cit-$^{C=O}$
$^{NH}$-Phe-Arg-$^{C=O}$
$^{NH}$-Trp-Cit-$^{C=O}$, and
$^{NH}$-Gly-Val-$^{C=O}$ P2-7. The compound according to statement P2-6, wherein Q is selected from $^{NH}$-Phe-Lys-$^{C=O}$, $^{NH}$-Val-Cit-$^{C=O}$ and $^{NH}$-Val-Ala-$^{C=O}$ P2-8. The compound according to statement P2-2, wherein Q is a tripeptide residue.

P2-9. The compound according to statement P2-8, wherein Q is selected from:

$^{NH}$-Glu-Val-Ala-$^{C=O}$
$^{NH}$-Glu-Val-Cit-$^{C=O}$
$^{NH}$-αGlu-Val-Ala-$^{C=O}$, and
$^{NH}$-αGlu-Val-Cit-$^{C=O}$ P2-10. The compound according to statement P2-2, wherein Q is a tetrapeptide residue.

P2-11. The compound according to statement P2-10, wherein Q is selected from:

$^{NH}$-Gly-Gly-Phe-Gly$^{C=O}$; and
$^{NH}$-Gly-Phe-Gly-Gly$^{C=O}$.

P2-12. The compound according to statement P2-11, wherein Q is:

$^{NH}$-Gly-Gly-Phe-Gly$^{C=O}$. P2-13. The compound according to any one of statements P2-2 to P2-12, wherein a is 0 to 3.

P2-14. The compound according to statement P2-13, wherein a is 0 or 1.

P2-15. The compound according to statement P2-13, wherein a is 0.

P2-16. The compound according to any one of statements P2-2 to P2-15, wherein b1 is 0 to 8.

P2-17. The compound according to statement P2-16, wherein b1 is 0.

P2-18. The compound according to statement P2-16, wherein b1 is 2.

P2-19. The compound according to statement P2-16, wherein b1 is 3.

P2-20. The compound according to statement P2-16, wherein b1 is 4.

P2-21. The compound according to statement P2-16, wherein b1 is 5.

P2-22. The compound according to statement P2-16, wherein b1 is 8.

P2-23. The compound according to any one of statements P2-2 to P2-15 and P2-17, wherein b2 is 0 to 8.

P2-24. The compound according to statement P2-23, wherein b2 is 0.

P2-25. The compound according to statement P2-23, wherein b2 is 2.

P2-26. The compound according to statement P2-23, wherein b2 is 3.

P2-27. The compound according to statement P2-23, wherein b2 is 4.

P2-28. The compound according to statement P2-23, wherein b2 is 5.

P2-29. The compound according to statement P2-23, wherein b2 is 8.

P2-30. The compound according to any one of statements P2-2 to P2-29, wherein c is 0.

P2-31. The compound according to any one of statements P2-2 to P2-29, wherein c is 1.

P2-32. The compound according to any one of statements P2-2 to P2-31, wherein d is 0 to 3.

P2-33. The compound according to statement P2-32, wherein d is 1 or 2.

P2-34. The compound according to statement P2-32, wherein d is 2.

P2-35. The compound according to any one of statements P2-2 to P2-12, wherein a is 0, b1 is 0, c is 1 and d is 2, and b2 is from 0 to 8.

P2-36. The compound according to statement P2-35, wherein b2 is 0, 2, 3, 4, 5 or 8.

P2-37. The compound according to any one of statements P2-2 to P2-12, wherein a is 1, b2 is 0, c is 0 and d is 0, and b1 is from 0 to 8.

P2-38. The compound according to statement P2-37, wherein b1 is 0, 2, 3, 4, 5 or 8.

P2-39. The compound according to any one of statements P2-2 to P2-12, wherein a is 0, b1 is 0, c is 0 and d is 1, and b2 is from 0 to 8.

P2-40. The compound according to statement P2-39, wherein b2 is 0, 2, 3, 4, 5 or 8.

P2-41. The compound according to any one of statements P2-2 to P2-12, wherein b1 is 0, b2 is 0, c is 0, one of a and d is 0, and the other of a and d is from 1 to 5.

P2-42. The compound according to statement P2-41, wherein the other of a and d is 1 or 5.

P2-43. The compound according to any one of statements P2-2 to P2-42, wherein $G^L$ is selected from

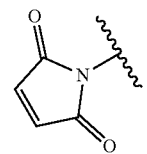 (G$^{L1\text{-}1}$)

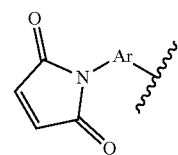 (G$^{L1\text{-}2}$)

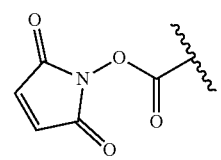 (G$^{L2}$)

(G^{L3-1})

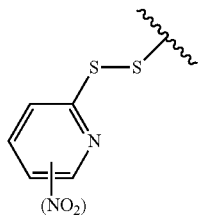

where the NO₂ group is optional (G^{L3-2})

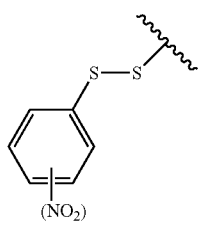

where the NO₂ group is optional (G^{L3-3})

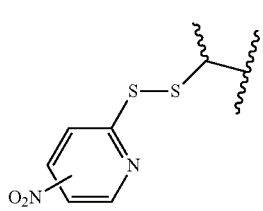

where the NO₂ group is optional (G^{L3-4})

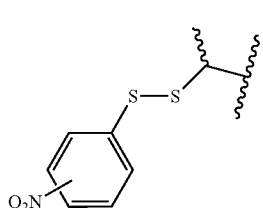

where the NO₂ group is optional (G^{L4})

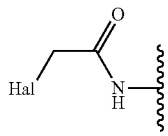

Where Hal = I, Br, Cl (G^{L5})

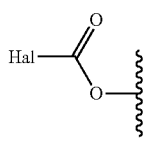

(G^{L6})

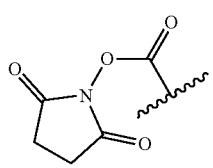

(G^{L7})

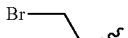

(G^{L8})

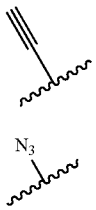

(G^{L9})

N₃

(G^{L10})

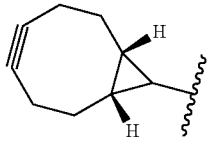

(G^{L11})

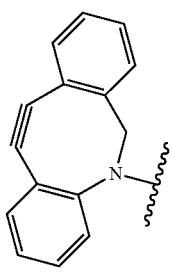

(G^{L12})

(G^{L13})

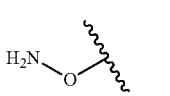

(G^{L14})

H₂N—O— where Ar represents a $C_{5-6}$ arylene group, and X represents $C_{1-4}$ alkyl.

P2-44. A compound according to statement P2-43, wherein $G^L$ is selected from $G^{L1-1}$ and $G^{L1-2}$.

P2-45. A compound according to statement P2-43, wherein $G^L$ is $G^{L1-1}$.

P2-46. The compound according to statement P2-1, wherein $R^L$ is of formula Ib.

P2-47. The compound according to statement P2-46, wherein both $R^{L1}$ and $R^{L2}$ are H.

P2-48. The compound according to statement P2-46, wherein $R^{L1}$ is H and $R^{L2}$ is methyl.

P2-49. The compound according to statement P2-46, wherein both $R^{L1}$ and $R^{L2}$ are methyl.

P2-50. The compound according to statement P2-46, wherein $R^{L1}$ and $R^{L2}$ together with the carbon atom to which they are bound form a cyclopropylene group.

P2-51. The compound according to statement P2-46, wherein $R^{L1}$ and $R^{L2}$ together with the carbon atom to which they are bound form a cyclobutylene group.

P2-52. The compound according to any one of statements P2-46 to P2-51, wherein e is 0.

P2-53. The compound according to any one of statements P2-46 to P2-51, wherein e is 1.

P2-54. A conjugate of formula IV:

L-(D$^L$)$_p$ (IV)

or a pharmaceutically acceptable salt or solvate thereof, wherein L is a Ligand unit (i.e., a targeting agent), D$^L$ is a Drug Linker unit that is of formula III:

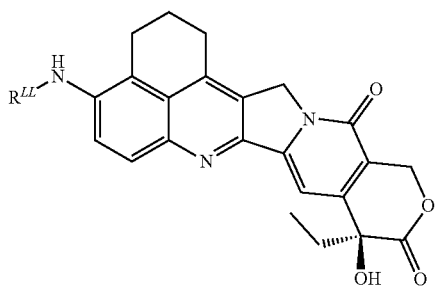

III

R$^{LL}$ is a linker connected to the Ligand unit selected from (ia'):

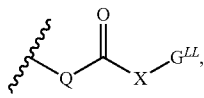

Ia' where Q and X are as defined in any one of statements P2-1 to P2-42 and G$^{LL}$ is a linker connected to a Ligand Unit; and (ib'):

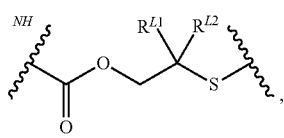

Ib' where R$^{L1}$ and R$^{L2}$ are as defined in any one of statements P2-1 and P2-47 to P2-51; and p is an integer of from 1 to 20.

P2-55. The conjugate according to statement P2-54, wherein G$^{LL}$ is selected from:

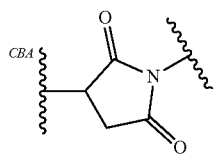

(G$^{LL1-1}$)

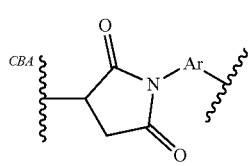

(G$^{LL1-2}$)

-continued

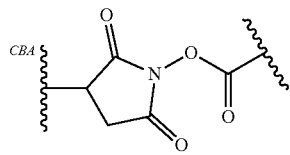

(G$^{LL2}$)

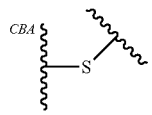

(G$^{LL3-1}$)

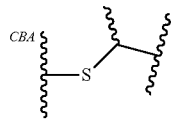

(G$^{LL3-2}$)

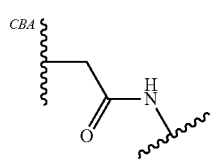

(G$^{LL4}$)

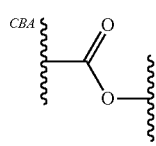

(G$^{LL5}$)

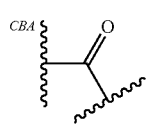

(G$^{LL6}$)

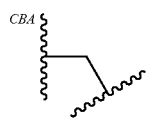

(G$^{LL7}$)

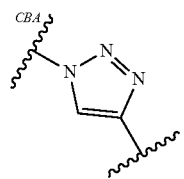

(G$^{LL8-1}$)

(G$^{LL8-2}$)

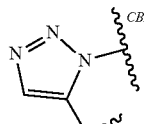

(G$^{LL9-1}$)

-continued

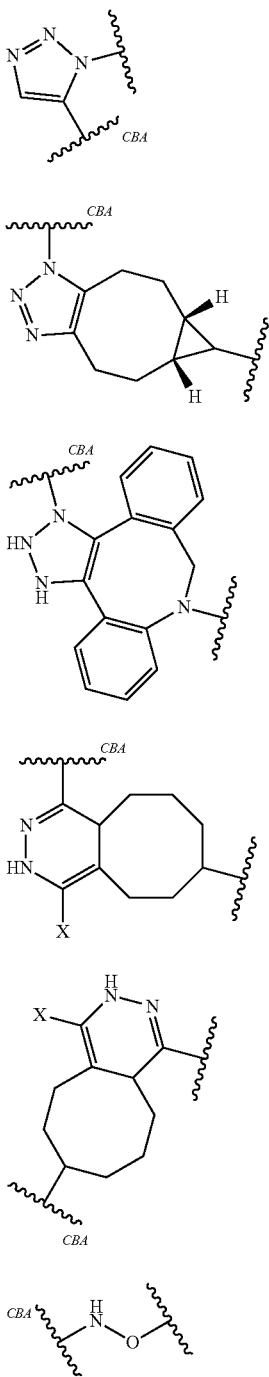

where r represents a $C_{5-6}$ arylene group and X represents $C_{1-4}$ alkyl.

P2-56. The conjugate according to statement P2-55, wherein $G^{LL}$ is selected from $G^{LL1-1}$ and $G^{LL1-2}$.

P2-57. The conjugate according to statement P2-56, wherein $G^{LL}$ is $G^{LL1-1}$.

P2-58. The conjugate according to any one of statements P2-54 to P2-57, wherein the Ligand Unit is an antibody or an active fragment thereof.

P2-59. The conjugate according to statement P2-58, wherein the antibody or antibody fragment is an antibody or antibody fragment for a tumour-associated antigen.

P2-60. The conjugate according to statement P2-59, wherein the antibody or antibody fragment is an antibody which binds to one or more tumor-associated antigens or cell-surface receptors selected from (1)-(89):
(1) BMPR1B;
(2) E16;
(3) STEAP1;
(4) 0772P;
(5) MPF;
(6) Napi3b;
(7) Sema 5b;
(8) PSCA hlg;
(9) ETBR;
(10) MSG783;
(11) STEAP2;
(12) TrpM4;
(13) CRIPTO;
(14) CD21;
(15) CD79b;
(16) FcRH2;
(17) HER2;
(18) NCA;
(19) MDP;
(20) IL20R-alpha;
(21) Brevican;
(22) EphB2R;
(23) ASLG659;
(24) PSCA;
(25) GEDA;
(26) BAFF-R;
(27) CD22;
(28) CD79a;
(29) CXCR5;
(30) HLA-DOB;
(31) P2X5;
(32) CD72;
(33) LY64;
(34) FcRH1;
(35) IRTA2;
(36) TENB2;
(37) PSMA-FOLH1;
(38) SST;
(38.1) SSTR2;
(38.2) SSTR5;
(38.3) SSTR1;
(38.4) SSTR3;
(38.5) SSTR4;
(39) ITGAV;
(40) ITGB6;
(41) CEACAM5;
(42) MET;
(43) MUC1;
(44) CA9;
(45) EGFRvIII;
(46) CD33;
(47) CD19;
(48) IL2RA;
(49) AXL;
(50) CD30-TNFRSF8;
(51) BCMA-TNFRSF17;
(52) CT Ags-CTA;
(53) CD174 (Lewis Y)-FUT3;
(54) CLEC14A;
(55) GRP78-HSPA5;
(56) CD70;
(57) Stem Cell specific antigens;
(58) ASG-5;

(59) ENPP3;
(60) PRR4;
(61) GCC-GUCY2C;
(62) Liv-1-SLC39A6;
(63) 5T4;
(64) CD56-NCMA1;
(65) CanAg;
(66) FOLR1;
(67) GPNMB;
(68) TIM-1-HAVCR1;
(69) RG-1/Prostate tumor target Mindin-Mindin/RG-1;
(70) B7-H4-VTCN1;
(71) PTK7;
(72) CD37;
(73) CD138-SDC1;
(74) CD74;
(75) Claudins—CLs;
(76) EGFR;
(77) Her3;
(78) RON-MST1R;
(79) EPHA2;
(80) CD20-MS4A1;
(81) Tenascin C—TNC;
(82) FAP;
(83) DKK-1;
(84) CD52;
(85) CS1-SLAMF7;
(86) Endoglin—ENG;
(87) Annexin A1-ANXA1;
(88) V-CAM (CD106)-VCAM1;
(89) ASCT2 (SLC1A5).

P2-61. The conjugate according to any one of statements P2-58 to P2-60, wherein the antibody or antibody fragment is a cysteine-engineered antibody.

P2-62. The conjugate according to any one of statements P2-58 to P2-61, wherein the drug loading (p) of drugs (D) to antibody (Ab) is an integer from 1 to about 10.

P2-63. The conjugate according to statement P2-62, wherein p is 1, 2, 3, 4, 5, 6, 7, 8, 9 or 10.

P2-64. A mixture of conjugates according to any one of statements P2-58 to P2-63, wherein the average drug loading per antibody in the mixture of antibody-drug conjugates is about 1 to about 10.

P2-65. The conjugate or mixture according to any one of statements P2-54 to P2-64, for use in therapy.

P2-66. A pharmaceutical composition comprising the conjugate or mixture of any one of statements P2-54 to P2-64 and a pharmaceutically acceptable diluent, carrier or excipient.

P2-67. The conjugate or mixture according to any one of statements P2-54 to P2-64, or the pharmaceutical composition according to statement P2-66, for use in the treatment of a proliferative disease in a subject.

P2-68. The conjugate, mixture or pharmaceutical composition according to statement P2-67, wherein the disease is cancer.

P2-69. Use of a conjugate or mixture according to any one of statements P2-54 to P2-64, or the pharmaceutical composition according to statement P2-66 in a method of medical treatment.

P2-70. A method of medical treatment comprising administering to a patient the pharmaceutical composition of statement P2-66.

P2-71. The method of statement P2-70 wherein the method of medical treatment is for treating cancer.

P2-72. The method of statement P2-71, wherein the patient is administered a chemotherapeutic agent, in combination with the conjugate.

P2-73. Use of a conjugate or mixture according to any one of statements P2-54 to P2-64 in a method of manufacture of a medicament for the treatment of a proliferative disease.

P2-74. A method of treating a mammal having a proliferative disease, comprising administering an effective amount of conjugate or mixture according to any one of statements P2-54 to P2-64, or the pharmaceutical composition according to statement P2-66.

P2-75. The compound A:

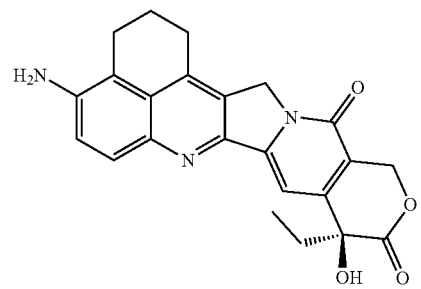

A as a single enantiomer or in an enantiomerically enriched form.

The invention claimed is:

1. A compound with the formula I:

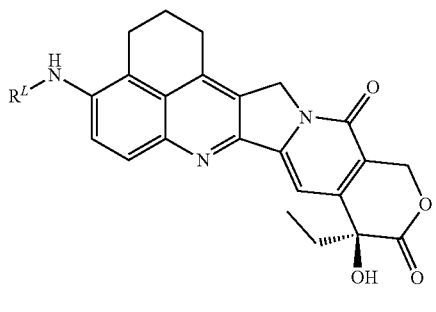

I and salts and solvates thereof, wherein $R^L$ is (Ia):

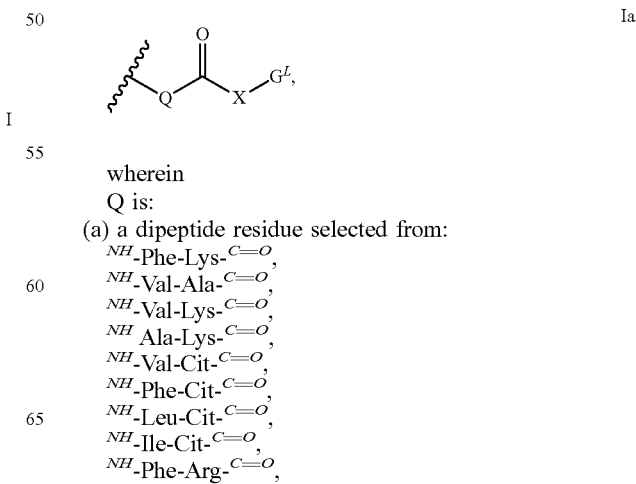

Ia wherein
Q is:
(a) a dipeptide residue selected from:
$^{NH}$-Phe-Lys-$^{C=O}$,
$^{NH}$-Val-Ala-$^{C=O}$,
$^{NH}$-Val-Lys-$^{C=O}$,
$^{NH}$-Ala-Lys-$^{C=O}$,
$^{NH}$-Val-Cit-$^{C=O}$,
$^{NH}$-Phe-Cit-$^{C=O}$,
$^{NH}$-Leu-Cit-$^{C=O}$,
$^{NH}$-Ile-Cit-$^{C=O}$,
$^{NH}$-Phe-Arg-$^{C=O}$, $^{NH}$-Trp-Cit-$^{C=O}$, and
$^{NH}$-Gly-Val-$^{C=O}$; or
(b) a tripeptide residue selected from:
$^{NH}$-Glu-Val-Ala-$^{C=O}$,
$^{NH}$-Glu-Val-Cit-$^{C=O}$,
$^{NH}$-αGlu-Val-Ala-$^{C=O}$, and
$^{NH}$-αGlu-Val-Cit-$^{C=O}$; or
(c) a tetrapeptide residue selected from:
$^{NH}$-Gly-Gly-Phe-Gly$^{C=O}$; and
$^{NH}$-Gly-Phe-Gly-Gly$^{C=O}$;
X is:

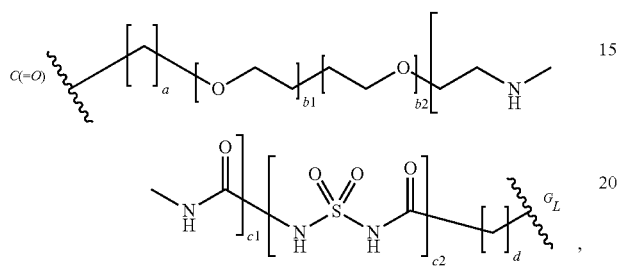

where a=0 to 5, b1=0 to 16, b2=0 to 16, c1=0 or 1, c2=0 or 1, d=0 to 5,
wherein at least b1 or b2=0 and at least c1 or c2=0; and $G^L$, is selected from:

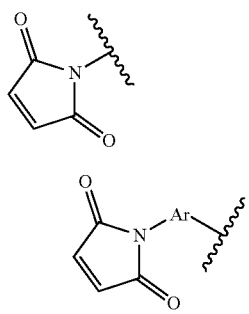
(GL1-1)

(GL1-2)

where Ar represents a $C_{5-6}$ arylene group

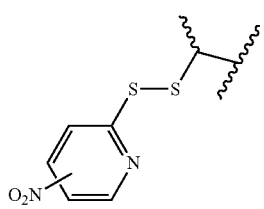
($G^{L1-3}$)

where the $NO_2$ group is optional

($G^{L8}$)

($G^{L9}$)

2. The compound according to claim 1, wherein a is:
(a) 0 to 3; or
(b) 0 or 1; or
(c) 0.
3. The compound according to claim 1, wherein b1 is:
(a) 0 to 8; or
(b) 0; or
(c) 2; or
(d) 3; or
(e) 4; or
(f) 5; or
(g) 8.
4. The compound according to claim 1, wherein b2 is:
(a) 0 to 8; or
(b) 0; or
(c) 2; or
(d) 3; or
(e) 4; or
(f) 5; or
(g) 8.
5. The compound according any to claim 1, wherein
(i) c1 is:
(a) 0; or
(b) 1; and
(ii) c2 is:
(a) 0; or
(b) 1;
wherein at least one of c1 and c2 is 0.
6. The compound according to claim 1, wherein d is:
(a) 0 to 3; or
(b) 1 or 2; or
(c) 2; or
(d) 5.
7. The compound according to claim 1, wherein:
(a) a is 0, b1 is 0, c1 is 1, c2 is 0 and d is 2, and b2 is 0, 2, 3, 4, 5 or 8; or
(b) a is 1, b2 is 0, c1 is 0, c2 is 0 and d is 0, and b1 is 0, 2, 3, 4, 5 or 8; or
(c) a is 0, b1 is 0, c1 is 0, c2 is 0 and d is 1, and b2 is 0, 2, 3, 4, 5 or 8; or
(d) b1 is 0, b2 is 0, c1 is 0, c2 is 0, one of a and d is 0, and the other of a and d is 1 or 5; or
(e) a is 1, b2 is 0, c1 is 0, c2 is 1, d is 2, and b1 is 0, 2, 3, 4, 5 or 8.
8. A compound according to claim 1, wherein $G^L$ is selected from $G^{L1-1}$ $G^{L1-2}$.
9. A conjugate of formula IV:

$$L\text{-}(D^L)_p \quad \quad (IV)$$

or a pharmaceutically acceptable salt or solvate thereof, wherein L is a Ligand unit, $D^L$ is a Drug Linker unit that is of formula III:

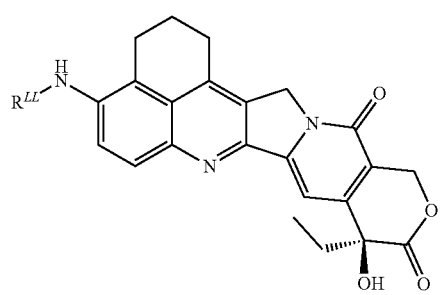

III $R^{LL}$ is a linker connected to the Ligand unit that is (Ia):

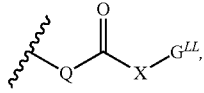
(Ia')

where Q and X are as defined in claim 1 and $G^{LL}$ is a linker connected to a Ligand Unit, wherein $G^{LL}$ is selected from

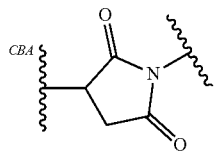
($G^{LL1-1}$)

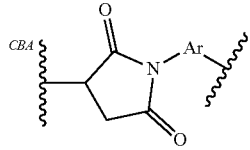
($G^{LL1-2}$)

where Ar represents a $C_{5-6}$ arylene group

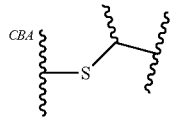
($G^{LL3-2}$)

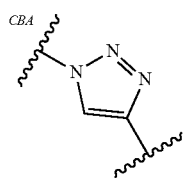
($G^{LL8-1}$)

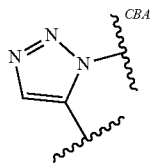
($G^{LL8-2}$)

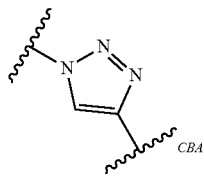
($G^{LL9-1}$)

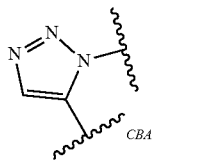
($G^{LL9-2}$)

p is an integer of from 1 to 20, and wherein the Ligand Unit is an antibody or an active fragment thereof.

10. The conjugate according to claim 9, wherein $G^{LL}$ is selected from $G^{LL1-1}$ and $G^{LL1-2}$.

11. A mixture of conjugates according to claim 9, wherein the average drug loading per antibody in the mixture of antibody-drug conjugates is 1 to 10.

12. A pharmaceutical composition comprising the conjugate of claim 9 and a pharmaceutically acceptable diluent, carrier or excipient.

13. A compound according to claim 1 that is 1-(3-(2,5-dioxo-2,5-dihydro-1H-pyrrol-1-yl)propanamido)-N—((S)-1-(((S)-1-(((S)-9-ethyl-9-hydroxy-10,13-dioxo-2,3,9,10,13,15-hexahydro-1H,12H-benzo[de]pyrano[3',4':6,7] indolizino[1,2-b]quinolin-4-yl)amino)-1-oxopropan-2-yl) amino)-3-methyl-1-oxobutan-2-yl)-3,6,9,12,15,18,21,24-octaoxaheptacosan-27-amide.

14. A compound according to claim 1 that is (S)-2-(2-(2-(2-(2-azidoethoxy)ethoxy)ethoxy)acetamido)-N—((S)-1-(((S)-9-ethyl-9-hydroxy-10,13-dioxo-2,3,9,10,13,15-hexahydro-1H,12H-benzo[de]pyrano[3',4':6,7]indolizino[1,2-b] quinolin-4-yl)amino)-1-oxopropan-2-yl)-3-methylbutanamide.

15. A compound according to claim 1 that is N—((S)-1-(((S)-1-(((S)-9-ethyl-9-hydroxy-10,13-dioxo-2,3,9,10,13,15-hexahydro-1H,12H-benzo[de]pyrano[3',4':6,7]indolizino[1,2-b]quinolin-4-yl)amino)-1-oxopropan-2-yl)amino)-3-methyl-1-oxobutan-2-yl)-4,7,10,13,16-pentaoxanonadec-18-ynamide.

* * * * *